US012774984B2

(12) United States Patent
Yang et al.

(10) Patent No.: US 12,774,984 B2
(45) Date of Patent: *Oct. 27, 2026

(54) APPARATUS, SYSTEMS, AND METHODS FOR CAPILLARY ELECTROPHORESIS

(71) Applicant: ProteinSimple, San Jose, CA (US)

(72) Inventors: Tom W. Yang, Cupertino, CA (US); David John Roach, Los Gatos, CA (US)

(73) Assignee: ProteinSimple, San Jose, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/440,572

(22) Filed: Feb. 13, 2024

(65) Prior Publication Data

US 2024/0264115 A1 Aug. 8, 2024

Related U.S. Application Data

(63) Continuation of application No. 15/707,600, filed on Sep. 18, 2017, now Pat. No. 11,933,759, which is a (Continued)

(51) Int. Cl.

| | |
|---|---|
| ***G01N 27/447*** | (2006.01) |
| *C07K 1/26* | (2006.01) |
| *C07K 1/28* | (2006.01) |

(52) U.S. Cl.

CPC . *G01N 27/44782* (2013.01); *G01N 27/44704* (2013.01); *C07K 1/26* (2013.01); (Continued)

(58) Field of Classification Search

CPC ....... G01N 27/44782; G01N 27/44704; G01N 27/44726; G01N 27/44791; C07K 1/26; C07K 1/285

See application file for complete search history.

(56) References Cited

U.S. PATENT DOCUMENTS 4,021,364 A 5/1977 Speiser et al.
4,128,470 A 12/1978 Hiratsuka et al.
(Continued)

FOREIGN PATENT DOCUMENTS

CN 1737562 A 2/2006
CN 101750450 6/2010
(Continued)

OTHER PUBLICATIONS

Biorad Laboratories Inc., "A Guide to Polyacrylamide Gel Electrophoresis and Detection Begin," Jan. 1, 2011, Hercules, CA, Retrieved from the Internet: URL: http://www.bio-rad.com/webroot/web/pdf/lsr/literature/Bulletin_6040A.pdf [retrieved Mar. 3, 2015].
(Continued)

*Primary Examiner* — James Lin
*Assistant Examiner* — Vivian A Tran
(74) *Attorney, Agent, or Firm* — Casimir Jones, S.C.; Brian F. Bradley

(57) ABSTRACT

An apparatus includes a body portion that defines a reservoir and a set of substantially flexible capillaries. The set of substantially flexible capillaries are fixedly coupled to the body portion and in fluid communication with the reservoir. A connector is configured to be coupled to the body portion to be in fluid communication with the reservoir and the set of substantially flexible capillaries. The connector is further configured to be coupled to a vacuum source. The apparatus is arranged such that at least a part of the body portion is electrically conductive. Methods for separating and detecting an analyte from a biological sample with the apparatus are also provided. For example, methods for separating and detecting one or more proteins from a cellular lysate or a purified protein are also provided.

10 Claims, 31 Drawing Sheets

Related U.S. Application Data continuation of application No. 14/039,995, filed on Sep. 27, 2013, now Pat. No. 9,766,206.

(52) U.S. Cl.
CPC ........ *C07K 1/285* (2013.01); *G01N 27/44726* (2013.01); *G01N 27/44791* (2013.01)

(56) References Cited

U.S. PATENT DOCUMENTS

| | | | |
|---|---|---|---|
| 4,716,101 | A | 12/1987 | Thompson et al. |
| 4,747,919 | A | 5/1988 | Anderson |
| 4,788,138 | A | 11/1988 | Tung et al. |
| 4,810,781 | A | 3/1989 | Hollinshead |
| 4,843,010 | A | 6/1989 | Nowinski et al. |
| 4,870,003 | A | 9/1989 | Kortright et al. |
| 4,921,790 | A | 5/1990 | O'Brien |
| 5,096,807 | A | 3/1992 | Leaback |
| 5,110,434 | A | 5/1992 | Zhu et al. |
| 5,169,511 | A * | 12/1992 | Allington ......... G01N 27/44782 204/601 |
| 5,180,475 | A | 1/1993 | Young et al. |
| 5,228,960 | A | 7/1993 | Liu et al. |
| 5,242,404 | A | 9/1993 | Conley et al. |
| 5,244,813 | A | 9/1993 | Walt et al. |
| 5,264,101 | A | 11/1993 | Demorest et al. |
| 5,348,633 | A | 9/1994 | Karger et al. |
| 5,354,440 | A | 10/1994 | Allington |
| 5,384,024 | A | 1/1995 | Moring et al. |
| 5,423,966 | A | 6/1995 | Wiktorowicz |
| 5,439,578 | A | 8/1995 | Dovichi et al. |
| 5,482,867 | A | 1/1996 | Barrett et al. |
| 5,597,468 | A | 1/1997 | Lauer et al. |
| 5,614,073 | A | 3/1997 | Bobbitt et al. |
| 5,630,924 | A | 5/1997 | Fuchs et al. |
| 5,633,129 | A | 5/1997 | Karger et al. |
| 5,759,770 | A | 6/1998 | Guertler et al. |
| 5,804,384 | A | 9/1998 | Muller et al. |
| 5,840,503 | A | 11/1998 | Beausang et al. |
| 5,856,100 | A | 1/1999 | Hayashizaki |
| 5,858,188 | A | 1/1999 | Soane et al. |
| 5,932,080 | A | 8/1999 | Likuski |
| 5,976,336 | A | 11/1999 | Dubrow et al. |
| 5,976,896 | A | 11/1999 | Kumar et al. |
| 5,985,121 | A | 11/1999 | Wu et al. |
| 6,054,032 | A | 4/2000 | Haddad et al. |
| 6,100,045 | A | 8/2000 | Van Es |
| 6,107,038 | A | 8/2000 | Choudhary et al. |
| 6,139,797 | A | 10/2000 | Suzuki et al. |
| 6,232,464 | B1 | 5/2001 | Lange |
| 6,322,683 | B1 | 11/2001 | Wolk et al. |
| 6,328,869 | B1 | 12/2001 | Ogle |
| 6,375,817 | B1 | 4/2002 | Taylor et al. |
| 6,423,536 | B1 | 7/2002 | Jovanovich et al. |
| 6,475,364 | B1 | 11/2002 | Dubrow et al. |
| 6,536,477 | B1 | 3/2003 | O'Connor et al. |
| 6,676,819 | B1 | 1/2004 | Liu et al. |
| 6,818,112 | B2 | 11/2004 | Schneider et al. |
| 6,833,062 | B2 | 12/2004 | Kennedy et al. |
| 6,989,132 | B2 | 1/2006 | Yamamoto |
| 7,316,770 | B2 | 1/2008 | Inaba et al. |
| 7,935,489 | B2 | 5/2011 | O'Neill et al. |
| 8,021,611 | B2 | 9/2011 | Roach et al. |
| 8,945,361 | B2 | 2/2015 | Gentalen et al. |
| 9,377,440 | B2 | 6/2016 | Wu et al. |
| 9,766,206 | B2 * | 9/2017 | Yang ................ G01N 27/44704 |
| 11,933,759 | B2 * | 3/2024 | Yang ................ G01N 27/44782 |
| 2002/0071847 | A1 | 6/2002 | Sadziene et al. |
| 2002/0110900 | A1 | 8/2002 | Jovanovich et al. |
| 2002/0112959 | A1 | 8/2002 | Xue et al. |
| 2002/0115740 | A1 | 8/2002 | Beuhler et al. |
| 2002/0166769 | A1 | 11/2002 | Serikov |
| 2003/0032198 | A1 | 2/2003 | Lugmair et al. |
| 2003/0062265 | A1 | 4/2003 | King et al. |
| 2003/0078314 | A1 | 4/2003 | Johnson et al. |
| 2003/0128043 | A1 | 7/2003 | Zeltz et al. |
| 2003/0221965 | A1 | 12/2003 | Seino et al. |
| 2003/0228241 | A1 | 12/2003 | Legge |
| 2004/0045825 | A1 | 3/2004 | Chiou et al. |
| 2004/0079638 | A1 | 4/2004 | Rooney et al. |
| 2004/0166546 | A1 | 8/2004 | Warmington et al. |
| 2004/0188255 | A1 | 9/2004 | Kennedy et al. |
| 2006/0057576 | A1 | 3/2006 | Paszkowski et al. |
| 2006/0292649 | A1 | 12/2006 | Cahill et al. |
| 2008/0017512 | A1 | 1/2008 | Bordunov et al. |
| 2008/0035484 | A1 | 2/2008 | Wu et al. |
| 2009/0023156 | A1 | 1/2009 | Voss et al. |
| 2010/0108513 | A1 * | 5/2010 | Amirkhanian ... G01N 27/44721 204/603 |
| 2011/0011740 | A1 | 1/2011 | Roach et al. |
| 2011/0032639 | A1 | 2/2011 | Khan et al. |
| 2012/0213667 | A1 * | 8/2012 | Roach ..................... F16L 41/00 422/63 |
| 2012/0322686 | A1 | 12/2012 | Lyon et al. |
| 2013/0008236 | A1 | 1/2013 | Rechner |
| 2013/0280696 | A1 * | 10/2013 | Millenson ........ G01N 33/56988 435/5 |
| 2013/0280815 | A1 | 10/2013 | Wu |
| 2014/0262516 | A1 | 9/2014 | Larson |
| 2015/0093757 | A1 | 4/2015 | Gavin |
| 2018/0106758 | A1 | 4/2018 | Yang et al. |
| 2024/0192164 | A1 | 6/2024 | Tran et al. |

FOREIGN PATENT DOCUMENTS

| | | | |
|---|---|---|---|
| CN | 202407437 | U | 9/2012 |
| CN | 101750450 | B | 3/2013 |
| DE | 20022785 | U | 10/2002 |
| EP | 0805215 | A2 | 11/1997 |
| GB | 1088308 | | 10/1967 |
| JP | H0210150 | A | 1/1990 |
| JP | H05172815 | A | 7/1993 |
| JP | 2002228669 | | 8/2002 |
| JP | 2003505711 | | 2/2003 |
| JP | 2004532384 | | 10/2004 |
| JP | 2006519363 | | 8/2006 |
| WO | WO-9963408 | A1 | 12/1999 |
| WO | WO-0155721 | A2 | 8/2001 |
| WO | WO-02059589 | A2 | 8/2002 |
| WO | WO-03010528 | A1 | 2/2003 |
| WO | WO-03062815 | A1 | 7/2003 |
| WO | WO-03100086 | A1 | 12/2003 |

OTHER PUBLICATIONS

Chang, W., et al., "Enhanced Resolution Achieved with Electroosmotic Flow Control in Capillary Isoelectric Focusing with Dynamic Coatings," Am. Biotechnology. Lab. (2005).

Final Office Action mailed on Oct. 18, 2021 for U.S. Appl. No. 15/707,600, filed Sep. 30, 2017, 36 pages.

First Office Action for Chinese Application No. 201480052918.9, mailed Feb. 20, 2017, 6 pages.

International Search Report and Written Opinion for International Application No. PCT/US2014/057738, mailed Mar. 11, 2015, 10 pages.

Misiakos et al., "A Multi-Band Capillary Immunosensor," Biosensors & Bioelectronics, 13:825-830 (1998).

Non-Final Office Action for U.S. Appl. No. 15/707,600 mailed on Jun. 24, 2022, 32 pages.

Notice of Reasons for Rejection for Japanese Application No. 2016-545240, mailed Jul. 27, 2018, 9 pages.

Office Action for European Application No. 14847699.7, mailed Aug. 27, 2020, 4 pages.

Office Action for European Application No. 14847699.7, mailed Aug. 30, 2019, 4 pages.

Office Action for European Application No. 14847699.7, mailed Mar. 25, 2022, 4 pages.

Office Action for U.S. Appl. No. 14/039,995, mailed Jan. 25, 2017, 16 pages.

Office Action for U.S. Appl. No. 14/039,995, mailed Jul. 1, 2016, 11 pages.

(56) References Cited

OTHER PUBLICATIONS

Office Action for U.S. Appl. No. 15/707,600, mailed Dec. 8, 2020, 31 pages.
Office Action for U.S. Appl. No. 15/707,600, mailed Mar. 26, 2020, 13 pages.
Office Action for U.S. Appl. No. 15/707,600, mailed Sep. 19, 2019, 12 pages.
O'Neill, R. A. et al., "Isoelectric Focusing Technology Quantifies Protein Signaling in 25 Cells," PNAS, 103:16153-16158 (2006).
Second Office Action for Chinese Application No. 201480052918.9, mailed Nov. 3, 2017, 8 pages.
Supplementary European Search Report for European Application No. 14847699.7, mailed Apr. 7, 2017, 12 pages.
Third Office Action for Chinese Application No. 201480052918.9, mailed Apr. 27, 2018, 5 pages (with partial summary translation).
Vilkner, T. et al., "Micro Total Analysis Systems. Recent Developments," Analytical Chemistry, 76(12):3373-3385 (2004).
Wu, J. et al., "Capillary isoelectric focusing with whole col. detection and a membrane sample preparation system," Analytica Chimica Acta, 383(1-2):67-78 (1999).
Extended European Search Report for European Application No. 24169233.4, dated Sep. 20, 2024, 06 Pages.
Extended European Search Report for European Application No. EP20874350.0, dated Oct. 10, 2023, 22 pages.
Fonslow B.R., et al., "Free-Flow Electrophoresis on an Anodic Bonded Glass Microchip," Analytical Chemistry, American Chemical Society, Sep. 1, 2005, vol. 77, No. 17, pp. 5706-5710, DOI: 10.1021/AC050766N, XP008154056.
Nissum M., et al., "Free-Flow Electrophoresis of the Human Urinary Proteome," Methods in Molecular Microbiology, Jan. 1, 2008, vol. 484, pp. 131-144.
Novo P., et al., "Current Advances and Challenges in Microfluidic Free-Flow Electrophoresis—A Critical Review," Analytica Chimica Acta, Aug. 23, 2017, vol. 991, pp. 9-29, DOI: 10.1016/J.ACA.2017.08.017, ISSN: 0003-2670, XP085211590.
Wikipedia: "Free-Flow Electrophoresis—Wikipedia," Jan. 21, 2019, 03 Pages, XP093087203, [Retrieved on Sep. 29, 2023] Retrieved from URL: https://en.wikipedia.org/w/index.php?title=Free-flow_electrophoresis&oldid=879460286.
Extended European Search Report for European Application No. 26169814.6, dated Jul. 3, 2026, 7 pages.

* cited by examiner

APPARATUS, SYSTEMS, AND METHODS FOR CAPILLARY ELECTROPHORESIS

CROSS-REFERENCE TO RELATED APPLICATION

This application is a continuation of U.S. patent application Ser. No. 15/707,600, filed Sep. 18, 2017, which claims priority to U.S. application Ser. No. 14/039,995, now U.S. Pat. No. 9,766,206, entitled, "APPARATUS, SYSTEMS, AND METHODS FOR CAPILLARY ELECTROPHORESIS," filed Sep. 27, 2013, the disclosure of which is incorporated herein by reference in its entirety.

BACKGROUND

The embodiments described herein relate generally to electrophoresis used for separating an analyte or analytes present in a sample, for example a biological sample, and downstream detection, identification and/or quantification of the analyte or analytes. More particularly, the embodiments described herein relate to apparatus, systems, and methods for capillary electrophoresis.

Electrophoresis has been used for separating mixtures of molecules based on their different rates of travel in electric fields. Generally, electrophoresis refers to the movement of suspended or dissolved molecules through a fluid or gel under the action of an electromotive force applied to one or more electrodes or electrically conductive members in contact with the fluid or gel. Some known modes of electrophoretic separation include separating molecules based, at least in part, on differences in their mobilities in a buffer solution (commonly referred to as zone electrophoresis), in a gel or polymer solution (commonly referred to as gel electrophoresis), or in a potential of hydrogen (pH) gradient (commonly referred to as isoelectric focusing). The movement of molecules during electrophoresis can be highly variable, making interpretation dependent upon a comparison to electrophoresis standards, whose behavior and identity have been previously characterized. Electrophoresis standards include, for example, molecular weight (MW) standards in sodium dodecyl sulfate polyacrylamide gel electrophoresis (SDS-PAGE) and deoxyribonucleic acid (DNA) size standards in agarose gels In some instances, electrophoresis standards are used in some known Western blotting techniques (also referred to as "Western blots" or "Westerns" or "protein immunoblots"). In such techniques, proteins are separated through a size matrix (e.g., a polyacrylamide gel) and then transferred to a solid support such as a nitrocellulose filter for subsequent visualization and characterization. The location of a specific protein of interest is identified by probing the solid support (e.g., nitrocellulose filter) with one or more antibodies to that protein. For example, the first antibody (i.e., primary antibody) binds the specific protein and then the protein-antibody complex is probed with a secondary antibody conjugated to a detection molecule (e.g., a chemiluminescent molecule). The secondary antibody binds the primary antibody, or a region of the primary antibody-protein complex. Generally, the separation mode in electrophoresis is by molecular weight.

Biomolecule separation can also be carried out in a capillary tube by capillary electrophoresis. A biomolecule (e.g., protein) can then be visualized by immobilizing the biomolecule to the wall of the capillary tube. However, capillary electrophoresis techniques followed by biomolecule visualization is difficult to perform consistently.

Therefore, it is desirable to develop techniques for assaying very small volumes (e.g., nanoliter to microliter volumes) of biological material (e.g., cellular lysate or purified protein) in capillaries, with resulting information having content similar to that of a Western gel blot but without the complex, extensive, and/or time-consuming handling and processing steps that adversely affect reproducibility and make automation difficult. It is also desirable to automate such techniques so that multiple samples may be analyzed simultaneously or in rapid succession with ease and robustness while consuming minimal volumes of expensive reagents and/or disposables.

Thus, a need exists for improved apparatus, systems, and methods for capillary electrophoresis of a sample, followed by visualization and detection of one or more analytes in the sample. The present invention addresses this and other needs.

SUMMARY

Apparatus, methods, and systems for capillary electrophoresis followed by downstream analyte visualization and characterization are described herein. In some embodiments, an apparatus includes a body portion that defines a reservoir and a set of substantially flexible capillaries. The set of substantially flexible capillaries are fixedly coupled to the body portion and in fluid communication with the reservoir. A connector is configured to be coupled to the body portion to be in fluid communication with the reservoir and the set of substantially flexible capillaries. The connector is further configured to be coupled to a vacuum source. The apparatus is arranged such that at least a part of the body portion is electrically conductive.

In one aspect, the apparatus and system provided herein is used in a capillary electrophoresis apparatus to separate one or more analytes of interest from a heterogeneous biological sample, for example a cellular lysate or a purified protein. The apparatus and system provide an automated methodology to carry out the method, as well as components to manipulate the separated sample for visualization, detection and quantification of the one or more analytes in the sample. In one embodiment, the biological sample is a cellular lysate comprising the lysate of a single stem cell, or a population of stem cells. In one embodiment, the biological sample is a cellular lysate comprising the lysate of a single cancer cell, or a population of cancer cells. In other embodiments, a purified protein is used as the sample. The purified protein can be from a single cell or a population of cells.

DETAILED DESCRIPTION

Figure 1:
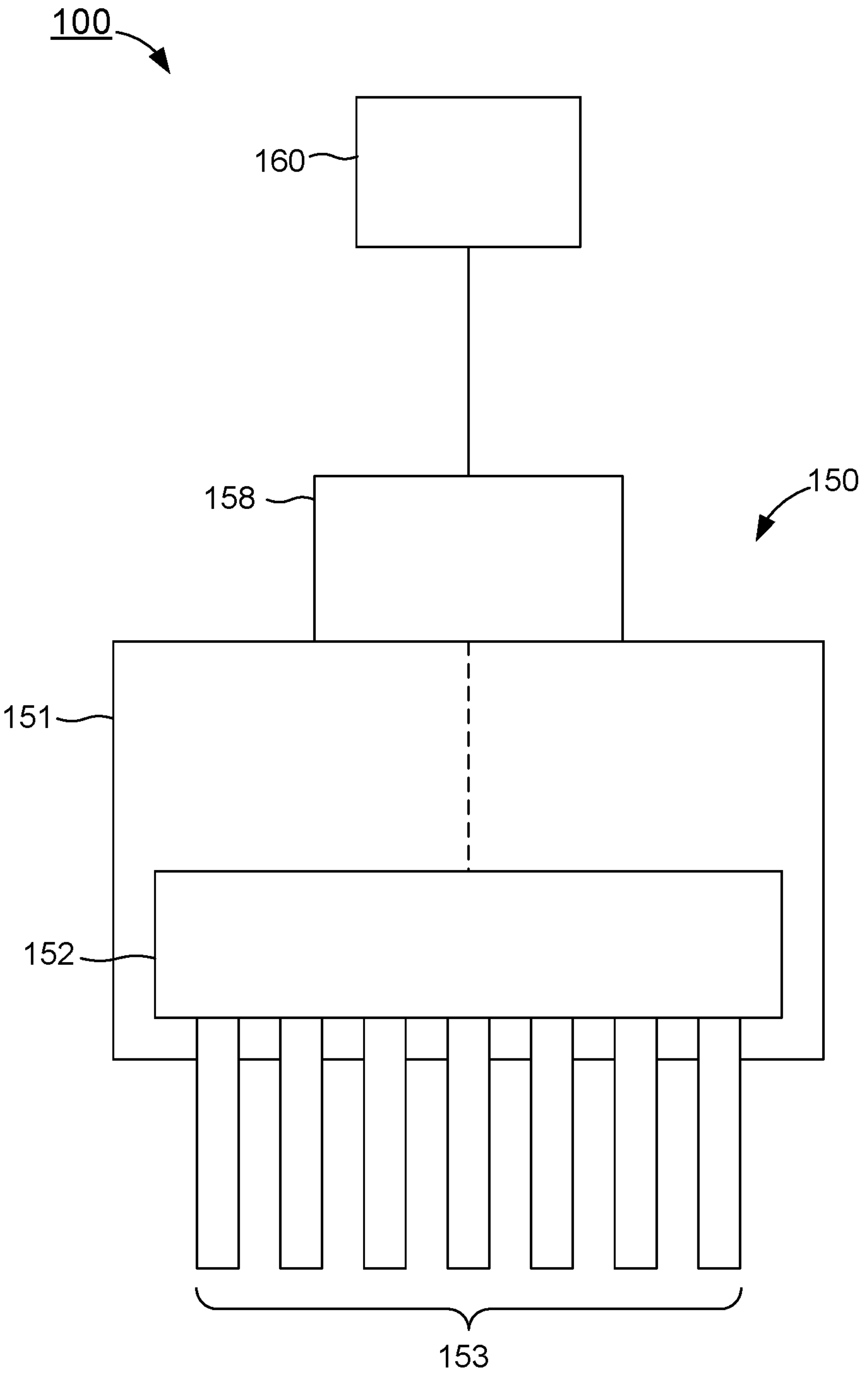
FIG. 1 is a schematic illustration of a portion of a capillary electrophoresis system according to an embodiment.

Apparatuses, methods, and systems for capillary electrophoresis are described herein. The apparatuses and systems are configured to carry out capillary electrophoresis in a parallel or serial manner on one or multiple samples, followed by visualization and characterization on one or more analytes of interest, which might be present in the one or multiple samples.

In some embodiments, an apparatus includes a body portion that defines a reservoir and a set of substantially flexible capillaries. The set of substantially flexible capillaries are fixedly coupled to the body portion and in fluid communication with the reservoir. A connector is configured to be coupled to the body portion to be in fluid communication with the reservoir and the set of substantially flexible capillaries. The connector is further configured to be coupled to a vacuum source. The apparatus is arranged such that at least a part of the body portion is electrically conductive.

In some embodiments, a system for capillary electrophoresis, for example to separate a plurality of proteins in a heterogeneous sample (e.g., a cellular lysate or a purified protein) includes a housing, a capillary cartridge retainer, a vacuum source, a light source, an optical detector, and a reagent tray holder. The capillary cartridge retainer is movably coupled within the housing and is configured to move along a single axis. The vacuum source is coupled to the capillary cartridge retainer and is configured to be fluidically coupled to a capillary cartridge when the capillary cartridge is positioned in the capillary cartridge retainer. The light source is movably coupled within the housing and is disposed on a first side of the capillary cartridge retainer. The optical detector is disposed within the housing on a second side of the capillary cartridge retainer. The reagent tray holder is movably coupled to the housing and is configured to move in a direction substantially normal to the axis of movement of the capillary cartridge retainer.

In some embodiments, a method of using a capillary electrophoresis system includes moving a capillary cartridge along a vertical axis from a first position within a housing to a second position within the housing. The capillary cartridge includes an electrically conductive body portion and a set of capillaries fixedly coupled to the body portion. When in the first position, the capillaries are disposed outside of a well plate in the first position, and when in the second position, the capillaries are disposed in a sample in the well plate. The method includes actuating a vacuum when the capillary cartridge is in the second position to draw at least a portion of the sample into the set of capillaries. With the portion of the sample drawn into the set of capillaries, the portion of the sample is maintained in the capillaries in a substantially fixed position. A light source is moved from a first position disposed apart from the capillary cartridge to a second position adjacent to the capillary cartridge and analytes within the portion of the sample are separated.

As used in this specification, the singular forms "a," "an" and "the" include plural referents unless the context clearly dictates otherwise. Thus, for example, the term "a member" is intended to mean a single member or a combination of members, "a material" is intended to mean one or more materials, or a combination thereof.

As used herein, the terms "about" and "approximately" generally mean plus or minus 10% of the value stated. For example, about 0.5 would include 0.45 and 0.55, about 10 would include 9 to 11, about 1000 would include 900 to 1100.

As used herein, the term "set" can refer to multiple features or a singular feature with multiple parts. For example, when referring to a set of walls, the set of walls can be considered as one wall with multiple portions, or the set of walls can be considered as multiple, distinct walls. Thus, a monolithically constructed item can include a set of walls. Such a set of walls may include multiple portions that are either continuous or discontinuous from each other. A set of walls can also be fabricated from multiple items that are produced separately and are later joined together (e.g., via a weld, an adhesive, or any suitable method).

As used herein, the terms "perpendicular," "normal," and "orthogonal" generally described a relationship between two geometric constructions (e.g., two lines, two planes, a line and a plane, or the like) in which the two geometric constructions are disposed at substantially 90°. For example, a line is said to be perpendicular to another line when the lines intersect at an angle substantially equal to 90°. Similarly, when a planar surface (e.g., a two dimensional surface) is said to be orthogonal to another planar surface, the planar surfaces are disposed at substantially 90° as the planar surfaces extend to infinity.

As used herein, the terms "analyte" and/or "target analyte" refer to any molecule or compound to be separated and/or detected with the methods, apparatuses and systems provided herein. Suitable analytes include, but are not limited to, small chemical molecules such as, for example, environmental molecules, clinical molecules, chemicals, pollutants, and/or biomolecules. More specifically, such chemical molecules can include, but are not limited to pesticides, insecticides, toxins, therapeutic and/or abused drugs, antibiotics, organic materials, hormones, antibodies, antibody fragments, antibody-molecule conjugates (e.g., antibody-drug conjugates), antigens, cellular membrane antigen, proteins (e.g., enzymes, immunoglobulins, and/or glycoproteins), nucleic acids (e.g., DNA and/or RNA), lipids, lectins, carbohydrates, whole cells (e.g., prokaryotic cells such as pathogenic bacteria and/or eukaryotic cells such as mammalian tumor cells), viruses, spores, polysaccharides, glycoproteins, metabolites, cofactors, nucleotides, polynucleotides (comprising ribonucleic acid and/or deoxyribonucleic acid), transition state analogs, inhibitors, receptors, receptor ligands (e.g., neural receptors or their ligands, hormonal receptors or their ligands, nutrient receptors or their ligands, and/or cell surface receptors or their ligands), receptor-ligand complexes, nutrients, electrolytes, growth factors and other biomolecules and/or non-biomolecules, as well as fragments and combinations thereof. In one embodiment, the analyte is a protein or a protein complex, and the sample is a cellular lysate or a purified protein.

As used herein, the term "sample" refers to a composition that contains an analyte or analytes to be detected. A sample, in one embodiment, is heterogeneous, containing a variety of components (e.g., different proteins) or homogenous, containing one component (e.g., a population of one protein). In some instances, a sample can be naturally occurring, a biological material, and/or a man-made material. Furthermore, a sample can be in a native (e.g., a cell suspension) or denatured form (e.g., a lysate). In some instances, a sample can be a single cell (or contents of a single cell, e.g., as a cellular lysate from the single cell, or a purified protein) or multiple cells (or contents of multiple cells, e.g., as a cellular lysate from the multiple cells, or a purified protein from the multiple cells), a blood sample, a tissue sample, a skin sample, a urine sample, a water sample, and/or a soil sample. In some instances, a sample can be from a living organism, such as a eukaryote, prokaryote, mammal, human, yeast, and/or bacterium or the sample can be from a virus.

In one embodiment, the sample is a heterogeneous biological sample or derived from a heterogeneous biological sample, for example a tissue lysate, a cellular lysate or a mixture of biomolecules such as proteins (e.g., a purified protein). In a further embodiment, a protein within the cellular lysate is the analyte to be detected by the methods and systems described herein. In a further embodiment, the apparatuses, systems and methods provided herein provide for the detection of a particular form of a protein, for example, a phosphorylated protein. The cellular lysate, for example, can be the lysate of one cell or a mixture of cells. Moreover, the cellular lysate can include a single cell type, or multiple cell types. The cell type, in one embodiment, includes a stem cell or a cancer cell, or a population of stem cells, or a population of cancer cells. In one embodiment, a sample comprises one or more stem cells (e.g., any cell that has the ability to divide for indefinite periods of time and to give rise to specialized cells). Suitable examples of stem cells can include but are not limited to embryonic stem cells (e.g., human embryonic stem cells (hES)), and non-embryonic stems cells (e.g., mesenchymal, hematopoietic, induced pluripotent stem cells (iPS cells), or adult stem cells (MSC)).

In some instances, prior to separating and detecting an analyte in a sample with the apparatuses and systems provided herein, processing may be performed on the sample. For example, a sample can be subjected to a lysing step, denaturation step, heating step, purification step (e.g., protein purification), precipitation step, immunoprecipitation step, column chromatography step, centrifugation, etc. In one embodiment, a sample is subjected to a denaturation step prior to separating and detecting a target analyte in a sample with the methods, apparatuses and systems described herein. The processing step on the sample in one embodiment, is performed in one of the apparatuses or systems described herein. In another embodiment, the processing step is performed prior to introducing the sample into one of the apparatuses or systems set forth herein.

As used herein, the terms "standard" and/or "internal standard" refer to a well-characterized substance of known amount and/or identity (e.g., known molecular weight, electrophoretic mobility profile, number of base pairs in the case of a nucleic acid, molecular composition) that can be added to a sample comprising the analyte, for comparative purposes. In one embodiment, a known quantity of standard is added to a sample comprising one or more analytes, and both the standard and the molecules in the sample, including the analyte(s) are separated on the basis of molecular weight by electrophoresis). A comparison of the standard and analyte signal then provides a quantitative or semi-quantitative measure of the amount of analyte originally present in the sample.

Molecular weight standards are known in the art, and are available commercially. One of skill in the art, depending on the molecular weight of the analyte of interest or the estimated molecular weight range, can choose a suitable standard to use with the methods, apparatuses and systems provided herein. The standard and the analyte(s) can be detected with one or more detection molecules or reagents, such as with an antibody against the analyte or a labeling moiety attached to the standard. In one embodiment, a primary antibody is used to bind the target analyte, and a secondary antibody conjugated to a fluorescent or chemiluminescent reagent is introduced to bind the primary antibody or the primary antibody-analyte complex. The signal of the fluorescent or chemiluminescent molecule is then detected.

The signal of the standard and the signal of the analyte(s) can then be compared to measure the concentration of the analyte(s) in the sample, or the molecular weight of the analyte, if for example, the standard is a molecular weight ladder standard (available commercially). As provided above, internal standards are detected by, for example, fluorescence or chemiluminescence. In other embodiments, standards, such as molecular weight ladders are prestained and do not require an additional reagent for visualization.

In some embodiments, an internal standard can be a purified form of the analyte itself, which is generally made distinguishable from the analyte in some way. Any method of obtaining a purified form of the analyte can include but is not limited to purification from nature, purification from organisms grown in the laboratory (e.g., via chemical synthesis), and/or the like. The distinguishing characteristic of an internal standard can be any suitable change that can include but is not limited to dye labeling, radiolabeling, or modifying the mobility of the standard during the electrophoretic separation so that it is separated from the analyte. For example, a standard can contain a modification of the analyte that changes the charge, mass, and/or length (e.g., via deletion, fusion, and/or chemical modification) of the standard relative to the analyte of interest. Thus, the analyte and the internal standard can each be labeled with fluorescent dyes that are each detectable at discrete emission wavelengths, thereby allowing the analyte and the standard to be independently detectable. In some instances, an internal standard is different from the analyte but behaves in a way similar to or the same as the analyte, enabling relevant comparative measurements. In some embodiments, a standard that is suitable for use can be any of those described in U.S. Patent Application Publication No. 2007/0062813, the disclosure of which is incorporated herein by reference in its entirety.

In some instances, multiple analytes are detected and characterized from a single sample in a single capillary tube by the apparatuses, systems and methods provided herein. For example, in one embodiment, the multiple analytes are a population of proteins or a subpopulation of proteins. In this regard, it is often not practical to include a single internal standard corresponding to each of the individual proteins of the population of proteins or subpopulation of proteins. Accordingly, in one embodiment, a general molecular weight standard is introduced into the systems and apparatuses provided herein. The molecular weight standard, in some embodiments, is a ladder standard, which when visualizes, shows different molecular weights along the capillary tube. Proteins in the sample that migrate during the electrophoresis are compared to the ladder to determine the weight of the proteins present in the sample. In one embodiment, multiple molecular weight ladder standards are used.

Electrophoresis standards can be synthesized to exhibit a broad range of characteristics and/or mobilities. In some embodiments, electrophoresis standards have a molecular weight in the range of about 20 Dalton (Da) to about 800 kiloDalton (kDa). Electrophoresis standards generally include of one or more moieties capable of affecting electrophoretic mobility, capable of detection, and/or capable of immobilizing the standard. For example, an electrophoresis standard can include one or more moieties capable of immobilizing the standard by covalently linking the standard to a substrate. The one or more moieties can include, for example, one or more functional groups configured to exhibit and/or perform the desired functionality.

Analytes and/or standards described above, in one embodiment, are separated by any physical characteristic including but not limited to their size (e.g., molecular weight, oligonucleotide length). For example, in one embodiment, a sample is subjected to an electrophoretic separation in a capillary tube comprising a separation matrix, based on size of the molecules in the sample in the apparatuses and systems described herein.

As provided throughout, the present invention relates to resolving one or more analytes includes electrophoresis of a sample in a capillary tube, present in the apparatus and system described herein. The methods, systems and apparatuses described herein are configured to perform capillary electrophoresis on one or more samples present in one or multiple capillary tubes, in a serial or parallel manner, in an automated fashion.

The capillary tube comprises a separation matrix, which can be added in an automated fashion by the apparatus and/or system. The separation matrix, in one embodiment, is a size separation matrix, and has similar or substantially the same properties of a polymeric gel, used in conventional electrophoresis experiments. Capillary electrophoresis in the separation matrix is analogous to separation in a polymeric gel, such as a polyacrylamide gel or an agarose gel, where molecules are separated on the basis of the size of the molecules in the sample, by providing a porous passageway through which the molecules can travel. The separation matrix permits the separation of molecules by molecular size because larger molecules will travel more slowly through the matrix than smaller molecules.

In one embodiment, once the separation is complete, the components of the separated sample (e.g., including the analytes and/or standards) are immobilized to a wall(s) of the capillary using any suitable method including but not limited to chemical, photochemical, and heat treatment. In some embodiments, the components of the separated sample are immobilized in a fluid path (e.g., defined by a capillary or the like) after the molecules have been separated by electrophoresis. For example, in one embodiment, immobilization occurs by subjecting the separated sample and the capillaries to ultraviolet (UV) light, which serves to immobilize the analyte(s) (if present in the sample) and molecules in the sample to the walls of the capillary. The immobilization can be via covalent bonds or non-covalent means such as by hydrophobic or ionic interaction. In another embodiment, a reactive moiety can be used to covalently immobilize the resolved analyte or analytes in the fluid path. The reactive moiety can be attached directly or indirectly to the fluid path (e.g., on the wall(s) of the capillary tube). In some embodiments, the reactive moiety can be supplied in solution or suspension, and can be configured to form bridges between the wall of the fluid path and the molecules in the sample upon activation. The reactive moiety can line the fluid path or can be present on a linear or cross-linked polymer in the fluid path, which may or may not be linked to the wall of the fluid path before and/or after activation. The reactive moiety can be and/or can include any reactive group that is capable of forming a covalent linkage with a corresponding reactive group of individual molecules of the sample such as, for example, those described above.

In some embodiments, the reactive moiety comprises a functional group that can be converted to a functionality that adheres to an analyte via hydrophobic interactions, ionic interactions, hydrogen bonding etc. In some embodiments, such reactive moieties are activated with the UV light, laser, temperature, or any other source of energy in order to immobilize the analytes onto the surfaces of the fluid paths and/or onto the surfaces of particles attached to the surfaces of fluid paths. In some embodiments, the surfaces of the fluid paths are functionalized with thermally responsive polymers that enable changes in hydrophobicity of the surfaces upon changing the temperature. In some embodiments, the analytes are immobilize on such surfaces by increasing hydrophobicity of a temperature responding polymer when a certain temperature is reached within the fluid path.

Immobilized analytes and/or standards are then probed for, and detected with one or more detection agents. A detection agent is capable of binding to or interacting with the analyte and/or standard to be detected. Detection agents allow the detection of a standard and an analyte by any means such as but not limited to fluorescent dye(s), optical dye(s), chemiluminescent reagent(s), radioactivity, particles, magnetic particle(s), paramagnetic particle(s), etc. Detection agents can include any organic or inorganic molecules such as, for example, proteins, peptides, antibodies, enzyme substrates, transition state analogs, cofactors, nucleotides, polynucleotides, aptamers, lectins, small molecules, ligands, inhibitors, drugs, and other biomolecules as well as non-biomolecules capable of binding the analyte to be detected. In some embodiments, the detection agents comprise one or more label moieties (as described above). In some embodiments, the detection agents comprise one or more label moiety(ies). In embodiments employing two or more label moieties, each label moiety can be the same, or some, or all, of the label moieties may differ.

In one embodiment, the detection agent is used as a secondary reagent. For example, in one embodiment, the detection agent is designed to bind a first molecule that is introduced to bind to the analyte and/or standard, or the complex of the first molecule with the analyte and/or standard. For example, in one embodiment, a "primary" monoclonal or polyclonal antibody is first introduced into the capillary tube comprising the immobilized sample. This "primary" antibody binds to the analyte of interest (if present in the sample) and unbound primary antibodies are washed away. Next, a "secondary" antibody is introduced, which is designed to bind either the primary antibody, or a region spanning the primary antibody-analyte complex. The secondary antibody includes a label moiety for detecting and/or visualizing the presence/absence of the analyte of interest.

In one embodiment, a multiplex immunoassay is carried out in the apparatuses and systems provided herein, to detect the presence or absence of two or more analytes of interest (for example, two, three, four or five analytes) in the sample, or to quantify the amount of two or more analytes in the sample. In a further embodiment, the detection agent is the same for each of the analytes of interest. For example, the detection agent for each analyte is a secondary antibody conjugated to a chemiluminescent label such as horseradish peroxidase. Differentiation between the analytes occurs by initially introducing distinct primary antibodies into the capillary tube, where each primary antibody is specific for a unique analyte of interest.

The label moiety, conjugated to the secondary antibody, can be any suitable label. For example, general labels can include optical dyes (e.g., colored or fluorescent dyes); chemiluminescent labels, phosphorescent labels, enzymatic labels (e.g., alkaline phosphatase and/or horseradish peroxidase), bioluminescent labels, isotopic labels (e.g., radioactive isotopes or heavy isotopes), mass labels, and/or particle labels (e.g., colloids, magnetic particles, etc). In one embodiment, the label moiety is a chemiluminescent moiety. In a further embodiment, the chemiluminescent moiety is horseradish peroxidase (HRP). In one embodiment, the HRP is conjugated to a secondary antibody, and is used in an immunoassay to detect an analyte or a plurality of analytes in a sample. In some embodiments, a label moiety can be a single isomer dye. In some embodiments, the label moiety can be a fluorescent dye that can include any entity that provides a fluorescent signal. For example, a fluorescent dye can include a resonance-delocalized system or aromatic ring system that absorbs light at a first wavelength and emits fluorescent light at a second wavelength in response to the absorption event. A fluorescent dye can be any of a variety of classes of fluorescent compounds, for example, xanthenes, rhodamines, fluoresceins, cyanines, phthalocyanines, squaraines, bodipy dyes, coumarins, oxazines, and carbopyronines. In some embodiments, the fluorescent dye is 5-carboxytetramethylrhodamine (5-TAMRA), and/or any other suitable class of fluorescent compound.

In some embodiments, the label moiety can be and/or can include a chemiluminescent label. Suitable labels moieties can include enzymes capable of reacting with a chemiluminescent substrate in such a way that photon emission by chemiluminescence is induced. For example, enzymes can induce chemiluminescence in other molecules through enzymatic activity. Such enzymes can be and/or can include peroxidase, for example, horseradish peroxidase (HRP), β-galactosidase, phosphatase, etc. In some embodiments, the chemiluminescent label can be selected from any of a variety of classes of luminol label, an isoluminol label, etc. In some embodiments, a detection agent can include chemiluminescent-labeled antibodies, for example, a secondary antibody covalently bound to HRP. In some embodiments, the detection agents comprise chemiluminescent substrates such as, for example, Galacton substrate available from Applied Biosystems of Foster City, California or SuperSignal West Femto Maximum Sensitivity substrate available from Pierce Biotechnology, Inc. of Rockford, Illinois, or any other suitable substrates. In some embodiments, a detection agent can be any of those described in U.S. Pat. Nos. 6,689,576, 6,395,503, 6,087,188, 6,287,767, 6,165,800, and 6,126,870 the disclosures of which are incorporated herein by reference in their entireties.

In some embodiments, the label moiety can be and/or can include a bioluminescent compound (e.g., found in biological systems in which a catalytic protein increases the efficiency of the chemiluminescent reaction). The presence of a bioluminescent compound is determined by detecting the presence of luminescence. Suitable bioluminescent compounds include, but are not limited to luciferin, luciferase and aequorin.

In one embodiment, the label moiety can be and/or can include a fluorescent dye. Such fluorescent dyes can include a resonance-delocalized system or aromatic ring system that absorbs light at a first wavelength and emits fluorescent light at a second wavelength in response to the absorption event. Fluorescent dyes can be any of a variety of classes of fluorescent compounds such as but not limited to xanthenes, rhodamines, fluoresceins, cyanines, phthalocyanines, squaraines, bodipy dyes, coumarins, oxazines, and carbopyronines. In some embodiments, for example, where detection agents contain fluorophores, such as fluorescent dyes, their fluorescence is detected by exciting them with an appropriate light source, and monitoring their fluorescence by a detector sensitive to their characteristic fluorescence emission wavelength.

As provided above, in one embodiment, two or more different agents can be used to bind to or interact with two or more different analytes to enable more than one type of analytes to be detected simultaneously. In some embodiments, two or more different detection agents, which bind to or interact with the one analyte, can be detected simultaneously. In various embodiments, using two or more different detection agents, one agent, for example a first primary antibody, can bind to or interact with one or more analytes to form a first agent-analyte complex, and a second reagent, the detection agent, for example a secondary antibody, can be used to bind to or interact with the first agent-analyte complex.

In another embodiment, two different detection agents, for example antibodies for both phospho- and non-phospho-forms of analyte of interest can enable detection of both forms of the analyte of interest. In some embodiments, a single specific detection agent, for example an antibody, can allow detection and analysis of both phosphorylated and non-phosphorylated forms of an analyte. In some embodiments, multiple detection agents can be used with multiple substrates to provide color multiplexing. For example, different chemiluminescent substrates can be used to emit photons of differing color. Selective detection of different colors (e.g., via a diffraction grating, a prism(s), a series of colored filters, and/or the like) can allow determination of which color photons are being emitted at any position along a fluid path (e.g., along a size gradient), and therefore determination of which detection agents are present at each emitting location. In some embodiments, different chemiluminescent reagents can be supplied sequentially, allowing different bound detection agents to be detected sequentially.

In general, during the standard immunoassay process carried out in the apparatuses and systems described herein, a portion of the internal standard will be lost due to the various wash processes. Thus, it is generally desirable to load a sufficient amount of internal standard in the sample at the beginning of the assay so that enough signal can be generated by the internal standard that remains in the capillary after the immunoassay to provide coordination to calibrate the curve and analyze the size and/or identity (e.g., amino acid number or number of oligonucleotide base pairs) of the analyte. A relatively large amount of internal standard, however, may interfere with the capture of the analyte if the standard and the analyte are located in the same position. As such, some standards do not locate with the analyte during and/or at the end of the electrophoresis. Such a standard, however, may not produce a reliable calibration curve for the detection of the analyte. Therefore, in some embodiments, a sample can include more than one standard. For example, an internal standard can be formed by and/or include a first standard (referred to as a "bright standard" or a "registration standard") and a second standard (referred to as a "dim standard"). The bright standard can be a standard that has characteristics (such as a molecular weight range or specific molecular weight) that differs from that of the analyte. As such, after electrophoresis, the location of registration standard and the analyte are located apart from each other in the capillary. Thus, the fluorescence emitted from the bright standard and the analyte will not overlap and interfere with each other. The dim standard can be a standard that has characteristics (such as a molecular weight range or specific molecular weight) that are similar to that of the analyte. As such, after electrophoresis, the location of the registration standard and the analyte are located close to each other in the capillary.

The bright standard can locate at a position along a flow path (e.g., defined by a capillary or the like) that is different from the position of the analyte and provides a coordinate (e.g., an anchor point) for the dim standard to locate close to or at the same position as the analyte, thereby providing an accurate calibration curve. Generally, the bright standard produces a fluorescence that is brighter than the fluorescence emitted by the dim standard after the internal standard and the analyte have been separated and immobilized. The difference of the brightness between the bright standard and dim standard can be attributed to the difference in the nature of emission and/or to the difference in the amounts of the two standards contained in the internal standard. For example, a large quantity of bright standard and a small quantity of dim standard can be mixed to form a standard that can produce a "bright" signal from the bright standard and a "dim" signal from the dim standard. Thus, a "bright" signal due to the bright standard and a "dim" signal due to the dim signal are detected after the separation step by electrophoresis. In some embodiments, an internal standard can include a bright standard and a dim standard such as, for example, those described in U.S. Patent Application Publication No. 2011/0011740, the disclosure of which is incorporated herein by reference in its entirety.

The embodiments described herein can be used in conjunction with any of the chemistries and/or methods described above. For example, FIG. 1 is a schematic illustration of a portion of a capillary electrophoresis system 100 according to an embodiment. The capillary electrophoresis system 100 (also referred to herein as "system") is configured to facilitate analysis of a target analyte in a single system and to provide the functionality of both pipettes and fluid paths, thereby enabling the analysis of very small volume samples. The system 100 can include any suitable device, mechanism, assembly, subassembly, electronic device, actuator, and/or the like (not shown in FIG. 1) that enable the system 100 to, for example, separate, immobilize, and detect any suitable target analyte.

As shown in FIG. 1, the system 100 can be configured to receive and/or include a cartridge 150. The cartridge 150 includes a body portion 151 that is fixedly coupled to a set of substantially flexible capillaries 153. The body portion 151 of the cartridge 150 defines a reservoir 152. More specifically, the body portion 151 is arranged such that the set of capillaries 153 coupled thereto are in fluid communication with the reservoir 152. For example, in some embodiments, the body portion 151 can be substantially hollow, defining the reservoir 152 between a set of walls (not shown in FIG. 1). Similarly stated, the body portion 151 can be bounded by a set of walls that extend from a base (not shown in FIG. 1) to define the reservoir 152 while allowing at least one side of the body portion 151 to remain substantially open (e.g., the body portion 151 can have or define a substantially U-shaped cross-section). As described in further detail herein, at least a part of the body portion 151 can be electrically conductive. In other words, at least a part of the body portion 151 can be formed from electrically conductive plastic or an electrically conductive polymer. In some embodiments, the electrically conductive plastic includes carbon-infused plastic. In other embodiments, the electrically conductive plastic includes stainless steel-infused plastic, carbon nanotube-infused plastic, etc.

In some embodiments, the microplate plastic has a resistivity (volume) of <25 ohm·cm and (surface) of 1e3-1e5 ohm, and the cartridge top is (volume)<1e3 ohm·cm, (surface)<1e6 ohm.

The set of twenty five capillaries has a total resistivity of 1-2 Mohm. In some embodiments, the resistance of the microwell plate, for example, is at least 2 orders of magnitude below that (i.e., 20 k·ohm or less) of the capillaries. In some embodiments, the resistivity is lower. For example, in an embodiment having a 100 capillary cartridge, the total resistivity would be 25 percent, or, 250-500 k·ohm. In other embodiments, the resistivity of the microwell plate is higher.

If the resistance of the electrically conductive components is higher than some threshold (e.g., 100 times less than that of the capillaries), there is a voltage drop across the electrically conductive components and higher voltage from the power supply is required to reach the same voltage in the capillaries. Said another way, Vpower supply=V capillaries+ Velectrically conductive components.

The set of capillaries 153 can be any suitable arrangement. For example, while the cartridge 150 is shown in FIG. 1 as including a set of seven individual capillaries 153, in other embodiments, a cartridge can include any number of individual capillaries. For example, in some embodiments, a cartridge can include less than seven individual capillaries or more than seven individual capillaries. In some embodiments, a cartridge can include 25 individual capillaries or more. The capillaries 153 define a lumen (not shown in FIG. 1) that can be configured to receive at least a portion of a sample, solution, reagent, analyte, and/or any other suitable fluid or gel, as described in further detail herein.

The capillaries 153 can be any suitable shape, size, or configuration and can be formed from any suitable material (e.g., glass, plastic, silicon, fused silica, gel, PYREX™ (amorphous glass), and/or the like) that allows a liquid and/or dissolved molecules to flow. In some embodiments, the length of the capillaries 153 can be based at least in part on factors such as sample size and the extent of sample separation required to resolve the analyte or analytes of interest. In some embodiments, the capillaries 153 can have a length of about 2 to 20 centimeters (cm). In some embodiments, the capillaries 153 can have a length of less than 2 cm. In some embodiments, the capillaries 153 can have a length of about 3 cm, 4 cm, 5 cm, or 6 cm, or more. In some embodiments, the use of longer capillaries 153 can result in better separation of samples and improved resolution of complex mixtures and/or when resolving a low abundance of analytes. In some embodiments, the capillaries can have a smaller internal diameter.

In some embodiments, the capillaries 153 can be substantially cylindrical, having any suitable length and any suitable diameter. Accordingly, the shape and/or size of the lumen defined by the capillaries 153 can substantially correspond with the shape and/or size of the capillaries 153. For example, in some embodiments, the capillaries 153 can define a lumen having a diameter of about 10 micrometers (μm) to about 1000 μm. In other embodiments, a cartridge can include capillaries that define a lumen having a diameter of about 25 μm to about 400 μm. The size of the diameter of the lumen can be based at least in part on the sample and/or the sample volume. For example, a lumen with a relatively small diameter uses a relatively low sample volume, which can be suitable for expensive samples or reagents, whiles a lumen with a relatively large diameter uses a relatively high sample volume and can result in improved signal detection.

In some embodiments, the capillaries 153 can be have a cross-sectional shape that is substantially rounded (e.g., circular, elliptical, oblong, etc.) or substantially polygonal (e.g., trapezoidal, rectangular, square, pentagonal, octagonal, etc.). In some embodiments, a cartridge can include a set of capillaries that can extend from a body portion in a curvilinear path (e.g., curved, rounded, serpentine, and/or the like).

As shown in FIG. 1, the body portion 151 is coupled to a connector 158 that is in fluid communication with the reservoir 152 defined by the body portion 151 and a vacuum source 160. The connector 158 can be any suitable device. For example, in some embodiments, the connector 158 can be a cap or the like that can be coupled to the body portion 151 to substantially close the body portion 151. Moreover, the connector 158 can include a port, an opening, an aperture, and/or the like that can be operable in placing the reservoir 152 in fluid communication with the vacuum source 160. The vacuum source 160 can be any suitable device or mechanism that is configured to produce a negative pressure within a volume, thereby applying a suction force to at least a portion of the volume. For example, in some embodiments, the vacuum source 160 can be a vacuum chamber that is fluidically coupled to an impeller or the like. In this manner, the impeller can be rotated (e.g., by an electric motor) to produce a negative pressure within the vacuum chamber. Thus, with the vacuum source 160 in fluid communication with the connector 158 and with the connector 158 in fluid communication with the reservoir 152, the vacuum source 160 can produce a negative pressure within the reservoir 152. Furthermore, with the capillaries 153 in fluid communication with the reservoir 152, the negative pressure produces a suction force through the lumen defined by the capillaries 153.

As described above, the system 100 can be configured to separate, immobilize, and analyze a sample in an at least partially automated process. For example, although not shown in FIG. 1, in some embodiments, the system 100 can include a cartridge retainer or the like that can receive at least a portion of the cartridge 153 and can include a reagent tray holder that can receive at least a portion of a reagent tray. The reagent tray holder and reagent tray, in one embodiment includes capillary electrophoresis reagents such as a separation matrix, a primary antibody for an analyte of interest and a secondary antibody conjugated to HRP. In this manner, the cartridge retainer can move relative to the reagent holder to place the capillaries 153 of the cartridge 150 in fluid communication with one or more wells defined by the reagent tray. With the vacuum source 160 being in fluid communication with the capillaries 153 a suction force can be exerted through the capillaries 153 to selectively draw one or more reagents, samples, buffers, washes, detectors, analyte, ampholytes, and/or the like into the lumen defined by the capillaries 153. In some embodiments, the reagent tray, or a portion of the reagent tray, is electrically conductive.

Once a mixture (e.g., a sample) having desired constituents is drawn into the lumen defined by the capillaries 153, the system 100 can apply an electric field to the electrically conductive part of the body portion 151 of the cartridge 150. For example, although not shown in FIG. 1, in some embodiments, the system 100 can include an electronic system that includes at least a power source and a means for activation (e.g., a manual switch or an electronic switch included in an electronic circuit and operably coupled to at least a memory and a processor). In such embodiments, the power source can be activated to supply a flow of electric current (e.g., though a wire or other suitable circuit) to the electrically conductive part of the body portion 151. Moreover, the arrangement of the cartridge 150 can be such that the set of capillaries 153 are in electrical contact with the electrically conductive part of the body portion 151. Thus, when the power source is activated, electrical current can flow to the set of capillaries 153 to perform, for example, electrophoresis on the sample disposed therein. More particularly, the flow of electrical current to the capillaries 153 can initiate capillary electrophoresis, wherein analytes in the sample disposed within the capillaries 153 are separated along a size gradient (e.g., along a length of each capillary 153). Thus, negatively molecules (e.g., analytes or the like) will migrate through the size gradient.

Once the molecules are sufficiently separated, the system 100 can be configured to immobilize the molecules within the capillaries 153. For example, in some embodiments, the system 100 can include a light source such as a UV lamp or the like (not shown in FIG. 1) that can be positioned (e.g., at least semi-automatically) relative to the cartridge 150. In this manner, the light source can be activated (e.g., switched on by supplying electric current to the light source via, for example, the power source described above), thereby emitting photons that can interact with at least a portion of the separated sample disposed in the capillaries 153. As described in detail above, the interaction of the separated sample with the photons emitted by the light source can be such that the at least a portion of the separated sample binds to the walls of the capillaries 153 to become immobilized.

With the analytes separated and immobilized, the immobilized analytes and/or standards included in the sample are probed with a detection agent (e.g., any suitable agent, reagent, analyte-specific antibody, horseradish peroxidase (HRP)-conjugated secondary antibody, and/or the like or any combination thereof, as described in detail above). The detection reagent is then used to create a signal from one or more label moieties (e.g., HRP, isotopic labels, immune labels, optical dyes, enzymes, particles or combination of particles such as chemiluminescent-labeled antibodies, fluorescent-labeled antibodies, and/or the like) that can be detected by an imaging device included in the system 100 (not shown in FIG. 1) and graphed as signal vs. length of the capillary 153 within which the sample is disposed. For example, in some embodiments, the system 100 can include a photodetector, an array of photodetectors, a charged coupled device (CCD) array, and/or the like that can be used to continuously monitor, in real time, the signal emitted by the analyte and/or the standard to allow a user to rapidly determine whether an analyte is present in the sample, and optionally, the amount or activity of the analyte. In some embodiments, the signal can be measured from at least two different time points. In some embodiments, the signal can be monitored continuously or at several selected time points. Alternatively, the signal can be measured at an end-point, in which a signal is measured after a certain amount of time, and the signal is compared against a control signal (sample without analyte), threshold signal, or standard curve. In addition, the signal from a standard can be used to interpret the signal from the analyte. In some embodiments, a signal from the analyte and/or the standard can be at least 2-fold greater than the background. In some embodiments, a signal between 2 to 10-fold greater than the background can be generated. In some embodiments, a signal can be 10-fold or greater than the background.

Figure 2:
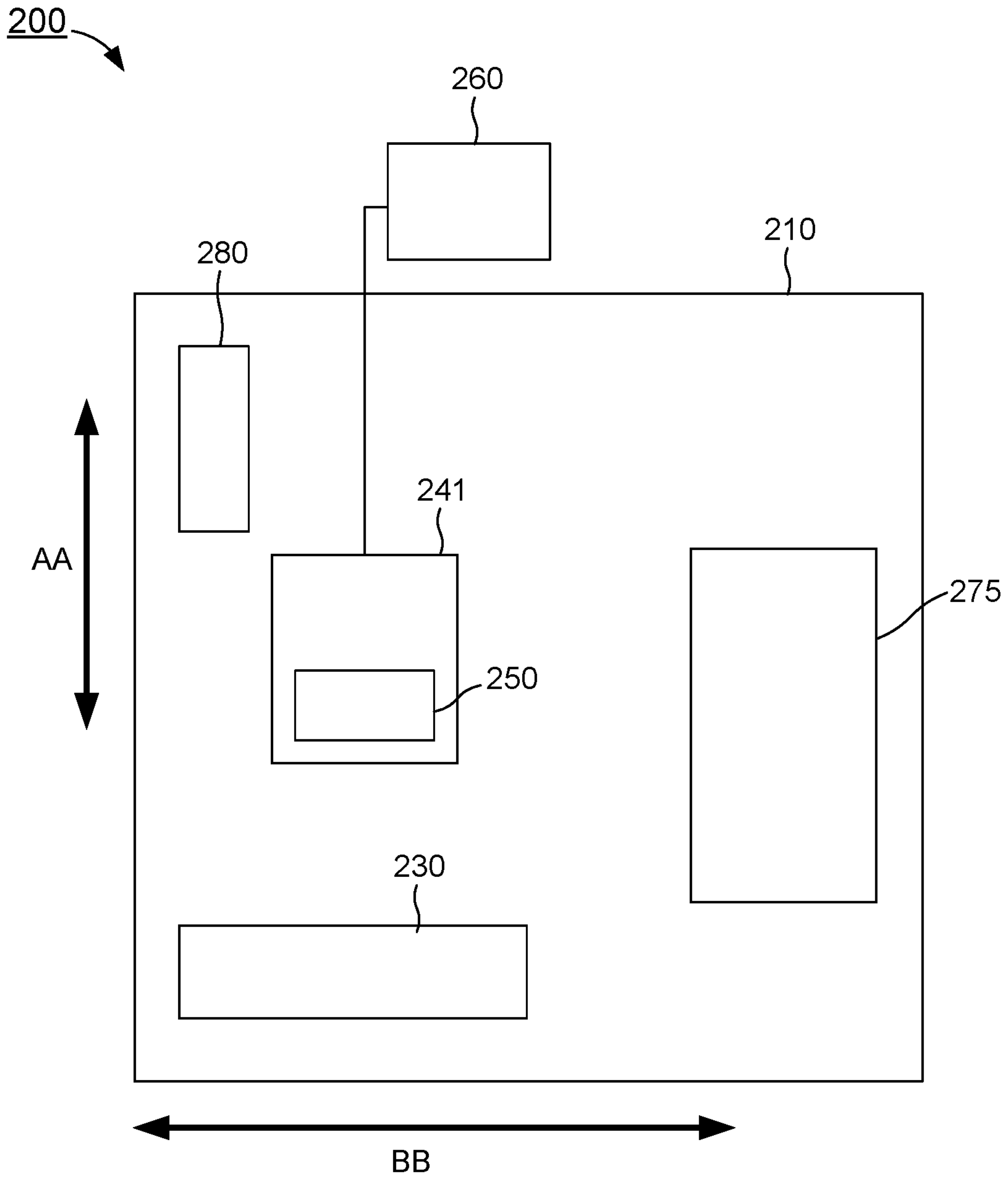
FIG. 2 is a schematic illustration of capillary electrophoresis system according to an embodiment.

Referring to FIG. 2, a capillary electrophoresis system 200 is illustrated according to an embodiment. The capillary electrophoresis system 200 (also referred to herein as "system") can be substantially similar in at least function to the system 100 described above with reference to FIG. 1. The system 200 can be configured to perform at least a semi-automated immunoassay of a sample using electrophoresis and, more particularly, capillary electrophoresis. Therefore, as described in further detail herein, the system 200 can be configured to at least semi-automatically draw a sample (e.g., including any suitable agent, reagent, protein, analyte, buffer, lysate, etc.) into a set of capillaries, separate the sample, immobilize at least some of the constituents of the sample (e.g., via heat, UV exposure, and/or the like), and detect the presence or the absence of a target analyte.

The system 200 includes a housing 210, a reagent tray holder 230, a capillary cartridge retainer 241, a vacuum source 260, a light source 280, and an optical detector 275. Although not shown in FIG. 2, in some embodiments, the system 200 can include any suitable electronic system or assembly with at least a power source, a processor, and a memory that can be configured and/or otherwise programmed to perform one or more processes (e.g., hardware module and/or software module stored in the memory and executed in the processor) associated with performing at least a semi-automatic immunoassay.

The housing 210 of the system 200 can be any suitable shape, size, or configuration and can be arranged to at least partially enclose or at least partially house any suitable component of the system 200. For example, the housing 210 can at least partially enclose the reagent tray holder 230, the capillary cartridge retainer 241, the light source 280 and the optical detector 275. Although not shown in FIG. 2, in some embodiments, the housing 210 can be configured to form one or more portions, chambers, inner volumes, etc. that are configured to allow the at least some of the components of the system 200 to be disposed therein, as described in further detail herein.

The capillary cartridge retainer 241 (also referred to herein as "cartridge retainer") can be any suitable shape, size, or configuration and can be arranged to receive at least a portion of a capillary cartridge 250 (also referred to herein as "cartridge"). For example, in some embodiments, the cartridge retainer 241 can have or define a substantially C-shaped cross-section with at least one side of the cartridge retainer 241 being substantially open to receive at least a portion of the cartridge 250. The cartridge retainer 241 can be movably disposed within and/or movably coupled to the housing 210. For example, the cartridge retainer 241 can be movably coupled to a track, rack, lead screw, slide, piston, and/or the like that can be operable in moving the cartridge retainer 241 relative to the housing 210, as indicated by the arrow AA in FIG. 2. More particularly, in some embodiments, the cartridge retainer 241 can be disposed within the housing 210 and arranged for a substantially vertical movement (e.g., up and down) relative to the housing 210 while a substantially horizontal movement (e.g., left or right and/or at any other angle other than 90° relative to a horizontal axis) relative to the housing 210 is limited. For example, in some embodiments, the cartridge retainer 241 can be movably coupled to a portion of the housing 210 and operably coupled to an electric motor (not shown in FIG. 2) that can be activated to move the cartridge retainer 241 relative to the housing 210 along a single axis (e.g., by rotating a lead screw or the like).

As described above, the cartridge retainer 241 can receive at least portion of the cartridge 250 and can at least temporarily retain the cartridge 250 to limit its movement. For example, in some embodiments, the cartridge 250 can be at least temporarily coupled to the cartridge retainer 241 such that the position of the cartridge 250 relative to the cartridge retainer 241 is substantially fixed. In some embodiments, the cartridge retainer 241 can form a friction fit, a snap fit, a threaded coupling, and/or the like with the cartridge 250 when the cartridge 250 is coupled thereto. In some embodiments, the arrangement of the cartridge retainer 241 and/or the cartridge 250 can be such that the cartridge 250 is in a predetermined orientation relative to the cartridge retainer 241. Similarly stated, the cartridge retainer 241 can be configured to receive the cartridge 250 in a single, predetermined orientation.

The cartridge 250 can be any suitable shape, size, or configuration. For example, the cartridge 250 can include a body portion or the like (not shown in FIG. 2) that is fixedly coupled to a set of capillaries (not shown in FIG. 2). Although not shown in FIG. 2, the body portion of the cartridge 250 can define a reservoir that is in fluid communication with the set of capillaries. In some embodiments, the cartridge 250 can be substantially similar to or the same as the cartridge 150 described above with reference to FIG. 1. Therefore, portions of the cartridge 250 are not described in further detail herein and should be considered substantially similar to corresponding portions of the cartridge 150 described above.

As shown in FIG. 2, the vacuum source 260 is coupled to the cartridge retainer 241. The vacuum source 260 can be any suitable device, mechanism, and/or assembly that is configured to produce a negative pressure within a volume. For example, although not shown in FIG. 2, in some embodiments, the vacuum source 260 can include a vacuum chamber that is in fluid communication with an impeller. The impeller can be coupled to a motor that is configured to rotate the impeller to produce a negative pressure within the vacuum chamber. Moreover, the vacuum source 260 can be coupled to the cartridge retainer 241 such that, when the cartridge 250 is retained by the cartridge retainer 241, the vacuum source 260 can be placed in fluid communication with the cartridge 250. In this manner, the vacuum source 260 can be activated (e.g., by a manual switch and/or by an electrical switch included in an electrical circuit and controlled by a processor) to produce a negative pressure within the cartridge 250, as described in detail above with reference to the vacuum source 160 of FIG. 1. Although not shown in FIG. 2, in some embodiments, the system 200 can include an actuator or the like that can be operable in selectively placing the vacuum source 260 in fluid communication with the cartridge 250. For example, in some embodiments, an engagement portion of the vacuum source 260 can be moved relative to the cartridge 250 to place the vacuum source 260 in fluid communication with the cartridge 250 or to remove the vacuum source 260 from fluid communication with the cartridge 250. In some embodiments, the impeller is configured to prevent siphoning of fluid from the cartridge.

The reagent tray holder 230 of the system 200 can be any suitable shape, size, or configuration and can be arranged to receive at least a portion of a reagent tray (not shown in FIG. 2). For example, in some embodiments, the reagent tray holder 230 can include a portion that defines a recess and/or a portion that is otherwise bounded, at least partially, by a set of walls. As described above with reference to the cartridge retainer 241, the reagent tray holder 230 can be movably disposed within and/or movably coupled to the housing 210. For example, the reagent tray holder 230 can be movably coupled to a track, rack, lead screw, slide, piston, and/or the like that can be operably in moving the reagent tray holder 230 relative to the housing 210, as indicated by the arrow BB in FIG. 2. More particularly, the reagent tray holder 230 can be at least partially disposed within the housing 210 and arranged to move in a direction that is substantially perpendicular (e.g., normal) to the cartridge retainer 241. In other words, the cartridge retainer 241 can be moved in a substantially vertical direction (as described above) and the reagent tray holder 230 can be moved in a substantially horizontal direction (e.g., left to right, front to back, and/or a combination thereof).

As described above, the reagent tray holder 230 can receive at least a portion of the reagent tray (not shown in FIG. 2) and can at least temporarily retain (e.g., hold) the reagent tray to limit its movement. The reagent tray can be any suitable tray or the like. For example, in some embodiments, the reagent tray can hold and/or otherwise define a set of well plates, microwell plates, and/or the like. In some embodiments, the reagent tray can include a set of 96 microwells that are spaced at about 9 millimeter (mm) center-to-center spacing. In other embodiments, a reagent tray can include a set of 384 microwells that are spaced at about 4.5 mm center-to-center spacing. In other embodiments, a reagent tray can include a set of microwells and/or troughs that are spaced about 3 mm center-to-center spacing. Although specific examples of reagent trays are described, the reagent tray holder 230 can be configured to receive any suitable reagent tray of similar size and/or shape that can define any number and/or any arrangement of wells and/or microwells. As such, the wells and/or microwells included in or defined by the reagent tray can receive any suitable solution, fluid, gel, lysate, buffer, sample, analyte, ampholyte, agent, reagent, protein, matrix, and/or the like. In some embodiments, the reagent tray, or a portion of the reagent tray (e.g., a well or row(s) of wells), is electrically conductive and can act as an electrical connection through its coupling to the reagent tray holder 230. In some embodiments, the reagent tray holder 230 is electrically conductive.

In some instances, the cartridge retainer 241 and the cartridge 250 coupled thereto can move relative to the reagent tray holder 230 to dispose at least a portion of the cartridge 250 (e.g., an end portion of the capillaries included in the cartridge 250) in the wells or microwells of the reagent tray. In addition, the reagent tray holder 230 can be moved relative to the cartridge retainer 241 and the cartridge 250 to selectively position a set of wells relative to the cartridge 250. For example, the reagent tray holder 230 can be in a first position relative to the cartridge retainer 241 and the cartridge retainer 241 can be in a first position relative to the reagent tray holder 230 to place an end portion of the capillaries (not shown in FIG. 2) of the cartridge 250 in a first set of wells defined by the reagent tray. In some instances, the cartridge retainer 241 can be moved to a second position relative to the reagent tray holder 230 to remove the capillaries of the cartridge 250 from the wells of the reagent tray. In some instances, the reagent tray holder 230 can then be moved to a second position relative to the cartridge retainer 241 and the cartridge retainer can again be placed in the first position relative to the reagent tray holder 230 to place the end portion of the capillaries of the cartridge 250 in a second set of wells. Thus, the cartridge retainer 241 and the reagent tray holder 230 can be moved in a predetermined and related manner to place the capillaries of the cartridge 250 in any suitable microwell or set of microwells defined by the reagent tray.

The light source 280 of the system 200 can be any suitable device, member, mechanism, assembly, and/or the like that is configured to release energy (e.g., heat, photons, radiation, etc.). For example, in some embodiments, the light source 280 can be a UV grid lamp. In this manner, the light source 280 can include an element that can be excited (e.g., powered) to emit photons. By way of example, the light source 280 can be a low-pressure mercury lamp that generates light (e.g., photons) at a first wavelength of about 254 nm. In some embodiments, the light source 280 can include a phosphor coating to convert the first wavelength of about 254 nm to a second wavelength of about 295 nm. In this manner, the light source 280 can emit energy that can interact with at least a portion of a sample contained within the capillaries of the cartridge 250. Although not shown in FIG. 2, the light source 280 can be disposed, at least partially, in one or more covers that are configured to block, limit, or otherwise direct light emitted from the light source 280.

The light source 280 can be movably disposed within and/or movably coupled to the housing 210. For example, the light source 280 can be movably coupled to a track, rack, lead screw, slide, piston, and/or the like that can be operable in moving the light source 280 relative to the housing 210, as indicated by the arrow AA in FIG. 2. Although shown in FIG. 2 as moving in the same direction (e.g., parallel) as the cartridge retainer 241, in other embodiments, the light source 280 can move in a direction that is substantially perpendicular to the cartridge retainer 241. In some embodiments, the light source 280 can be moved in a direction that is perpendicular (e.g., normal) to the cartridge retainer 241 and the reagent tray holder 230 (e.g., the light source 280 can move along an X-axis of an orthogonal coordinate system, the reagent tray holder 230 can move along a Y-axis of the orthogonal coordinate system, and the cartridge retainer 241 can move along a Z-axis of the orthogonal coordinate system). Moreover, the light source 280 can be arranged relative to the housing 210 as to be disposed on a first side of the cartridge retainer 241, as described in further detail herein.

The optical detector 275 of the system 200 can be disposed, at least partially, within the housing 210. More specifically, the optical detector 275 can be arranged relative to the housing 210 as to be disposed on a second side (opposite the first side) of the cartridge retainer 241. Furthermore, with the movement of the cartridge retainer 241 limited to a substantially vertical direction, a lateral distance between the optical detector 275 and the cartridge retainer 241 is substantially constant.

The optical detector 275 can be any suitable device, mechanism, and/or assembly that is configured to detect a signal emitted by, for example, an analyte and/or a standard (described above). For example, in some embodiments, the optical detector 275 can include a photodetector, an array of photodetectors, a charged coupled device (CCD) array, and/or the like that can be used to continuously monitor, in real time, the signal emitted by the analyte and/or the standard to allow a user to rapidly determine whether an analyte is present in the sample, and optionally, the amount or activity of the analyte. In some embodiments, the optical detector 275 can include any suitable lens and/or filter (e.g., a TAMRA filter) that is associated with the signal (e.g., chemiluminescence, fluorescence, and/or the like). Moreover, the optical detector 275 can be operably coupled to any suitable electrical or electronic circuit to receive a signal from and/or to send a signal to a processor or the like.

As described above, the system 200 can be configured to separate, immobilize, and analyze a sample in at least a semi-automated process. For example, in some instances, a user can prepare a reagent tray (not shown in FIG. 2) that defines any number of wells or microwells containing a sample, protein, buffer, lysate, standard, and/or etc. In this manner, the reagent tray holder 230 can be moved relative to the housing 210 to receive the prepared reagent tray and, once loaded, the reagent tray holder 230 can be moved (e.g., by a motor or the like that is operably coupled to an electronic system having at least a processor and a memory) to a first position.

With the reagent tray holder 230 in the first position, the cartridge retainer 241 can be moved relative to the reagent holder 230 to place the capillaries of the cartridge 250 in fluid communication with one or more wells defined by the reagent tray. With the vacuum source 260 being in fluid communication with the cartridge 250 (as described above) a suction force can be exerted through the capillaries to selectively draw one or more reagents, samples, buffers, washes, detectors, analytes, ampholytes, antibodies, labels, and/or the like into lumen defined by the capillaries. As described above, the cartridge retainer 241 and the reagent tray holder 230 can be moved in a related manner to selectively place the capillaries of the cartridge 250 in a desired set of wells or microwells defined by the reagent tray. Thus, a sample having a desired set of constituents can be drawn into the capillaries of the cartridge 250.

Once a mixture (e.g., a sample such as a purified protein) having desired constituents is drawn into the lumen defined by the capillaries of the cartridge 250, the system 200 can apply an electric field to an electrically conductive portion of the cartridge 250 (as described above with reference to the system 100 of FIG. 1). Thus, electrical current can flow to the set of capillaries of the cartridge 250 to perform, for example, electrophoresis on the sample disposed therein. More particularly, the flow of electrical current to the capillaries can initiate capillary electrophoresis, wherein analytes in the sample disposed within the capillaries of the cartridge 250 are separated along a size gradient (e.g., along a length of each capillary), as described in detail above. Thus, molecules will migrate according to their size.

Once the molecules are sufficiently separated, the system 200 can be configured to immobilize the molecules within the capillaries of the cartridge 250. For example, the light source 280 (e.g., a UV light source) can be moved from a first position to a second position relative to the cartridge 250. In this manner, the light source 280 can be activated (e.g., switched on by supplying electric current to the light source via, for example, the power source described above), thereby emitting photons that can interact with at least a portion of the separated sample disposed in the capillaries of the cartridge 250. The interaction of the separated sample with the photons emitted by the light source 280 can be such that the at least a portion of the separated sample binds to the walls of the capillaries 253 to become immobilized, as described in detail above.

With the sample components (e.g., comprising the analyte(s)) separated and immobilized, the immobilized analyte(s) and/or standard(s) included in the sample are probed with one or more reagents comprising a detection agent (e.g., any suitable agent, reagent, analyte-specific antibody, horseradish peroxidase (HRP)-conjugated secondary antibody, and/or the like or any combination thereof, as described in detail above). The detection reagent is then used to create a signal from one or more label moieties (e.g., isotopic labels, immune labels, optical dyes, enzymes, particles or combination of particles such as chemiluminescent-labeled antibodies, fluorescent-labeled antibodies, and/or the like) that can be detected by the optical detector 275 and graphed as signal vs. length of the capillary of the cartridge 250. In some embodiments, the signal can be measured from at least two different time points. In some embodiments, the signal can be monitored continuously or at several selected time points. Alternatively, the signal can be measured at an end-point, in which a signal is measured after a certain amount of time, and the signal is compared against a control signal (sample without analyte), threshold signal, or standard curve. In addition, the signal from a standard can be used to interpret the signal from the analyte. In some embodiments, a signal from the analyte and/or the standard can be at least 2-fold greater than the background. In some embodiments, a signal between 2 to 20-fold greater than the background can be generated. In some embodiments, a signal can be 20-fold or greater than the background.

Figure 3:
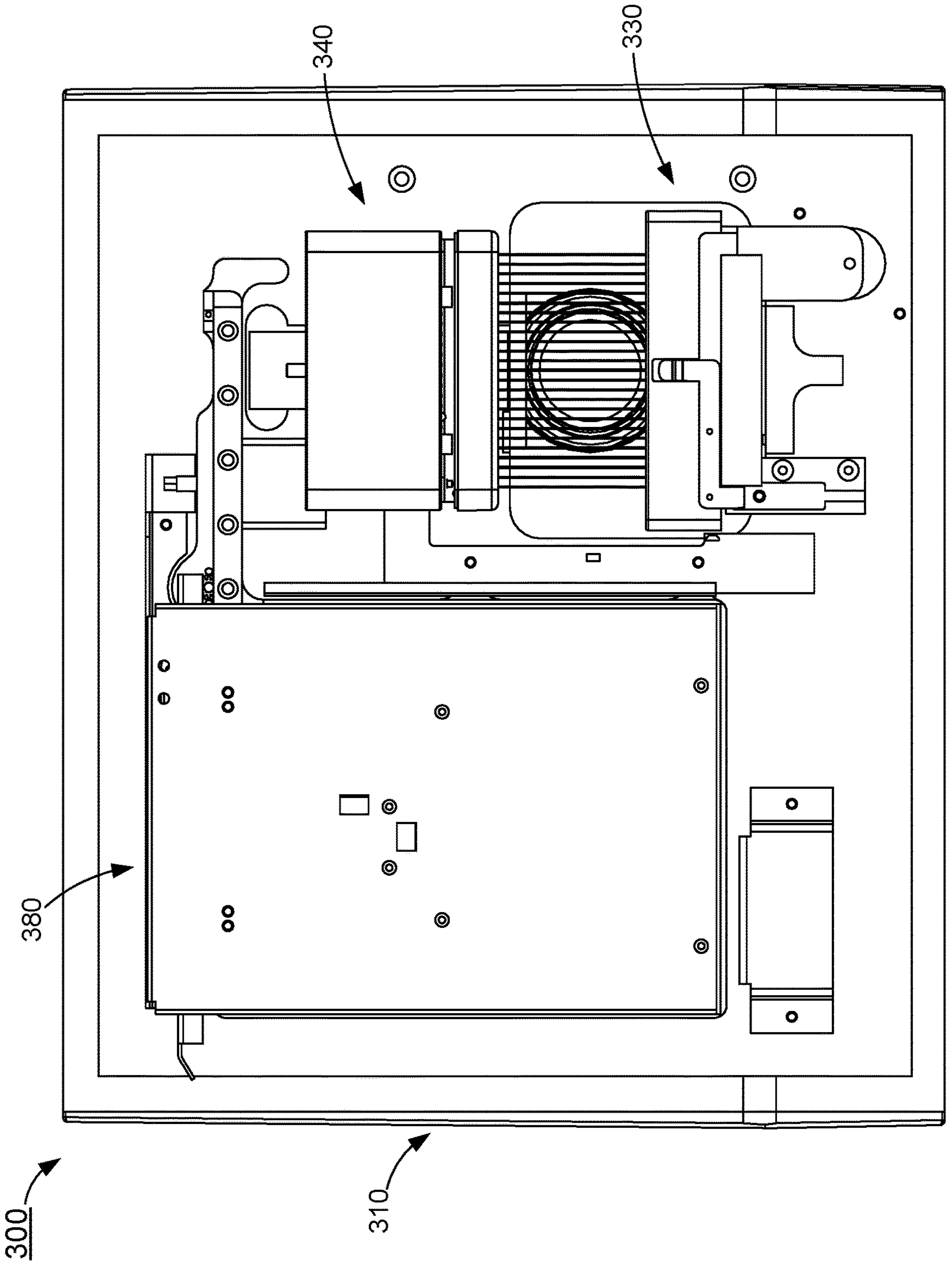
FIGS. 3-5 are a front view, a left perspective view, and a right perspective view, respectively, of a capillary electrophoresis system according to an embodiment.
Figure 4:
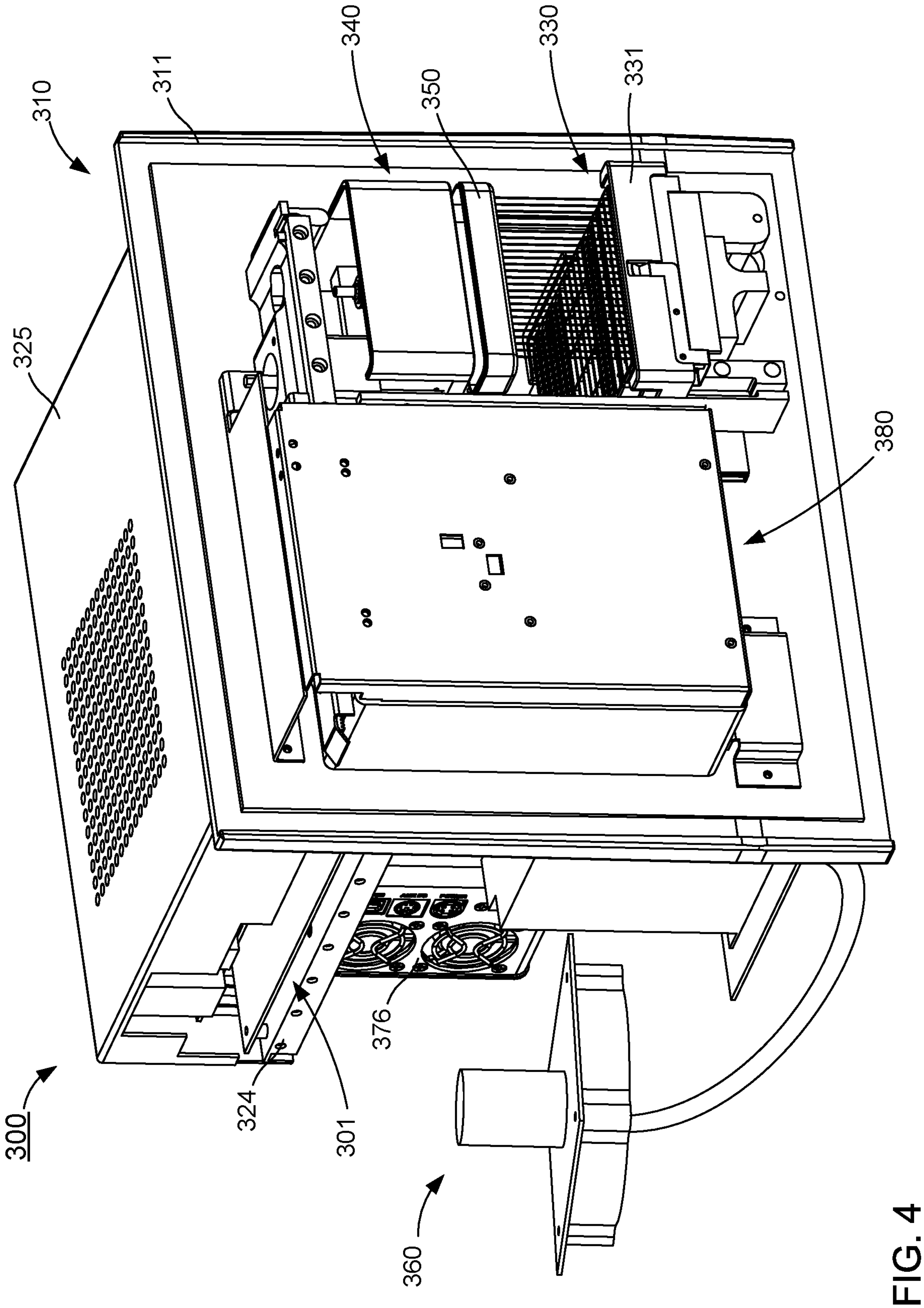
Figure 5:
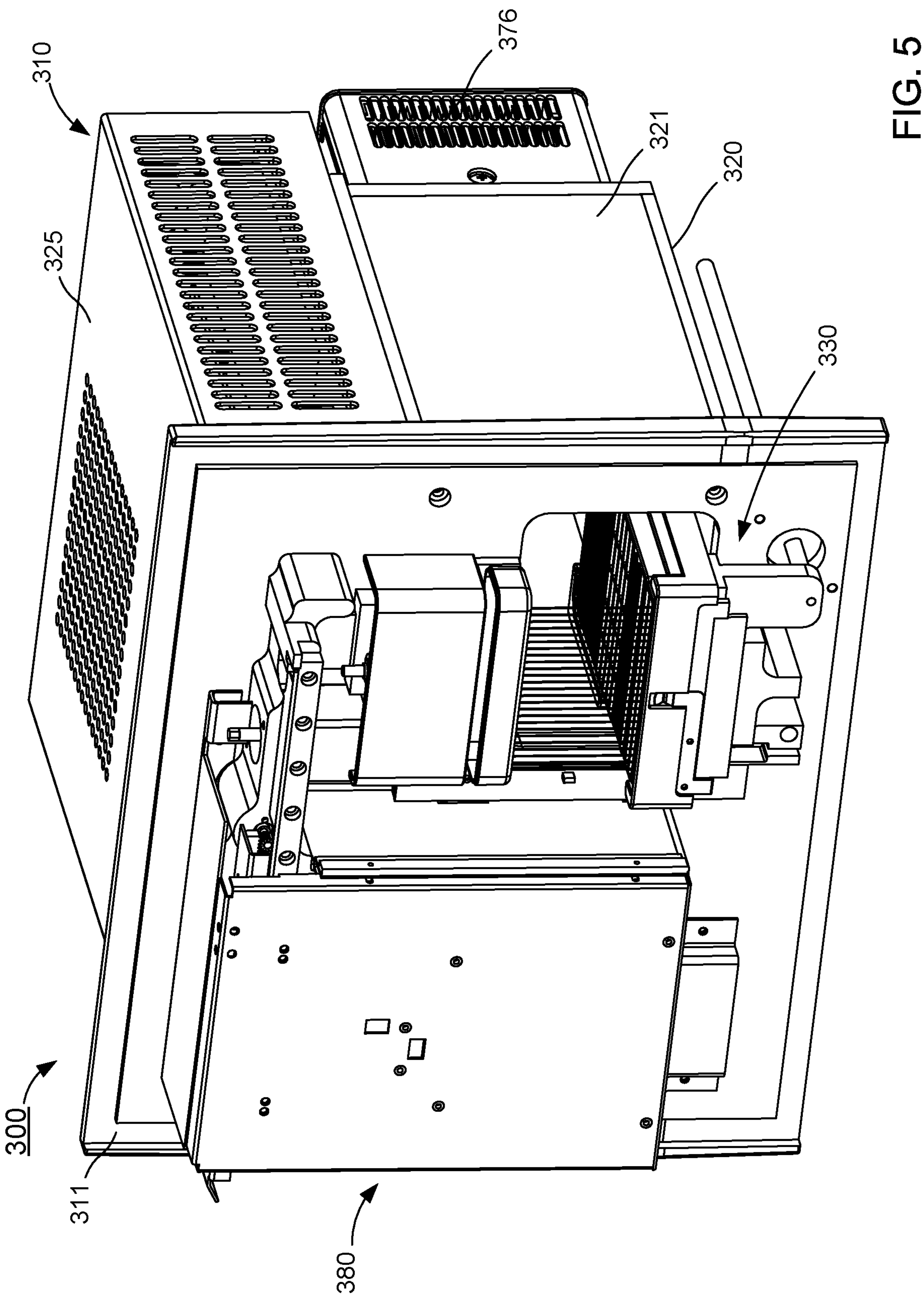
Figure 31:
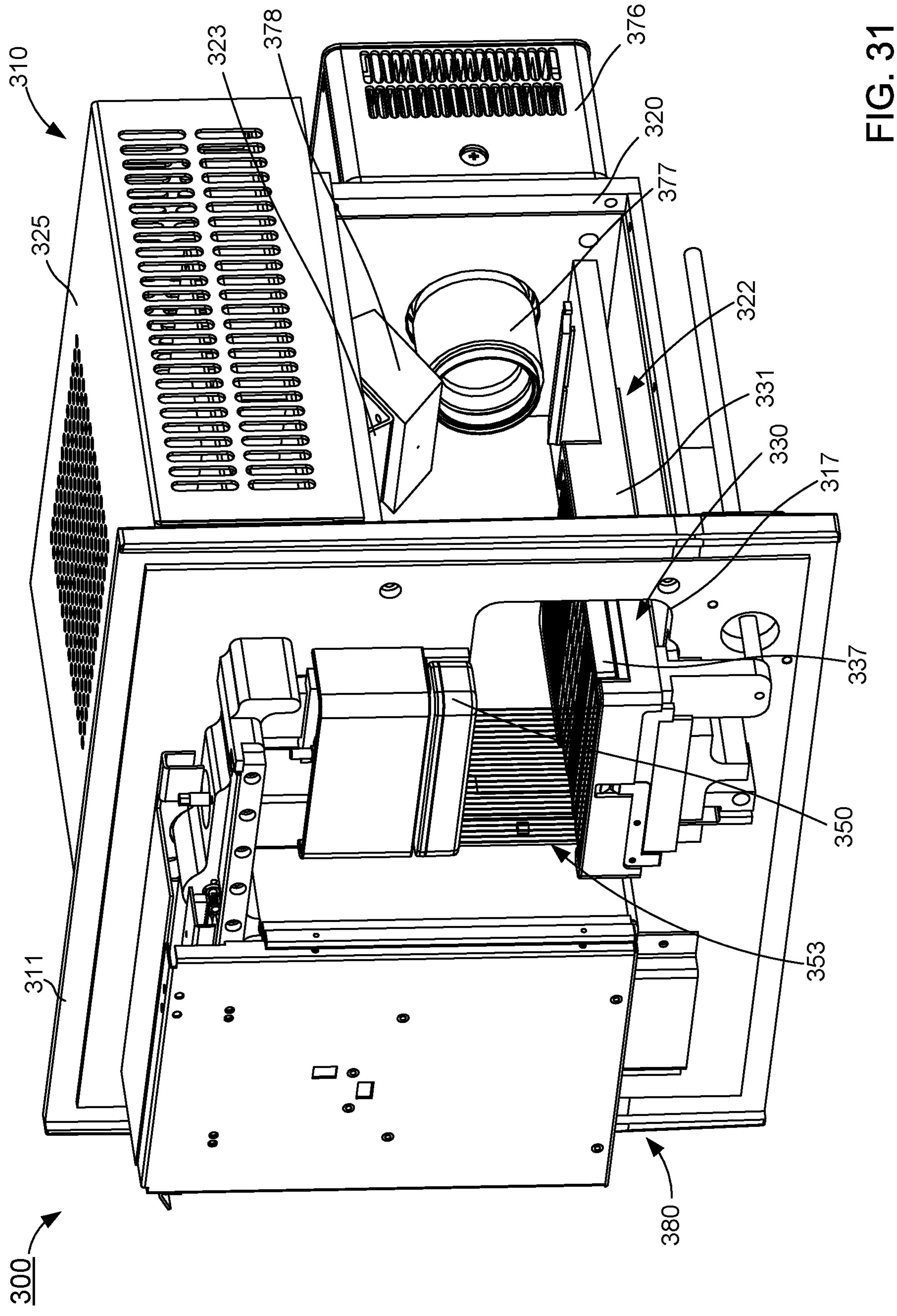
FIG. 31 is a right perspective view of the capillary electrophoresis system of FIG. 3, shown without a portion of the housing to illustrate a detection assembly.

FIGS. 3-31 illustrate a capillary electrophoresis system 300 according to an embodiment. FIGS. 3-5 are a front view, a left perspective view, and a right perspective view, respectively, illustrating the capillary electrophoresis system 300 (also referred to herein as "system"). The system 300 includes a housing 310 (FIGS. 6-8), an electronics assembly 301 (FIGS. 8, 12-15, 18, and 26) a reagent assembly 330 (FIG. 9-15), a cartridge assembly 340 (FIGS. 16-22), a vacuum assembly 360 (FIGS. 22-25), a light assembly 380 (FIGS. 26-30), and a detector assembly 375 (FIGS. 7 and 31). The system 300 can be configured to perform at least a semi-automated immunoassay of a sample using electrophoresis and, more particularly, capillary electrophoresis. Therefore, as described in further detail herein, the system 300 can be configured to at least semi-automatically draw a sample (e.g., including any suitable agent, reagent, protein, analyte, buffer, lysate, and/or any other material described herein) into a set of capillaries, separate the sample (via electrophoresis), immobilize at least some of the constituents of the sample (e.g., via heat, UV exposure, and/or the like), and detect the presence or the absence of a target analyte.

The housing 310 (FIGS. 6-8) of the system 300 can be any suitable shape, size, or configuration and can be arranged to at least partially enclose or at least partially support any suitable component of the system 300. The housing 310 includes a front plate 311, a first support structure 320, and a second support structure 322. Although not shown in FIGS. 3-31, in some embodiments, the system 300 can include an outer housing member and/or a case within which the system 300 can be disposed. Similarly stated, in some embodiments, the system 300 can include the outer housing member that can enclose or otherwise house substantially the entire system 300. In such embodiments, the outer housing member can include any suitable access door(s), drawer(s), window(s), etc. that can provide a user with access (e.g., either visual and/or physical) to the system 300.

Figure 6:
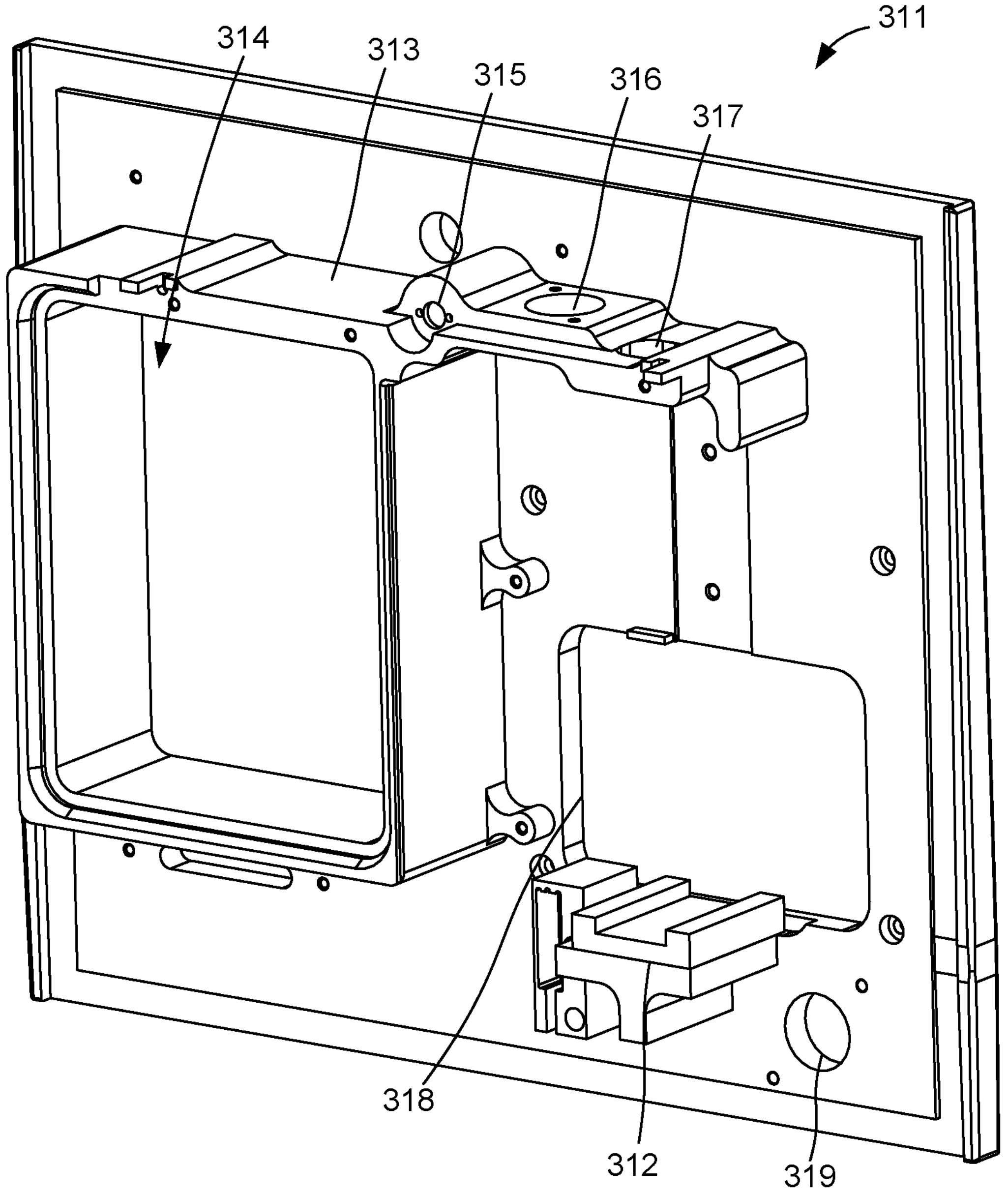
FIG. 6 is a perspective view of a front plate included in a housing of the capillary electrophoresis system of FIG. 3.
Figure 7:
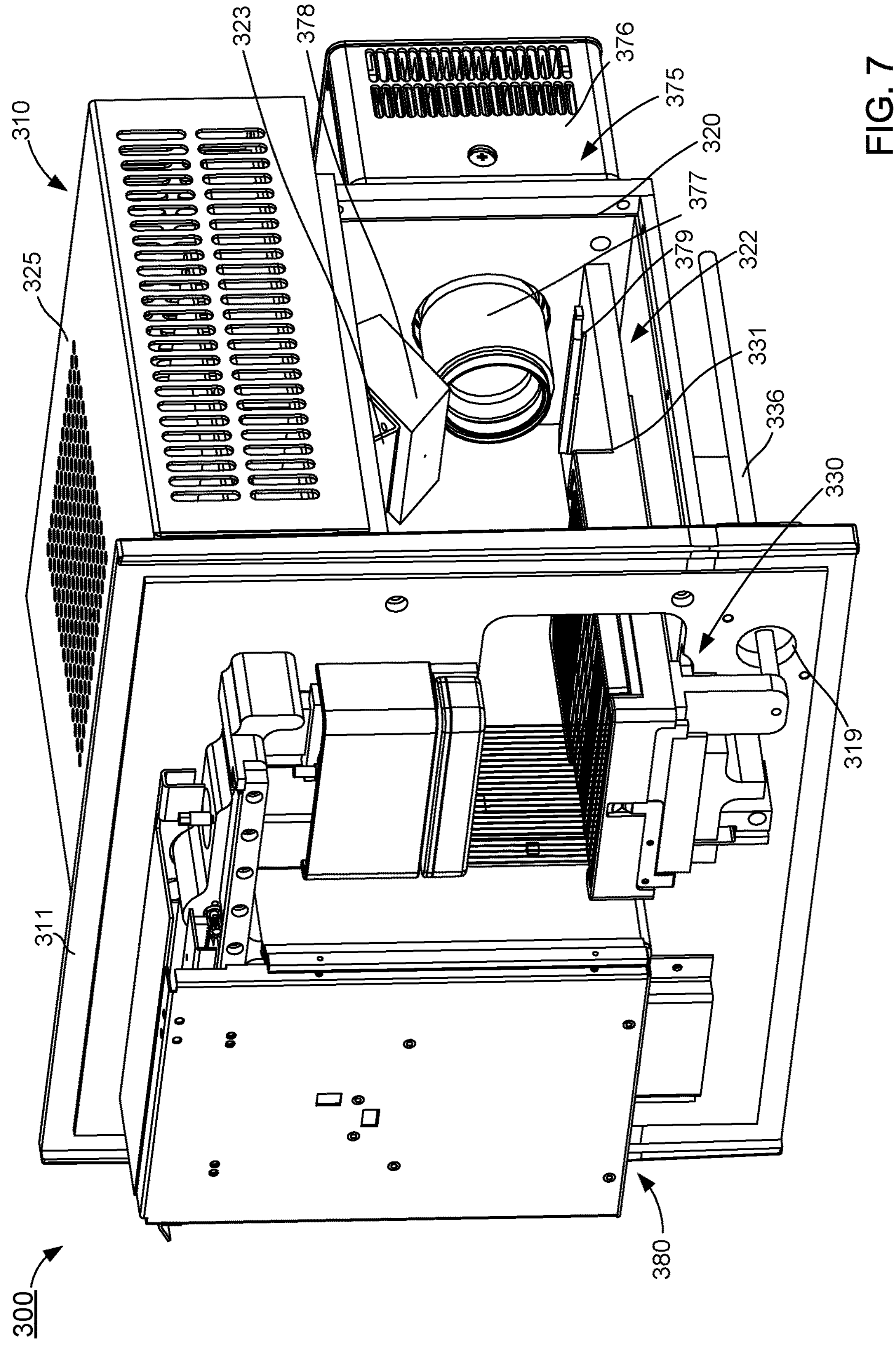
FIG. 7 is a right perspective view of the capillary electrophoresis system of FIG. 3 shown without a portion of the housing to illustrate a reagent chamber.

FIG. 6 is a perspective view of the front plate 311 included in the housing 310. The front plate 311 can be formed from any suitable material using any suitable manufacturing process. For example, in some embodiments, the front plate 311 can be formed from a single billet such as aluminum, steel, stainless steel, or the like that is milled, driller, or otherwise machined to form the front plate 311. In some embodiments, the front plate 311 can be cast via any suitable casting technique. In other embodiments, the front plate 311 can be formed from any number of components that are formed into a desired shape and coupled together via any number of welds, adhesives, mechanical fasteners, and/or the like. In still other embodiments, the front plate can be formed from a plastic, polymer, and/or composite material.

The front plate 311 includes a first mounting portion 312 and a second mounting portion 313 and defines a first reagent assembly opening 318 and a second reagent assembly opening 319. The first mounting portion 312 extends from a front surface of the front plate 311 to provide a mounting and/or support structure to which a portion of the reagent assembly 330 can be coupled. For example, as shown in FIG. 6, the first mounting portion 312 can define a channel or track that can slidably receive a portion of the reagent assembly 330, thereby supporting the reagent assembly 330 and defining a path (e.g., a track) along which the reagent assembly 330 can move. Furthermore, the first reagent assembly opening 318 can movably receive at least a portion of the reagent assembly 330 (see e.g., FIG. 7) when the reagent assembly 330 is moved relative to the first mounting portion 312, as described in further detail herein.

The second mounting portion 313 extends from the front surface of the front plate 313 to provide a mounting structure to which a portion of cartridge assembly 340, a portion of the vacuum assembly 360, and a portion of the light assembly 380 can be coupled. More specifically, the first mounting portion 313 extends from the surface of the front plate 311 and defines a recess 314 that receives a portion of the light assembly 380, a drive shaft opening 315 that receives a second portion of the light assembly 380, a lead screw opening 316 that receives a portion of the cartridge assembly 340, and a vacuum opening 317 that receives a portion of the vacuum assembly 360.

Figure 8:
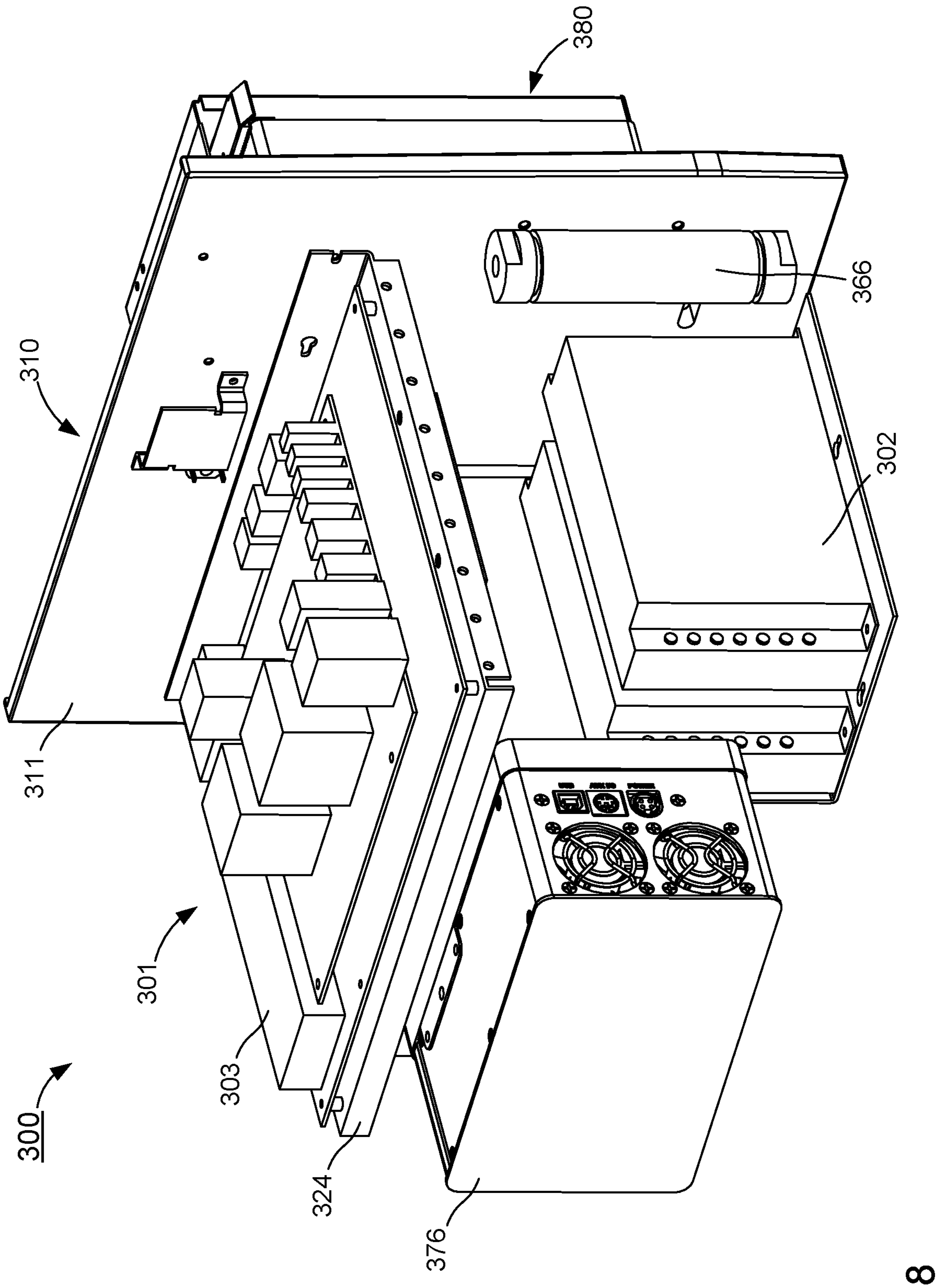
FIG. 8 is a rear perspective view of the capillary electrophoresis system of FIG. 3 shown without a portion of the housing to illustrate a portion of an electronics system included in the capillary electrophoresis system of FIG. 3.

As shown in FIGS. 7 and 8, the first support structure 320 and the second support structure 322 are each coupled (e.g., welded, adhered, fastened (bolt, screw, rivet, etc.), or otherwise held in a fixed position) to a rear surface of the front plate 311. The first support structure 320 is configured to support at least a portion of the detection assembly 375. Moreover, as shown in FIG. 7, the first support structure 320 and the front plate 311 collectively define a reagent chamber 322 that movably receives at least a portion of the reagent assembly 330, as described in further detail herein. The housing 310 also includes a cover 321 (see e.g., FIG. 5) that substantially encloses the reagent chamber 322. More specifically, the reagent chamber 322 is bounded by the front plate 311, the first support structure 320, and the cover 321, thereby limiting access to the reagent chamber 322 except through the first reagent assembly opening 318 defined by the front plate 311 (the reagent chamber 322 can be access while the system 300 is offline, however, by removing the cover 321).

The second support structure 324 has or defines a substantially flat surface that is coupled to and/or otherwise supports a main printed circuit board (PCB) 303 of the electronic assembly 301. Although shown in FIG. 8 as being in a substantially horizontal orientation relative to the front plate 311, in other embodiments, the second support structure 324 can be arranged relative to the front plate 311 at any suitable orientation. For example, in some embodiments, the second support structure 324 can be arranged in a substantially vertical orientation relative to the front plate 311. In this manner, the overall size of the system 300 can be managed at least in part by reorienting the second support structure 324. The housing 310 also includes a cover 325 (see e.g., FIGS. 4, 5, and 7) that substantially encloses or covers the main PCB 303.

Figure 26:
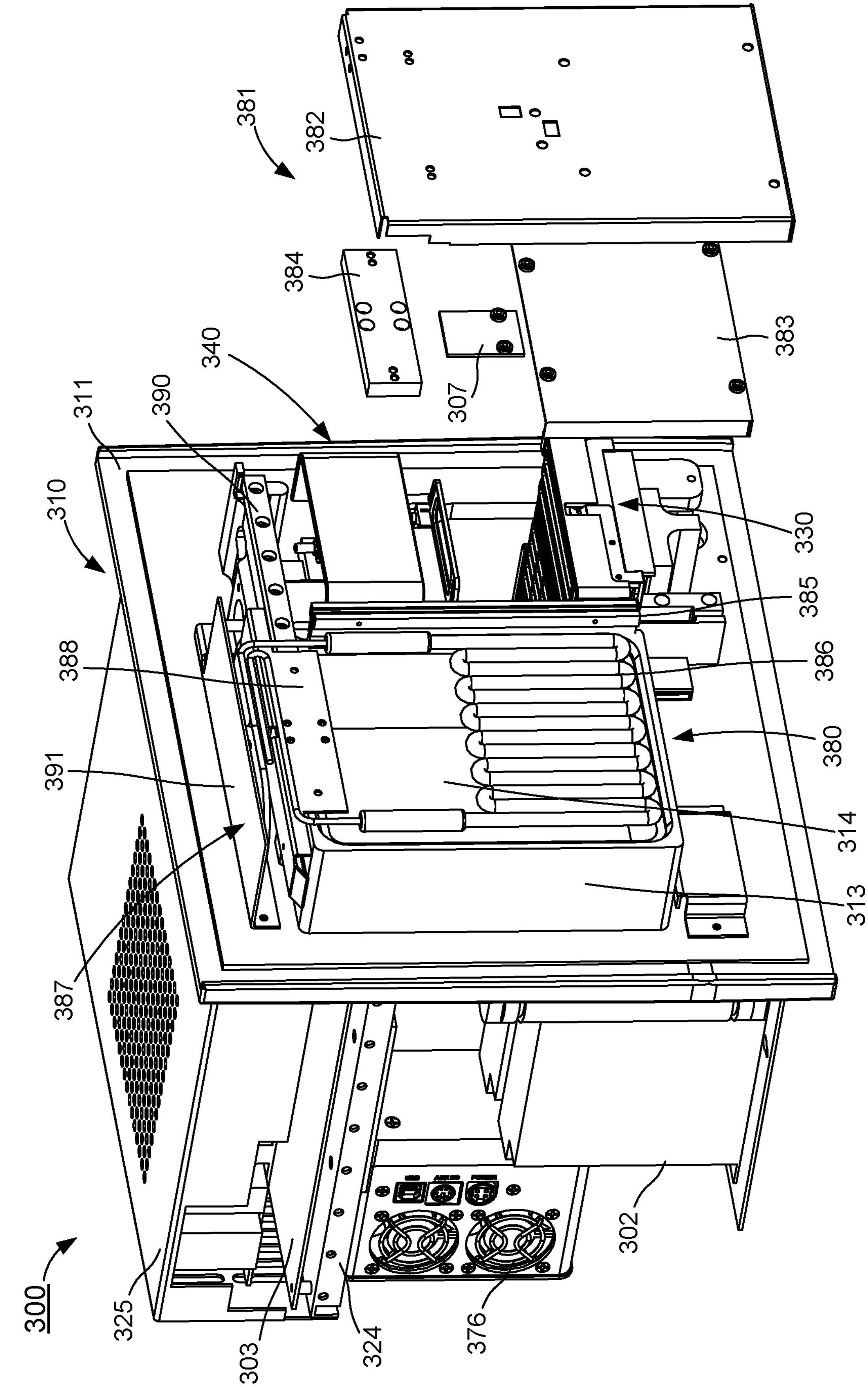
FIG. 26 is a partially exploded view of the capillary electrophoresis system of FIG. 3, illustrating a light assembly in a first position.

The electronics assembly 301 can be any suitable configuration and can include any suitable component to enable the electronics assembly 301 to at least partially control the system 300. For example, as shown in FIG. 8 the electronics assembly 301 includes a power source 302 and the main PCB 303. As described in further detail herein, the main PCB 303 is in electrical communication with a sensor PCB 304 (FIGS. 12-15), a cartridge PCB 306 (FIG. 18), and a light PCB 307 (FIG. 26). Although not shown in FIG. 8, the power source 302 can be electrically connected to an external electrical circuit (e.g., "plugged in") to receive a flow of current from a power grid. In this manner, the power source 302 can receive the flow of current and, in turn, can condition, transform, and/or convert the flow of current prior to being delivered to the electronic main PCB 303 (e.g., converted from alternating current (AC) to direct current (DC)). Moreover, the power source 302 can be configured to supply a flow of electrical current to one or more motors, actuators, lights, detectors, cameras, and/or the like, as described in further detail herein.

The main PCB 302 can include any suitable electronic device or component. For example, the man PCB 302 includes at least a memory and a processor (not shown in FIGS. 3-31). The memory can be, for example, a random access memory (RAM), a memory buffer, a hard drive, a read-only memory (ROM), an erasable programmable read-only memory (EPROM), and/or so forth. In some embodiments, the memory can stores instructions to cause the processor to execute modules, processes, and/or functions associated with controlling at least a portion of the system 300. The processor can be any suitable processing device that can run and/or execute a set of instructions or code. For example, the processor can be a general purpose processor, a central processing unit (CPU), an accelerated processing unit (APU), an application specific integrated circuit (ASIC), and/or the like. The processor can run and/or execute a set of instructions or code stored in the memory associated with controlling at least a portion of the system 300. More specifically, in some instances, the processor can execute a set of instructions or code stored in the memory associated with controlling one or more motors, actuators, sensors, lights, etc. Furthermore, the processor can execute a set of instructions or code stored in memory associated with sending a flow of current to a portion of the cartridge assembly 340 to initiate and/or perform electrophoresis, as described in further detail herein.

As shown in FIGS. 7 and 8, the detection assembly 375 of the system 300 can be disposed, at least partially, within the housing 310 and arranged on a first side of the cartridge assembly 340, as described in further detail herein. More specifically, the detection assembly 375 includes an optical detector 376 and a scanner 378. The optical detector 375 can be any suitable device, mechanism, and/or assembly that is configured to detect a signal emitted by, for example, an analyte and/or a standard (described above). For example, the optical detector 375 can be a charged coupled device (CCD) array and/or the like that can be used to continuously monitor, in real time, the signal emitted by the analyte and/or the standard to allow a user to rapidly determine whether an analyte is present in the sample, and optionally, the amount or activity of the analyte. As shown in FIG. 7, the optical detector 375 includes a lens 377 that is disposed, at least partially, within the reagent chamber 322. The lens 377 can be any suitable lens that can include and/or be coupled to, for example, a filter (e.g., a TAMRA filter) that is associated with the signal (e.g., chemiluminescence, fluorescence, and/or the like). The optical detector 375 can be operably coupled to the main PCB 303 to receive a signal from and/or to send a signal to the processor or the like. As shown in FIG. 7, the scanner 378 is disposed within the reagent chamber 322 and is coupled to a scanner bracket 323 that extends from a surface of the first support structure 320. In some embodiments, the scanner 378 is a barcode scanner configured to read identifying information on the reagent tray (i.e., embedded in a barcode). In some embodiments, when the reagent tray moves out, a mirror 379 is exposed, thereby enabling the scanner to read identifying information on the cartridge. In some embodiments, a fluorescence detector (not shown) is configured to work in conjunction with the optical detector 376 to detect a signal emitted by the analyte and/or the standard, as described in further detail herein.

As shown in FIGS. 9-15, the reagent assembly 330 of the system 300 includes a reagent tray holder 331 (also referred to herein as "holder"), a drive mechanism 334, and a reagent tray 337. As described above, the reagent assembly 330 is supported (at least in part) by the first mounting portion 312 of the front plate 311 such that at least a portion of the reagent assembly 330 of the system 300 can be movably disposed within the reagent chamber 322 defined by the housing 310. For example, although not shown in FIGS. 9-15, the holder 331 can include a rail or the like that can be movably coupled to the first mounting portion 312 of the front plate 311 (e.g., movably disposed in the channel or the like (see e.g., FIGS. 12 and 13)).

Figure 9:
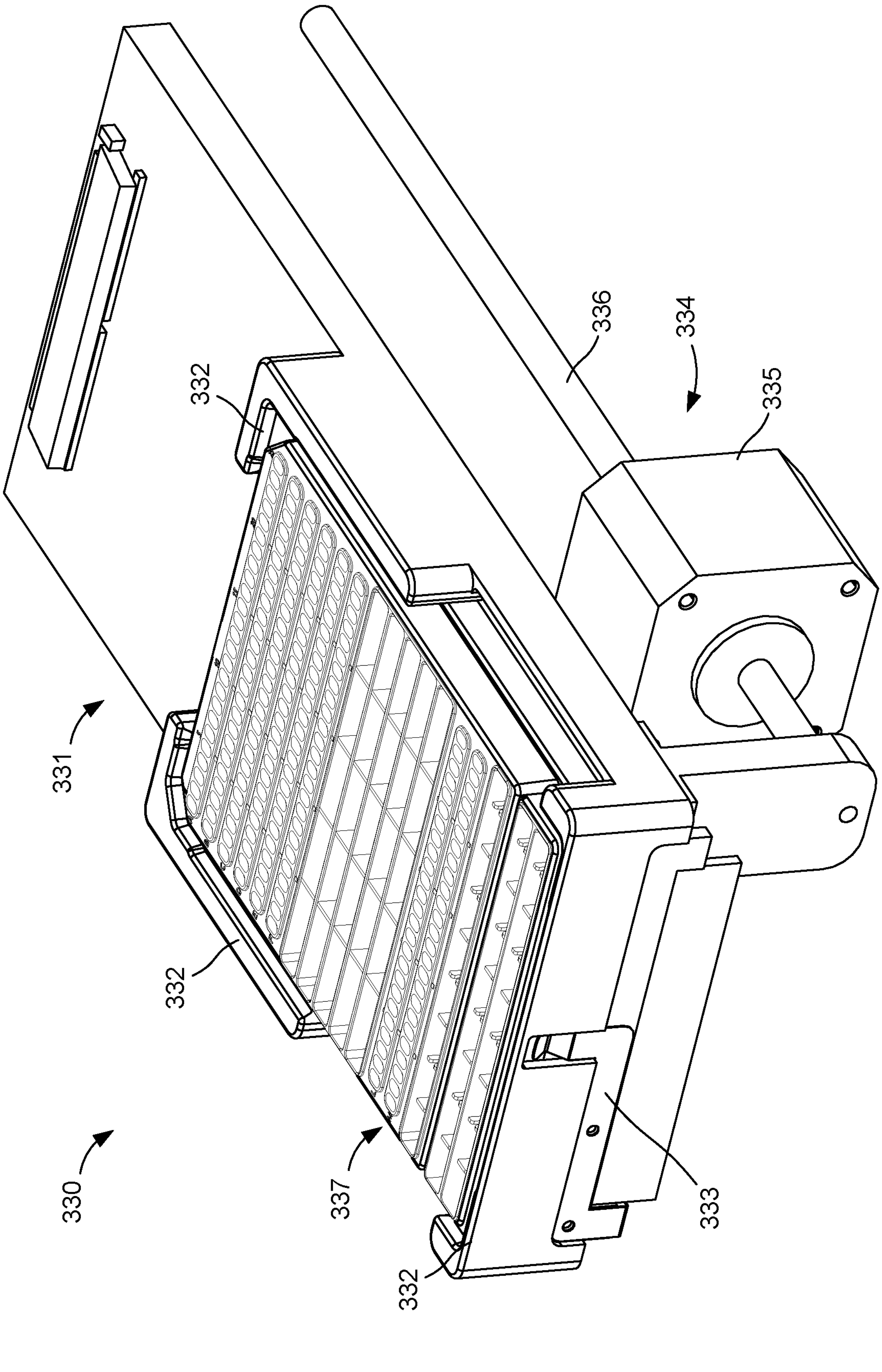
FIG. 9 is a perspective view of a reagent assembly included in the capillary electrophoresis system of FIG. 3.
Figure 10:
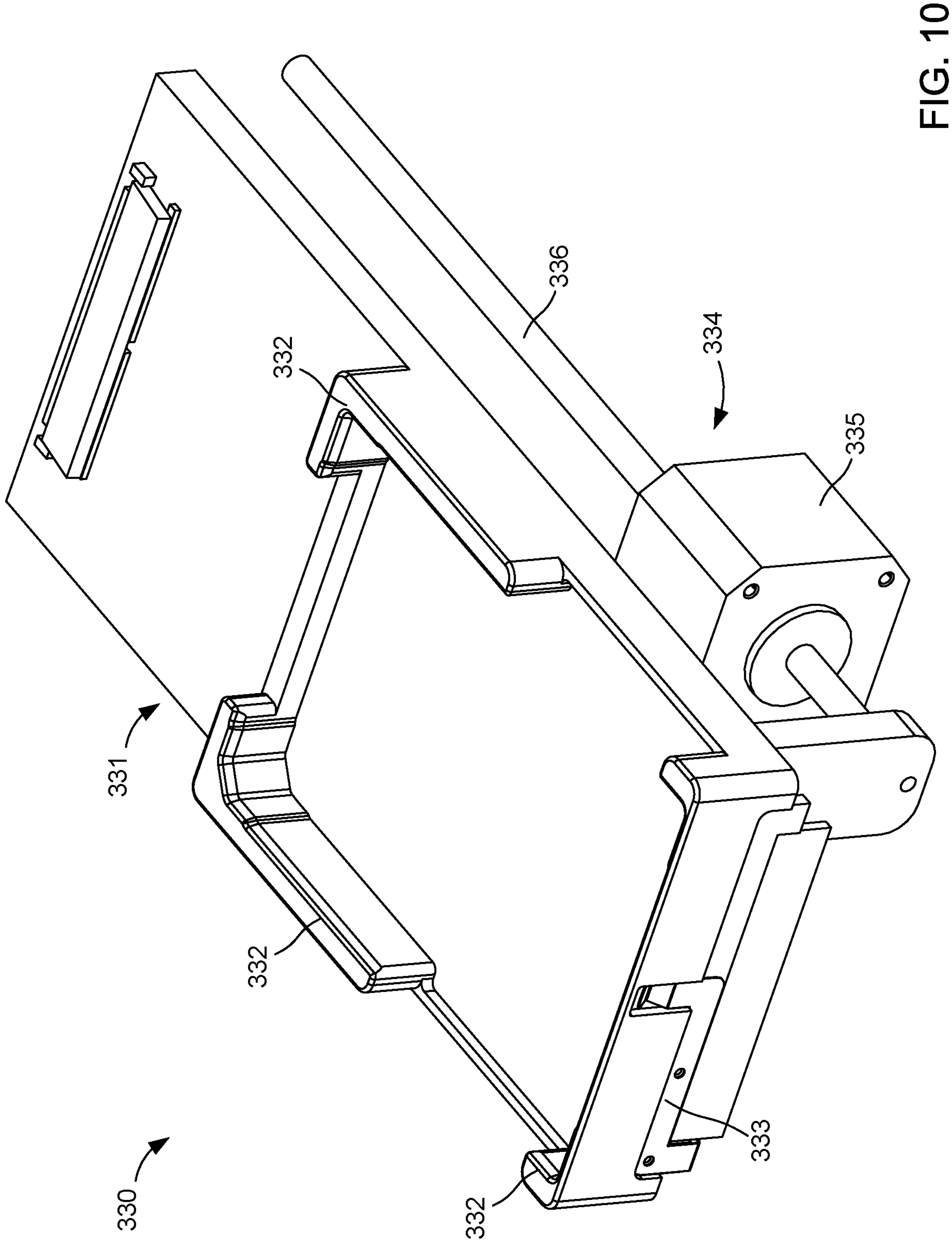
FIG. 10 is a perspective view of a holder included in the reagent assembly of FIG. 9.
Figure 11:
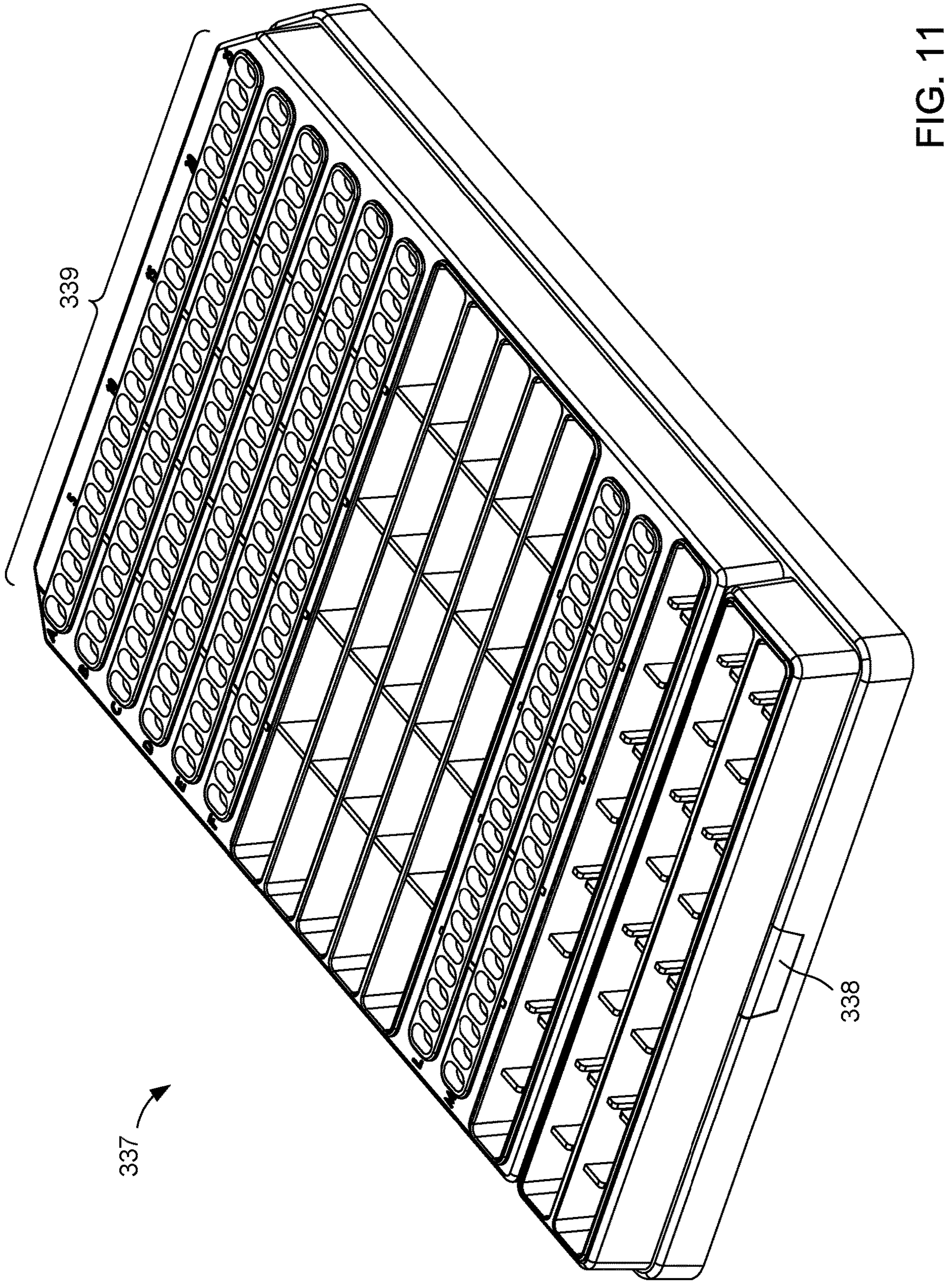
FIG. 11 is a perspective view of a reagent tray included in the reagent assembly of FIG. 9.
Figure 12:
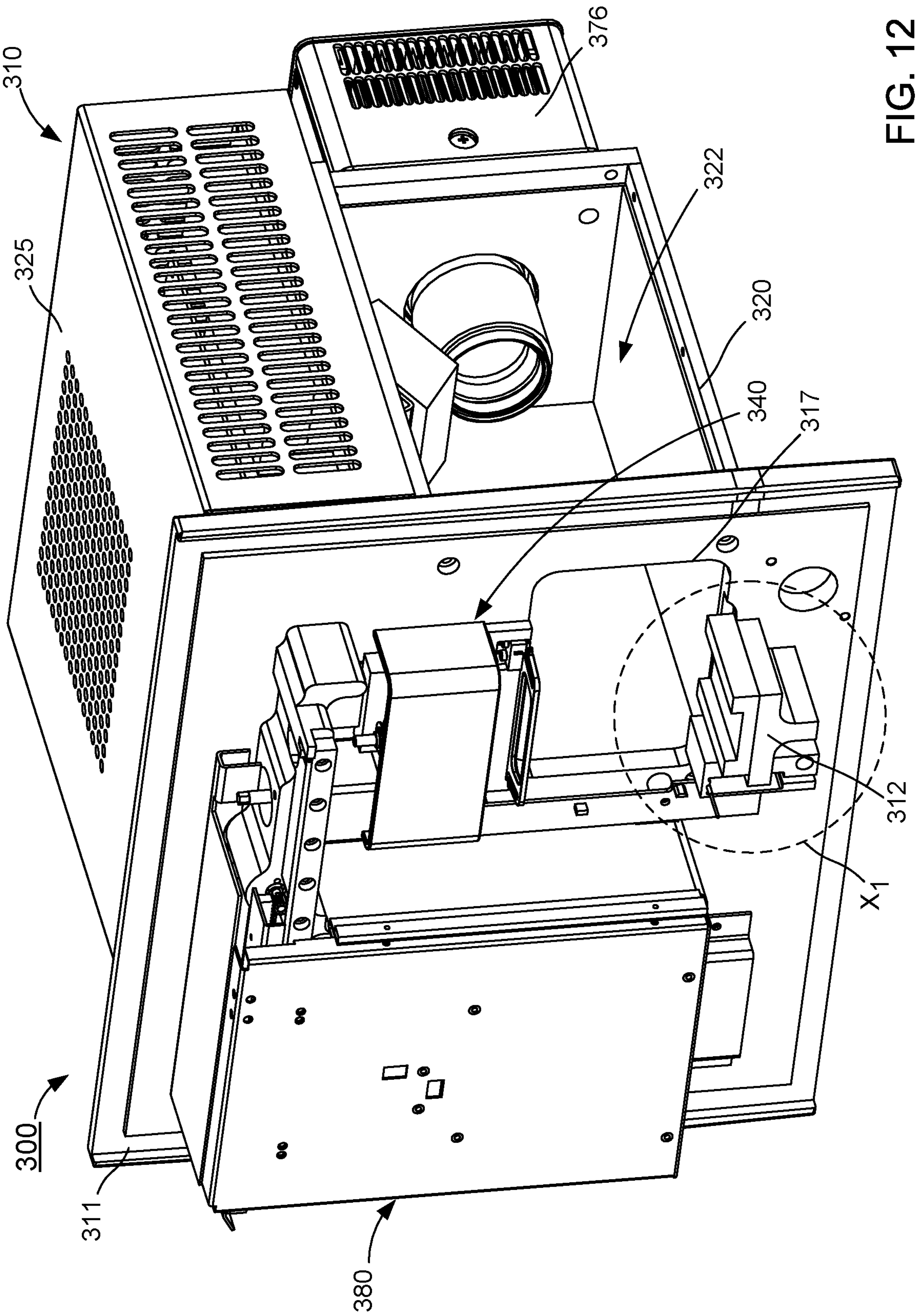
FIG. 12 is a right perspective view of a portion of the capillary electrophoresis system of FIG. 3.
Figure 13:
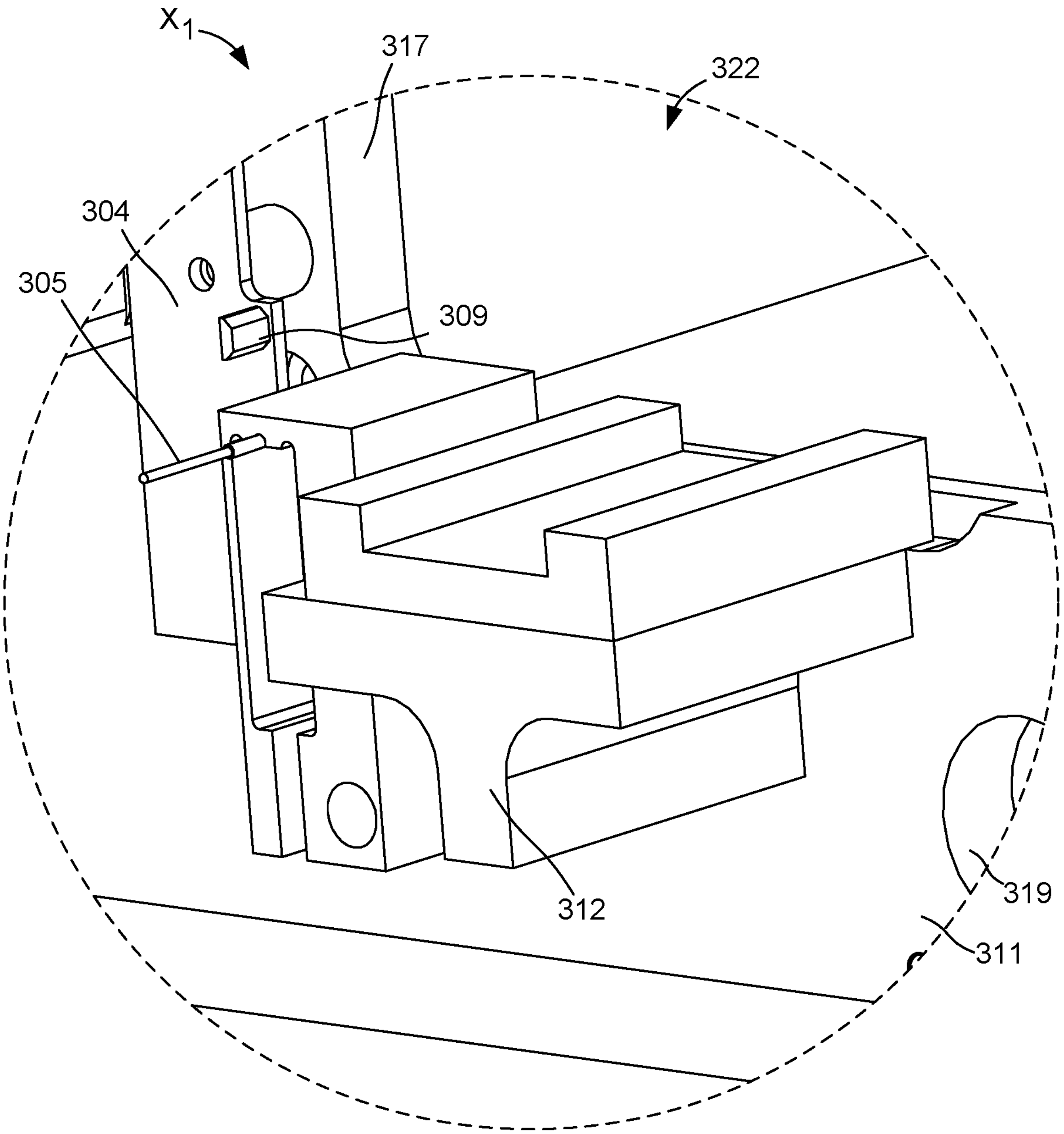
FIG. 13 is an enlarged view of the portion of the capillary electrophoresis system identified as the region $X_1$ in FIG. 12.
Figure 14:
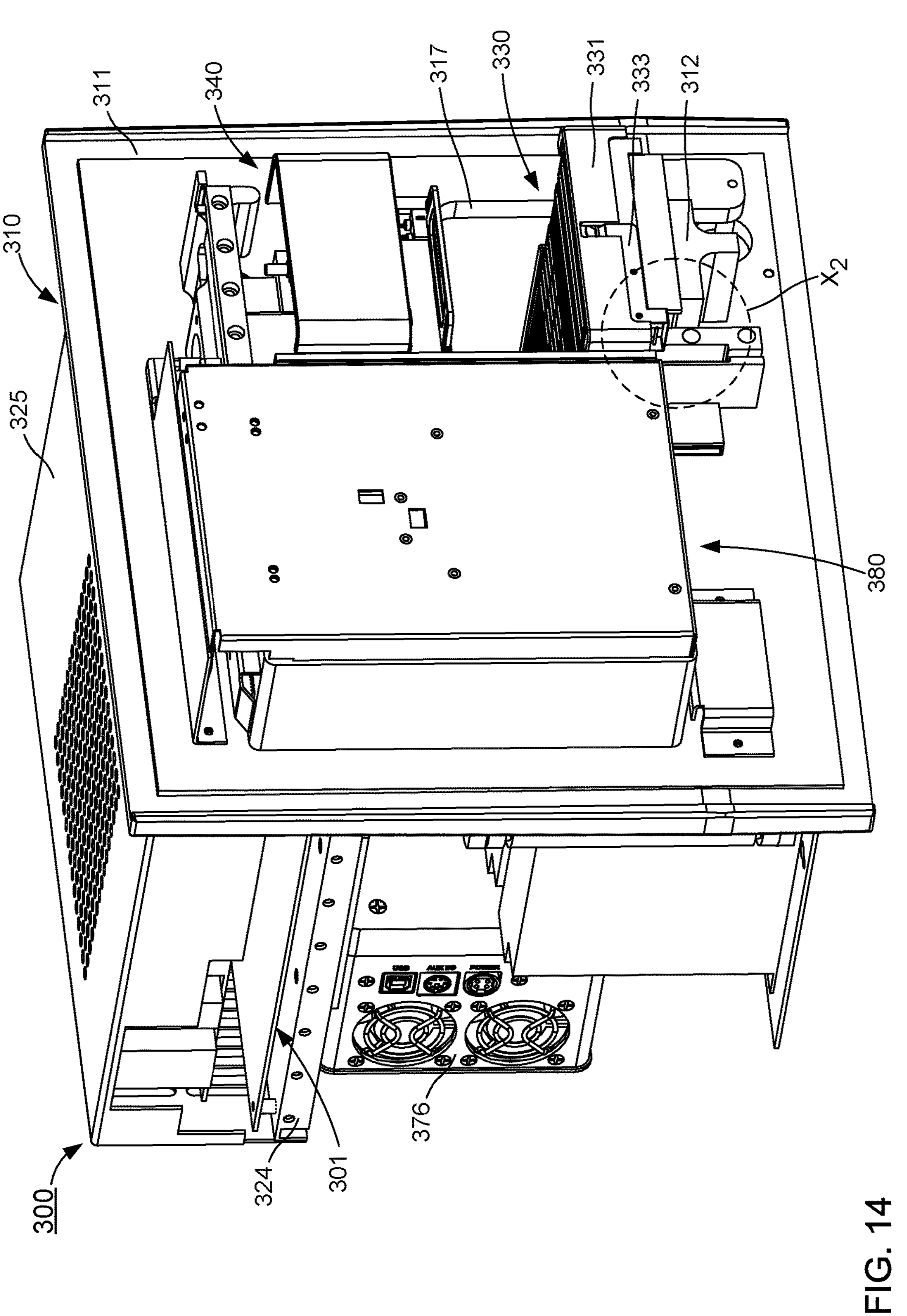
FIG. 14 is a left perspective view of a portion of the capillary electrophoresis system of FIG. 3.
Figure 15:
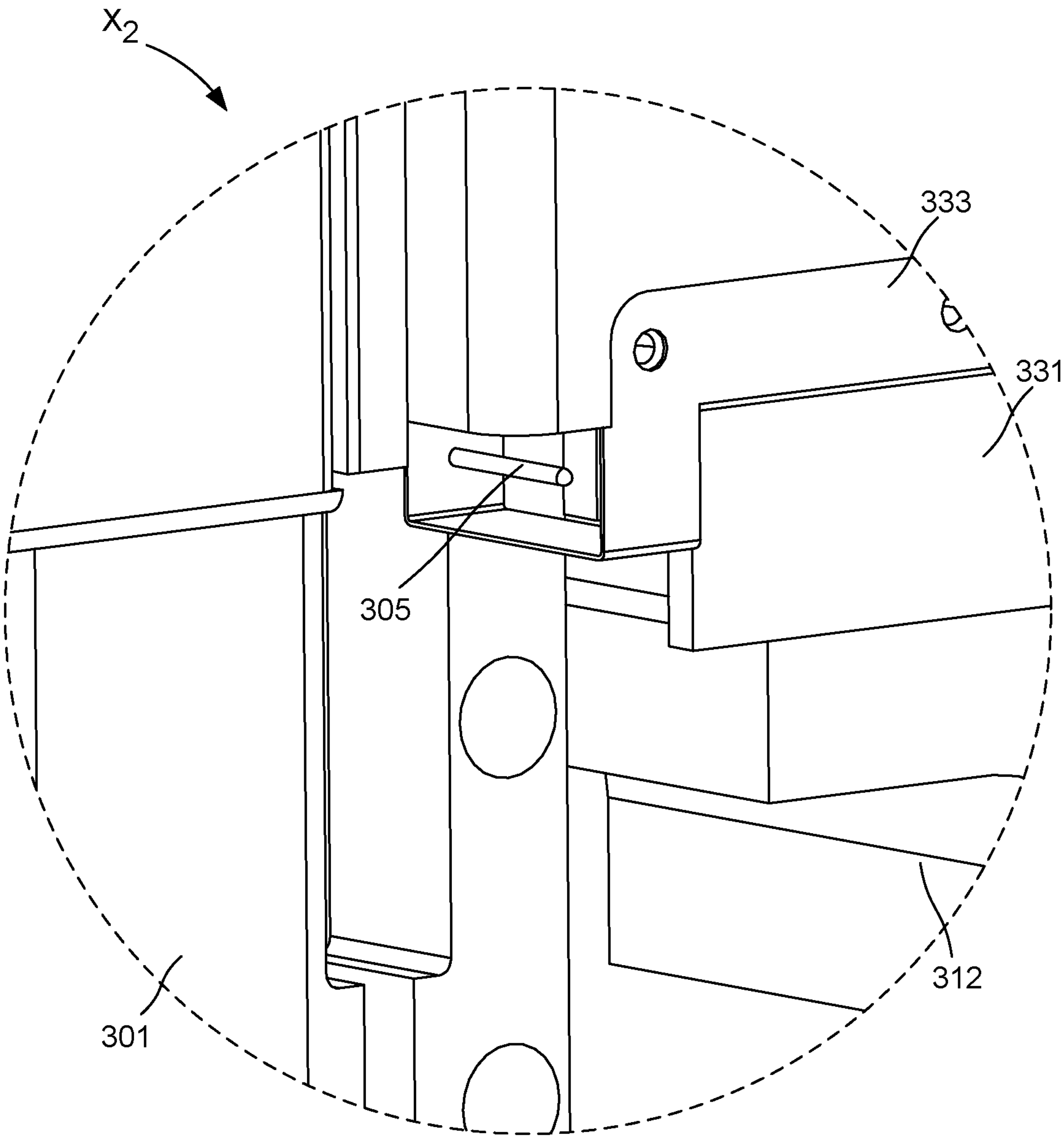
FIG. 15 is an enlarged view of the portion of the capillary electrophoresis system identified as the region $X_2$ in FIG. 14.
Figure 16:
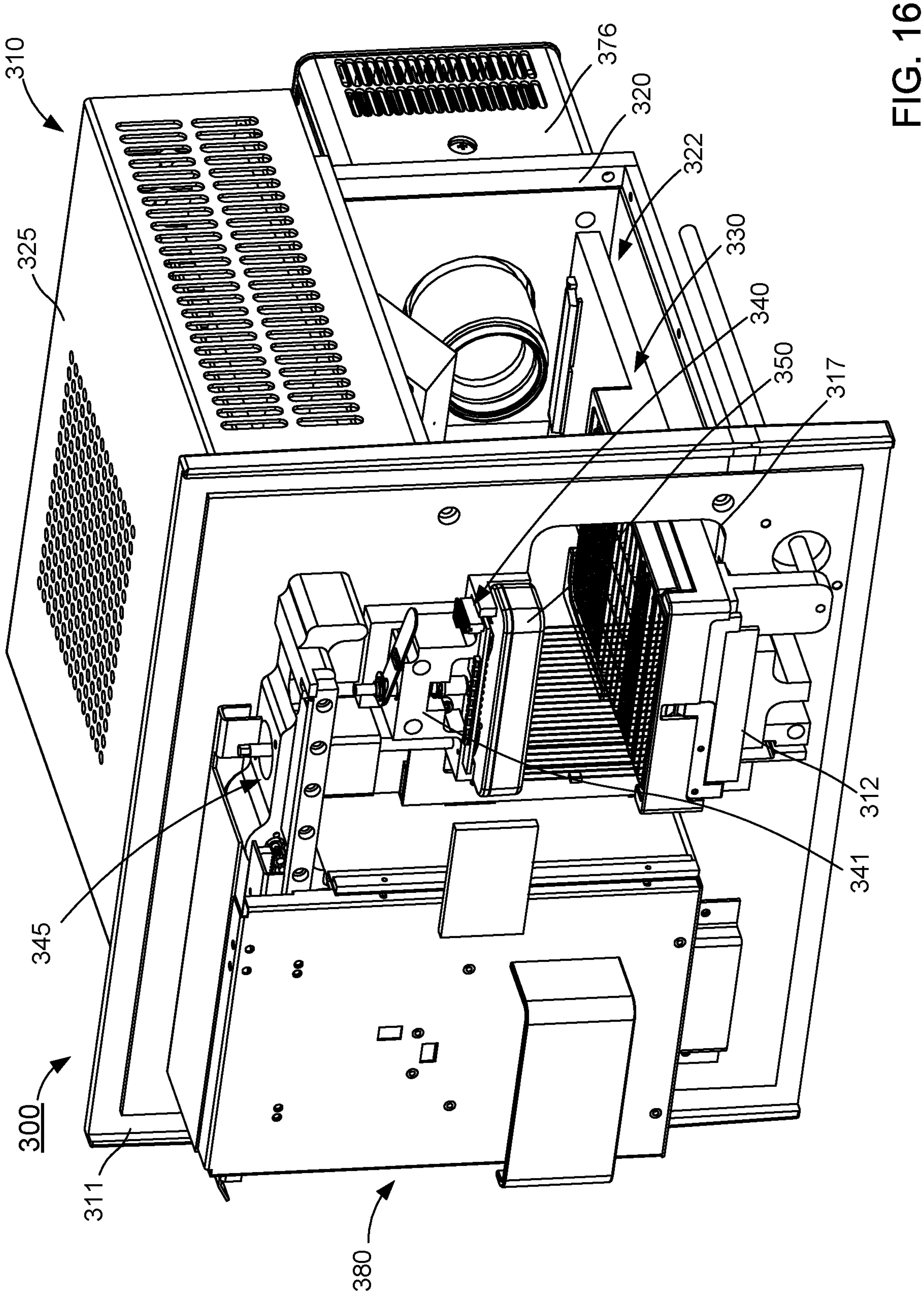
FIG. 16 is a right perspective view of the capillary electrophoresis system of FIG. 3, illustrating a cartridge assembly.

As shown in FIGS. 9-11, the holder 331 is configured to receive at least a portion of the reagent tray 337 to substantially retain, hold, or otherwise limit its movement when coupled thereto. More specifically, as shown in FIGS. 9 and 10, the holder 331 includes a set of retaining walls 332 that extend from a surface of the holder 331 to define an area of the holder 331 that receives the reagent tray 337. In some embodiments, the reagent tray 337 can include an outer surface that can engage an inner surface of the retaining walls 332 when disposed therebetween. As such, the retaining walls 332 and the reagent tray 337 can form, for example, a friction fit that can limit the movement of the reagent tray 337 relative to the holder 331 in a lateral direction. Furthermore, the holder 331 includes an electrical contact 333 that is configured to engage the outer surface of the reagent tray 337 to limit a vertical movement (e.g., normal to the surface of the holder upon which the reagent tray 337 sits) of the reagent tray 337 relative to the holder 331. For example, the electrical contact 333 can include a tab or the like that can be placed in contact with a retention portion 338 (e.g., a recessed surface, a protrusion, a portion formed of a secondary material having a high coefficient of friction, and/or the like) of the reagent tray 337 (FIG. 11).

The reagent tray 337 can be any suitable tray or the like. For example, in some embodiments, the reagent tray 337 can hold and/or otherwise define a set of well plates 339. In some embodiments, the well plates 339 can be microwell plates and/or the like. The well plates 339 can be any suitable shape, size, or configuration and can be disposed in any suitable arrangement. For example, as shown in FIG. 11, the reagent tray 337 can include 227 wells having various configurations. In other embodiments, a reagent tray can include set of 96 microwells that are spaced at about 9 millimeter (mm) center-to-center spacing. In other embodiments, a reagent tray can include a set of 384 microwells that are spaced at about 4.5 mm center-to-center spacing. Although specific examples of reagent trays are described, the holder 331 can be configured to receive any suitable reagent tray 337 of similar size and/or shape that can define any number and/or any arrangement of wells and/or microwells. As such, the wells 339 included in or defined by the reagent tray 337 can receive any suitable solution, fluid, gel, lysate, buffer, sample, analyte, ampholyte, agent, reagent, protein, matrix, and/or the like.

In some embodiments, the reagent tray 337, or a portion of the reagent tray, is electrically conductive. For example, some or all of the wells or rows of wells can be electrically conductive and can act as an electrical connection.

The drive mechanism 334 of the reagent assembly 330 includes a motor 335 and a lead screw 336. In some embodiments, the lead screw 336 is rotatably coupled to the holder 331. More specifically, the lead screw 336 can be coupled to the holder 331 such that a translational motion of the lead screw 336 relative to the holder 331 is limited while a rotational motion of the lead screw 336 relative to the holder 331 is not limited. The holder 331 can be positioned relative to the housing 310 to allow the lead screw 336 to extend through the second reagent assembly opening 319 defined by the front plate 311 (see e.g., FIG. 7). The motor 335 of the drive mechanism 334 can be any suitable motor that selectively engages the lead screw 336. Although not shown in FIGS. 3-31, the motor 335 is coupled to a surface of the front plate 311 (e.g., a back surface) to limit movement of the motor 335 relative to the housing 310. As such, the motor 335 can receive a signal (e.g., a flow of electrical current) from the power source 302 and/or the main PCB 302 that is operable in activating the motor 335 to rotate the lead screw 336 relative to the motor 335. Thus, with the motor 335 coupled (e.g., fixedly coupled) to the front plate 311, the rotational motion of the lead screw 336 advances the lead screw 336 in an axial direction relative to the motor 335 such that the holder 331 is moved in a direction normal to front plate 311 (e.g., normal to a front surface of the front plate 311). Said another way, the motor 335 can rotate the lead screw 336, for example, in a forward (e.g., counter-clockwise) direction to dispose a larger portion of the holder 331 in the reagent chamber 322 and can rotate the lead screw 336, for example, in a backward (e.g., clockwise) direction to dispose a smaller portion of the holder 331 in the reagent chamber 322.

In some embodiments, the lead screw 336 is fixed in position and does not rotate. In such embodiments, the motor 335 includes a nut (not shown) configured to rotate around the fixed lead screw and move the reagent tray as described above.

As shown, for example, in FIGS. 12-15, the electronics system 302 includes a contact 305 that is operably coupled to the sensor PCB 304. The contact 305 and the PCB 304 can be arranged to determine a position of the reagent assembly 330 relative to the housing 310 and/or the reagent chamber 322. As shown, the contact 305 can extend from a surface of the front plate 311 and can be disposed with an opening defined by the actuator 333 of the holder 331. For example, the actuator 333 can include an end portion that is substantially U-shaped. A first wall of the end portion that is adjacent to front plate 311 can define the opening and a second wall, opposite to the first wall can be substantially continuous (e.g., does not define an opening). Thus, when the reagent assembly 330 is moved relative to the housing 310 (e.g., by advancing the motor 335 relative to the lead screw 336) the end portion of the actuator 333 can be moved relative to the sensor 305. In this manner, the sensor 305 can be placed in contact with, for example, the second wall to determine the relative position of the reagent assembly 330. Said another way, the reagent assembly 330 can be moved relative to the housing 310 such that the end portion of the actuator 333 depresses or otherwise engages the sensor 305. Therefore, the relative position of the reagent assembly 330 can be determined by determining the amount the actuator 333 depressed the contact 305. In some embodiments, a Hall effect sensor 309 is engaged to determine a position of reagent assembly 330.

Figure 17:
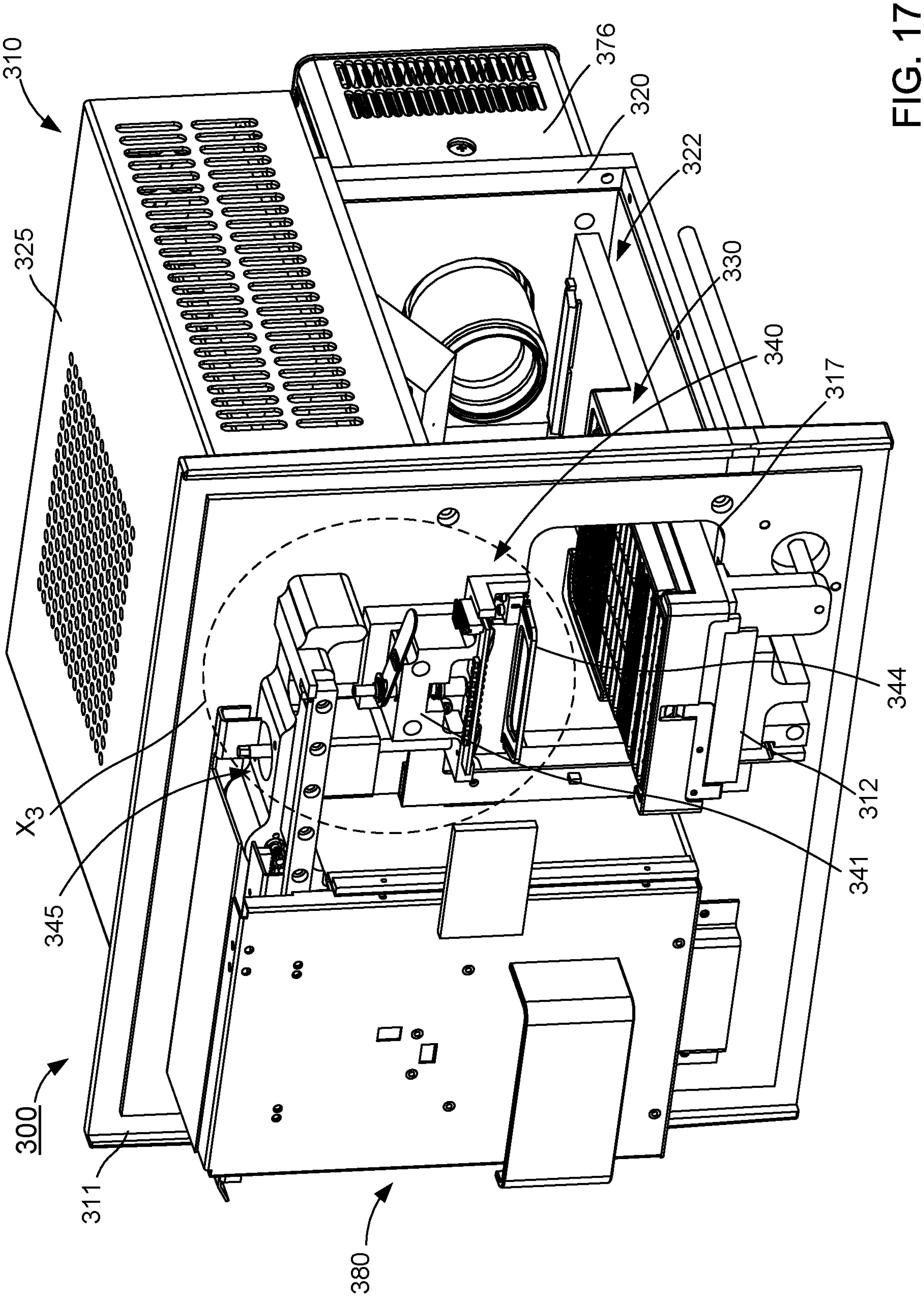
FIG. 17 is a right perspective view of the capillary electrophoresis system of FIG. 3, illustrating a portion of the cartridge assembly of FIG. 16.
Figure 18:
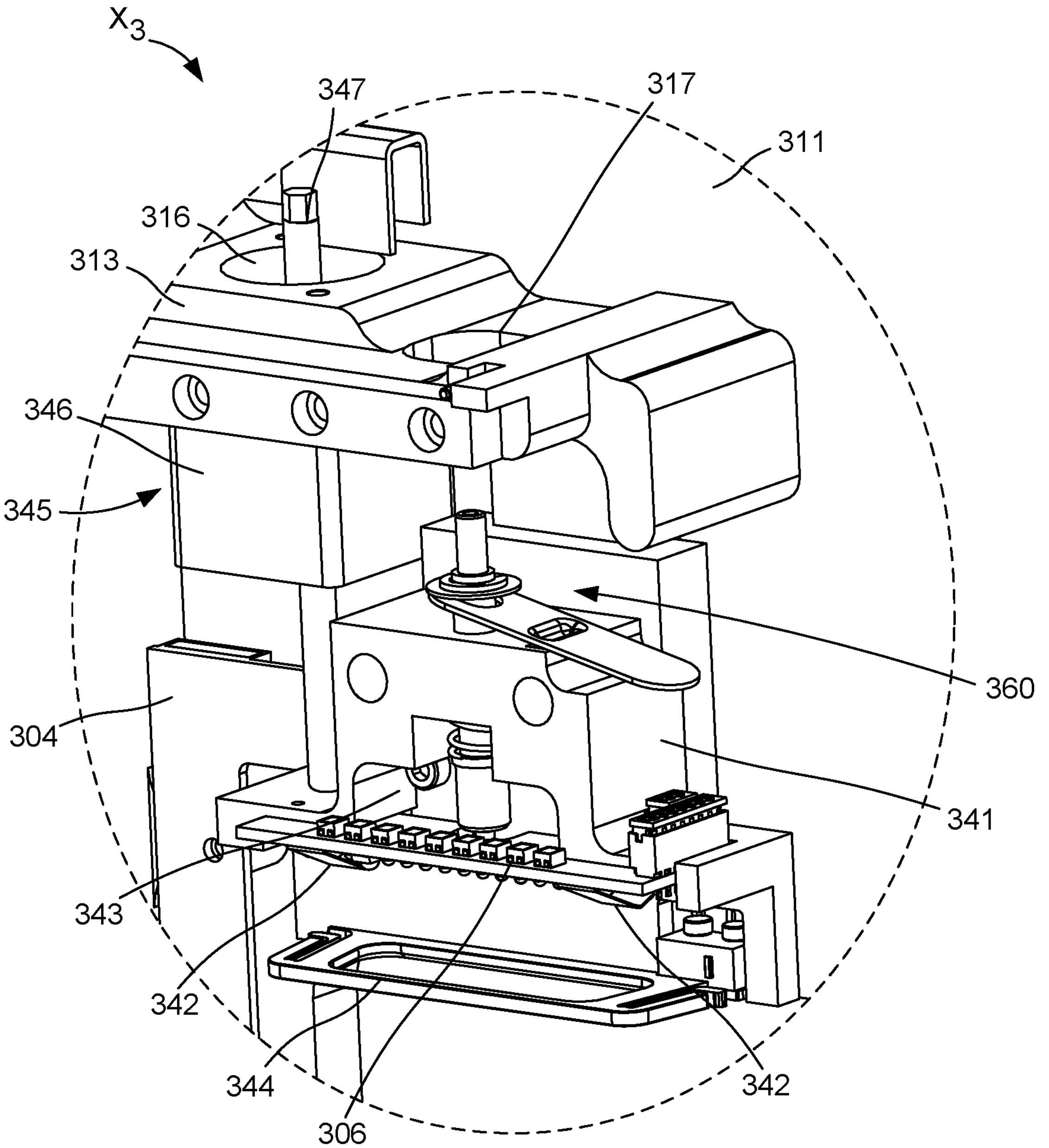
FIG. 18 is an enlarged view of the portion of the capillary electrophoresis system identified as the region $X_3$ in FIG. 17.

As shown in FIGS. 16-22, the cartridge assembly 340 includes a cartridge retainer 341 (also referred to herein as "retainer"), a drive mechanism 345, and a capillary cartridge 350 (also referred to herein as "cartridge"). The retainer 341 can be any suitable shape, size, or configuration and can be arranged to receive at least a portion of the cartridge 350 (see e.g., FIG. 16). The retainer 341 has or defines a substantially C-shaped cross-section with at least one side of the retainer 341 being substantially open to receive at least a portion of the cartridge 350, as shown in FIGS. 17 and 18. More specifically, the retainer 341 includes a base 344 and defines a recess 343. The recess 343 is configured to receive the cartridge PCB 306 and at least a portion of the vacuum assembly 360, as described in further detail herein. The retainer 341 also includes a set of retention tabs 342. In this manner, the cartridge 350 can be disposed within the recess 343 defined by the retainer 341 such that the base 344 and the retention tabs 342 engage the cartridge 350 to limit its movement relative to the retainer 341. For example, in some embodiments, the retention tabs 342 act as an electrical contact and can be a deformable material such as beryllium copper or the like that can be transitioned from an undeformed configuration to a deformed configuration when the cartridge 350 is disposed in the recess 343. Thus, in response to being transitioned to the deformed configuration, the retention tabs 342 can exert a reaction force on the cartridge 350 that is operable in retaining, at least temporarily, the cartridge 350 within the recess 341. In some embodiments, the arrangement of the retainer 341 and/or the cartridge 350 can be such that the cartridge 350 is in a predetermined orientation relative to the retainer 341 when disposed in the recess 343. Similarly stated, the retainer 341 can be configured to receive the cartridge 350 in a single, predetermined orientation. In other instances, the cartridge 350 can be disposed in the recess 343 of the retainer 341 in any suitable orientation.

The drive mechanism 345 can be coupled to the front plate 311 and the retainer 341 and can be operable in moving the retainer 341 relative to the housing 310. For example, in some embodiments, the retainer 341 can be slidably coupled to a track or the like defined by the front plate 311 (not shown in FIGS. 16-22) that can define a path along which the retainer 341 can be moved. More particularly, the retainer 341 can be slidably coupled to the front plate 311 and arranged for a substantially vertical movement (e.g., up and down) relative to the housing 310 while a substantially horizontal movement (e.g., left or right and/or at any other angle other than 90° relative to a horizontal axis) relative to the housing 310 is limited.

As shown in FIG. 18, the drive mechanism 345 includes a motor 346 and a lead screw 347. The motor 346 is fixedly coupled to the front plate 311 of the housing 310 and is configured to receive the lead screw 347. The lead screw 347 is rotatably coupled to the retainer 341 and can extend, at least partially, through the lead screw opening 316 defined by the second mounting portion 313 of the front plate 311. As such, the motor 346 can receive a signal (e.g., a flow of electrical current) from the power source 302 and/or the main PCB 302 that is operable in activating the motor 346 to rotate the lead screw 347 relative to the motor 346. Thus, with the motor 346 coupled (e.g., fixedly coupled) to the front plate 311, the rotational motion of the lead screw 347 advances the lead screw 347 in an axial direction relative to the motor 346 such that the retainer 341 is moved along the front surface of the front plate 3110. Similarly stated, the motor 346 can rotate the lead screw 347 to move the retainer 341 along a single axis that is normal to the motion of the reagent assembly 330, which is described above. In this manner, the motor 346 can rotate the lead screw 347, for example, in a forward (e.g., counterclockwise) direction to move the retainer 341 closer to the second mounting portion 312 of the front plate 311 and can rotate the lead screw 347, for example, in a backward (e.g., clockwise) direction to move the retainer 341 farther away from the second mounting portion 312.

As discussed above, in some embodiments, the lead screw 336 is fixed in position and does not rotate. In such embodiments, the motor 335 includes a nut (not shown) configured to rotate around the fixed lead screw and move the reagent tray as described above.

Figure 20:
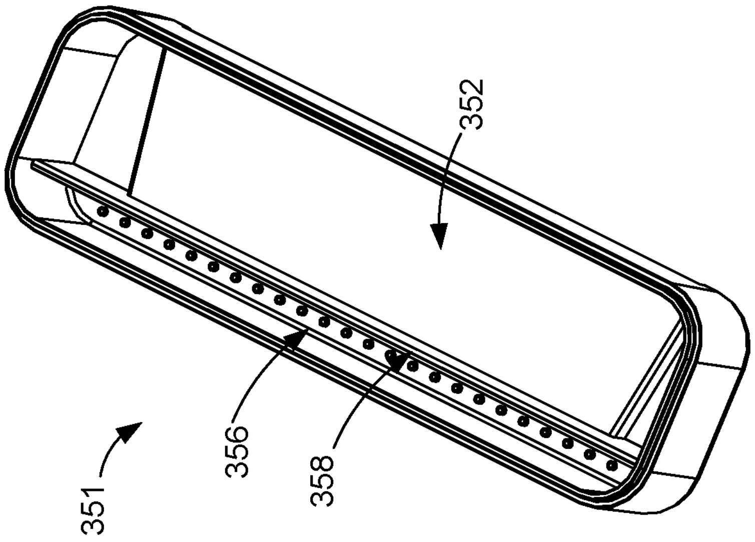
FIG. 20 is a perspective view of a portion of the cartridge of FIG. 19.
Figure 19:
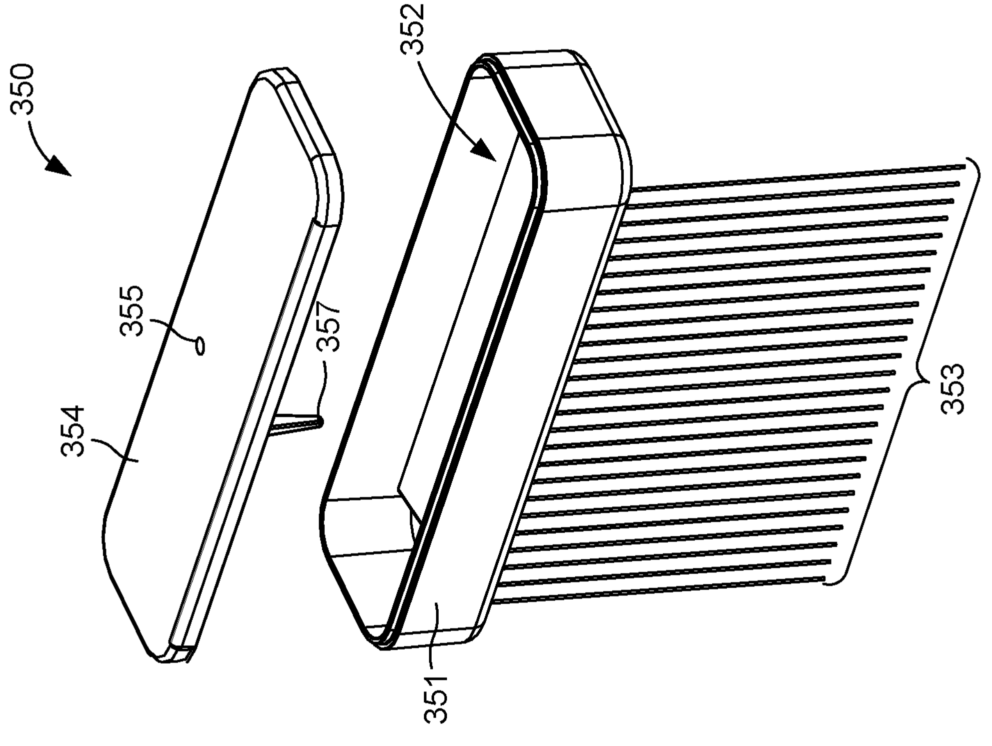
FIG. 19 is an exploded view of a cartridge included in the cartridge assembly of FIG. 16.

The cartridge 350 can be any suitable shape, size, or configuration. For example, as shown in FIGS. 19 and 20, the cartridge 350 includes a body portion 351 that is fixedly coupled to a set of flexible capillaries 353. The body portion 351 of the cartridge 350 defines a first reservoir portion 356 and a second reservoir portion 352 separated by a weir 358. More specifically, the body portion 351 is arranged such that the set of capillaries 353 coupled thereto are in fluid communication with the reservoir portion 352. For example, as shown, the body portion 351 can be substantially hollow, defining the reservoir portion 352 between a set of walls. Similarly stated, the body portion 351 can be bounded by the set of walls that extend from a base to define the reservoir 352 while allowing at least one side of the body portion 351 to remain substantially open (e.g., the body portion 351 has or defines a substantially U-shaped cross-section). As described in further detail herein, at least a part of the body portion 351 can be electrically conductive.

As shown in FIG. 19, the body portion 351 is coupled to a cap 354. The cap 354 can be coupled to the body portion 351 to substantially close the body portion 351, thereby substantially fluidically isolating the reservoir portion 352 from a volume outside of the body portion 351. The cap 354 defines an opening 355 (e.g., an aperture, a port, and/or the like) that can be operable in placing the reservoir portion 352 in fluid communication with a portion of the vacuum assembly 360 (see e.g., FIGS. 21 and 22), as described in further detail herein. In some embodiments, at least a portion of the cap 354 can be formed from an electrically conductive material such as, for example, a metal, a conductive plastic, a conductive composite, etc. Moreover, the cap 354 can be electrically coupled to the capillaries 353 such that a flow of current can be delivered from the cap 354 to the capillaries 353, as described in further detail herein.

A protrusion 357 extends from the body portion (i.e., from the cap 354 or some other portion of the body portion 351). In some embodiments, the protrusion 357 is monolithically formed with the body portion 351. In other embodiments, the protrusion 357 is separately manufactured, but coupled to, the body portion 351. The protrusion 357 is electrically conductive and is configured to produce a signal when the fluid level in the chamber contacts the protrusion 357 (e.g., a contact liquid level sensor). A voltage is applied to microtiter plate and when liquid contacts the electrically conductive protrusion 357, the current increases from, for example, zero, the liquid level is known. When fluid drawn through the capillaries contacts the protrusion 357, a known volume of fluid is known to exist within the first chamber portion 356. Because the elapsed time of fluid draw is known, the flow rate through the capillaries can be determined. The amount of liquid drawn past the top of the capillaries can then be determined. Knowing the volume of liquid above the capillaries enables the calculation of vacuum to draw in order to maintain the sample in the capillaries in a fixed position (i.e., the pressure is balanced). In some embodiments, electrokinetic loading is used to draw the reagents into the capillaries.

The vacuum drawn through the cartridge can be done using a single vacuum source 360 or multiple vacuum sources. For example, a first vacuum source can be used to draw the fluid through the capillaries and into the body portion and a second vacuum source can be used to maintain the vacuum in the body portion to maintain the sample in position in the capillaries. In embodiments in which multiple vacuum sources are used, the vacuum sources can be coupled to the cartridge through a single connector or multiple connectors.

In some embodiments, a sponge (not shown), or similar absorbent material, can be included in the second reservoir portion 352. The absorbent material is configured to stabilize any liquid in the body portion (i.e., prevent formation of bubbles and eliminate free-surface effects) and to inhibit leakage of liquid from the cartridge. The absorbent material may be adhered to the body portion or may be free standing within the body portion.

The set of capillaries 353 can be any suitable arrangement. For example, while the cartridge 350 is shown in FIG. 3 as including a set of 25 individual capillaries 353, in other embodiments, a cartridge can include any number of individual capillaries. For example, in some embodiments, a cartridge can include less than 25 individual capillaries or more than 25 individual capillaries. In some embodiments, the cartridge 350 can include a number of individual capillaries 353 that is related, at least in part, to a number of the wells 339 defined by the reagent tray 337. The capillaries 353 define a lumen (not shown in FIGS. 19 and 20) that can be configured to receive at least a portion of a sample, solution, reagent, analyte, and/or any other suitable fluid or gel, as described in further detail herein.

The capillaries 353 can be any suitable shape, size, or configuration and can be formed from any suitable material (e.g., glass, plastic, silicon, fused silica, gel, PYREX™ (amorphous glass), and/or the like) that allows a liquid and/or dissolved molecules to flow. In some embodiments, the shape and/or size of the lumen defined by the capillaries 353 can be any suitable shape and/or size and can at least partially correspond with the shape and/or size of the capillaries 353. For example, in some embodiments, the capillaries 353 can define a lumen having a diameter of about 30 micrometers (μm) to about 3000 μm. In other embodiments, a cartridge can include capillaries that define a lumen having a diameter of about 25 μm to about 400 μm. The size of the diameter of the lumen can be based at least in part on the sample and/or the sample volume. For example, a lumen with a relatively small diameter uses a relatively low sample volume, which can be suitable for expensive samples or reagents, whiles a lumen with a relatively large diameter uses a relatively high sample volume and can result in improved signal detection.

In some embodiments, the length of the capillaries 353 can be based at least in part on factors such as sample size and the extent of sample separation required to resolve the analyte or analytes of interest. In some embodiments, the capillaries 353 can have a length of about 2 to 20 centimeters (cm). In some embodiments, the capillaries 353 can have a length of less than 2 cm. In some embodiments, the capillaries 353 can have a length of about 3 cm, 4 cm, 5 cm, or 6 cm, or more. In some embodiments, the use of longer capillaries 353 can result in better separation of samples and improved resolution of complex mixtures and/or when resolving a low abundance analytes.

In some embodiments, the length of the capillaries 353 and the range of motion of the retainer 341 (e.g., the length of travel of the retainer 341 relative to the housing 310) can be substantially related. For example, the cartridge assembly 340 can move in a direction toward the reagent assembly 330 (e.g., away from the second mounting portion 312 of the front plate 311) to dispose an end portion of the capillaries 353 in the wells 339 of the reagent tray 337. In addition, the holder 331 can be moved in a perpendicular direction relative to the retainer 341 and the cartridge 350 to selectively position a portion of the wells 339 relative to the cartridge 350. For example, the reagent assembly 330 can be in a first position relative to the cartridge assembly 340 and the cartridge assembly 340 can be in a first position relative to the reagent assembly 330 to place an end portion of the capillaries 353 of the cartridge 350 in a first set of wells defined by the reagent tray 337. In some instances, the retainer 341 can be moved (e.g., away from the reagent assembly 330 and toward the second mounting portion 312) to a second position relative to the holder 331 to remove the capillaries 353 of the cartridge 350 from the wells 339 of the reagent tray 337. In some instances, the holder 331 can then be moved to a second position relative to the cartridge assembly 330 and the retainer 341 can again be placed in the first position relative to the reagent assembly 330 to place the end portion of the capillaries 353 of the cartridge 350 in a second set of wells. Thus, the retainer 341 and the holder 331 can be moved in a predetermined and related manner to place the capillaries 353 of the cartridge 350 in any suitable well 339 or set of wells 339 defined by the reagent tray 337.

Figure 21:
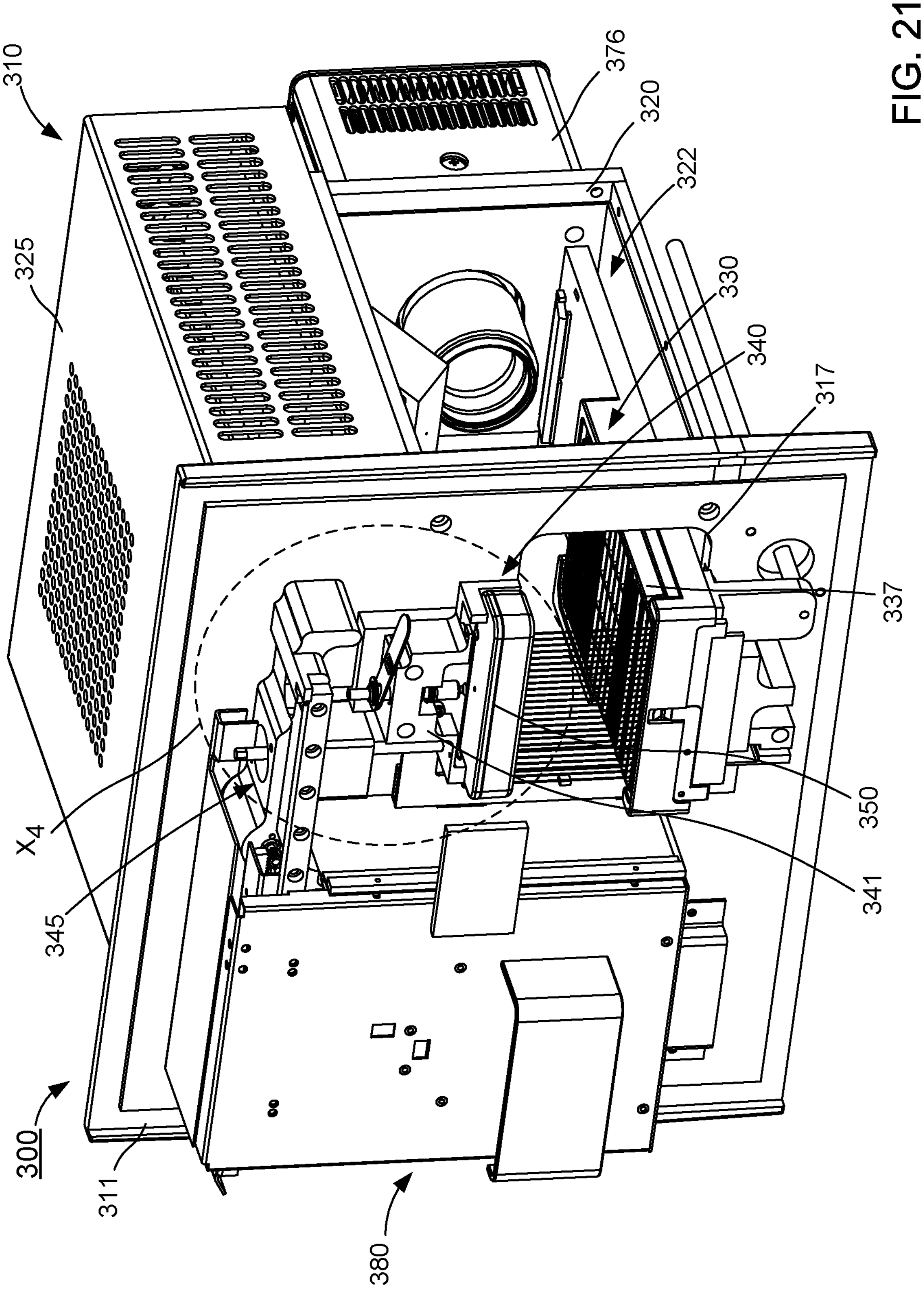
FIG. 21 is a perspective view of the capillary electrophoresis system of FIG. 3, illustrating a portion of the cartridge assembly and a portion of a vacuum assembly.
Figure 22:
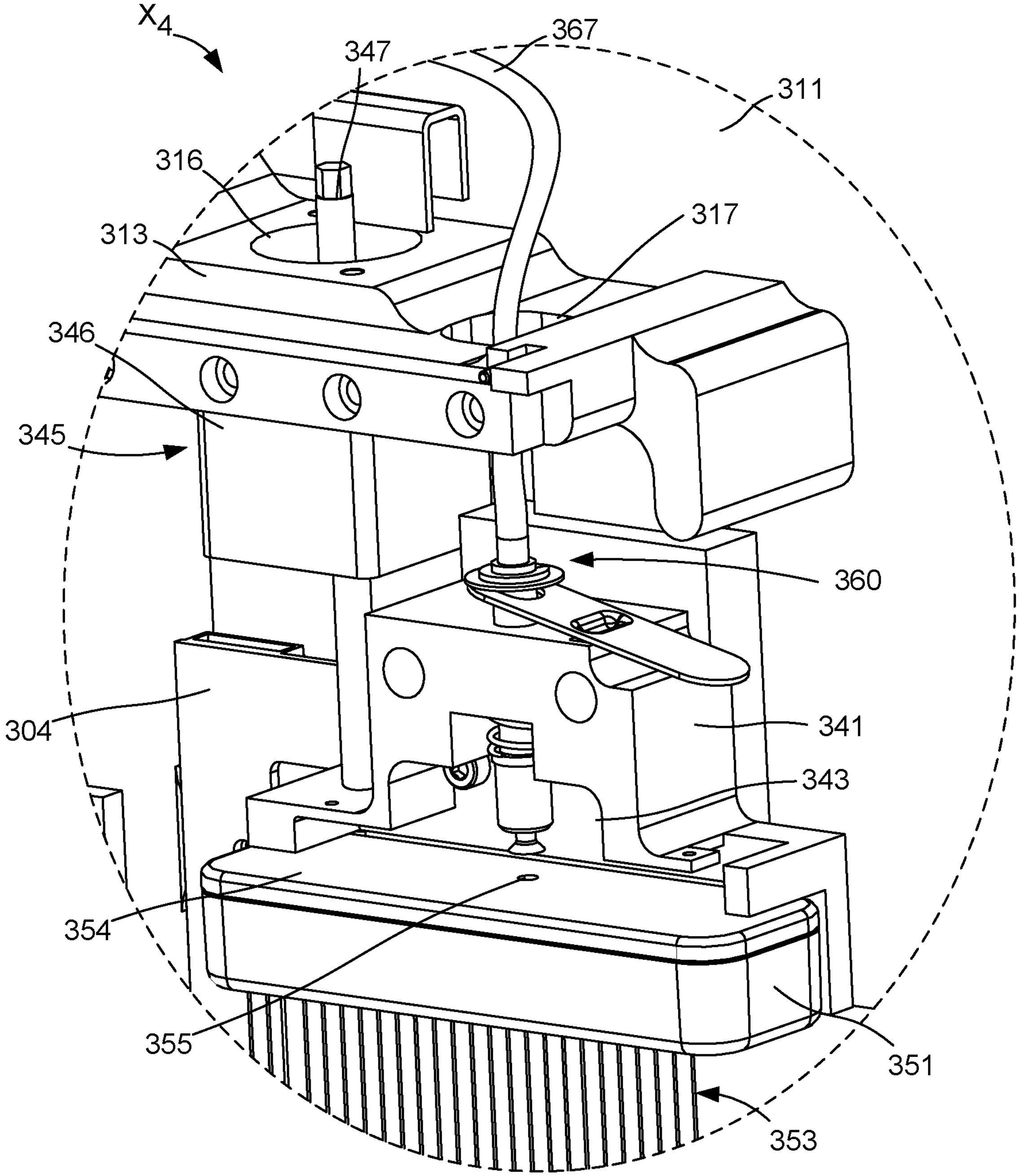
FIG. 22 is an enlarged view of the capillary electrophoresis system of FIG. 3, identified as the region $X_4$ in FIG. 21 and illustrating the portion of the cartridge assembly and the portion of the vacuum assembly.
Figure 23:
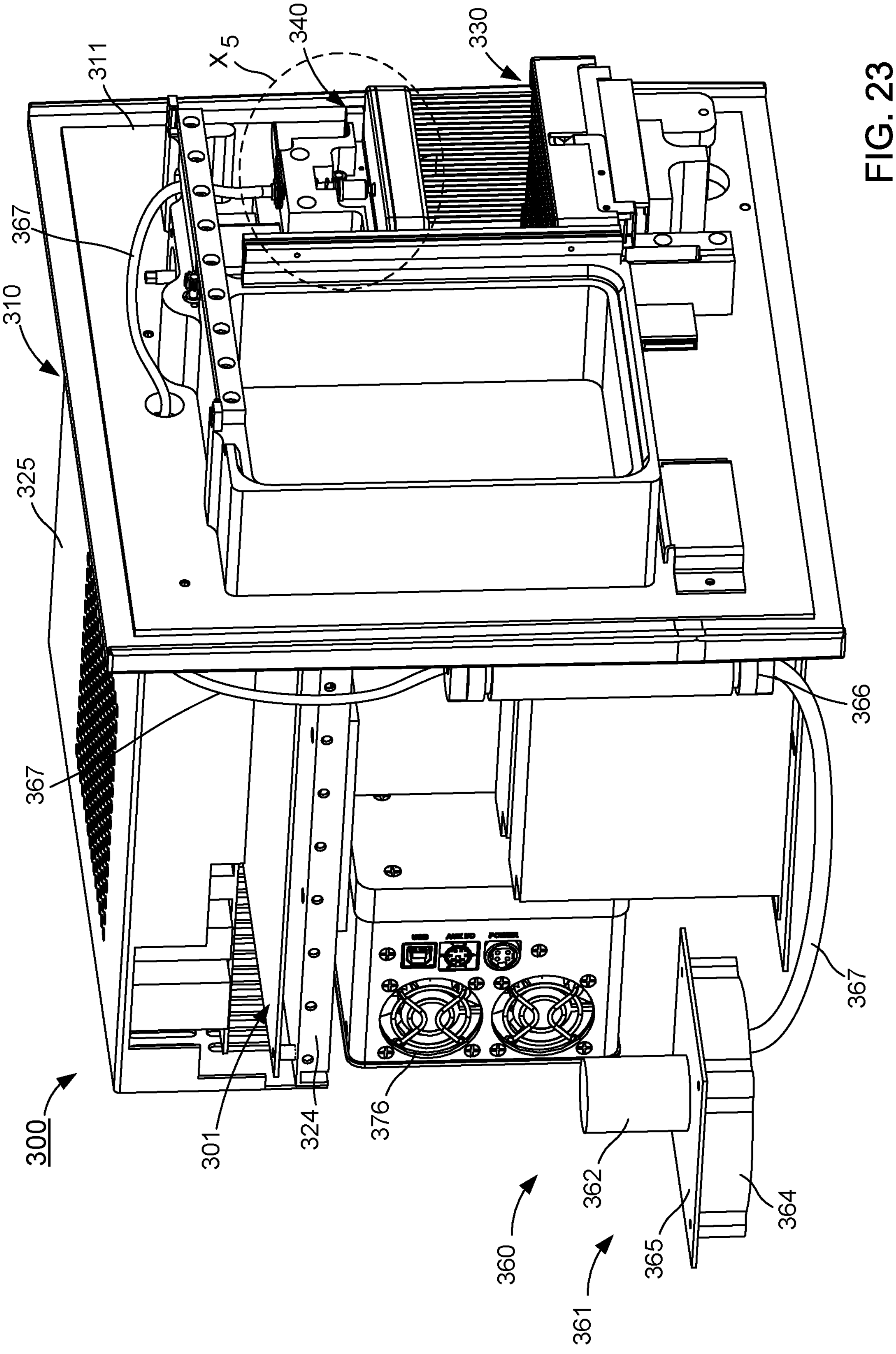
FIG. 23 is a left perspective view of the capillary electrophoresis system of FIG. 3.

As shown in FIGS. 21-25, the vacuum assembly 360 can be any suitable device or mechanism that is configured to produce a negative pressure within a volume, thereby applying a suction force to at least a portion of the volume. For example, as shown in FIGS. 21 and 22, the vacuum assembly 360 includes a vacuum source 361, a vacuum chamber 366, a hose assembly 367, a first engagement member 368, and a second engagement member 370. As shown in FIG. 23, the hose assembly 367 is configured to extend between components of the vacuum assembly 360 to place the components in fluid communication with each other. For example, a hose is physically and fluidically coupled to the vacuum source 361 and the vacuum chamber 366 and a second hose is physically and fluidically coupled to the vacuum chamber 366 and the first engagement member 368, as described in further detail herein.

Figure 24:
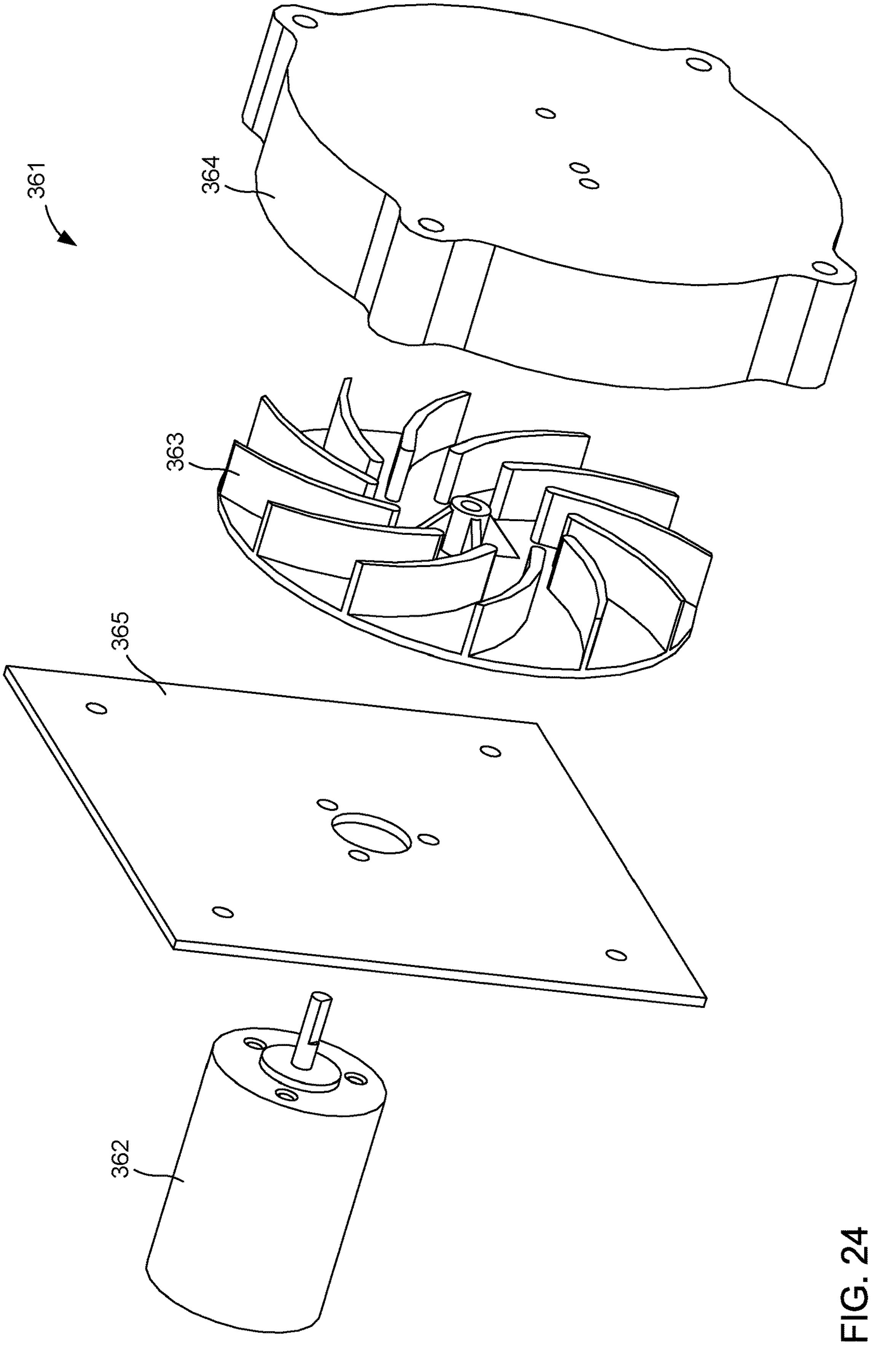
FIG. 24 is an exploded view of a portion of the vacuum assembly of FIG. 21 included in the capillary electrophoresis system of FIG. 3.

As shown in FIG. 24, the vacuum source 361 includes a motor 362, an impeller 363, a housing 364, and a cap 365. The impeller 363 is rotatably disposed within an inner volume (not shown in FIG. 21-25) of the housing 365 and is coupled to an output shaft of the motor 362. The cap 365 is coupled to the housing 365 to substantially fluidically isolate the inner volume of the housing 364 from a volume outside of the housing 364. The motor 362 is fixedly coupled to the cap 365 in such a manner as to allow the output shaft to extend through the cap 365 to be coupled to the impeller 363. As such, the motor 362 can receive a flow of current from the power source 302 and/or the main PCB 303 that can be operable in activating the motor 362 to rotate the impeller 363 within the inner volume. Furthermore, with the hose assembly 367 fluidically coupling the vacuum source 361 to the vacuum chamber 366, the rotation of the impeller 363 produces a negative pressure within the inner volume of the housing which exerts a suction force on the vacuum chamber 366. Thus, when the motor 362 is activated to rotate the impeller 363 a negative pressure is produced within the vacuum chamber 366.

Figure 25:
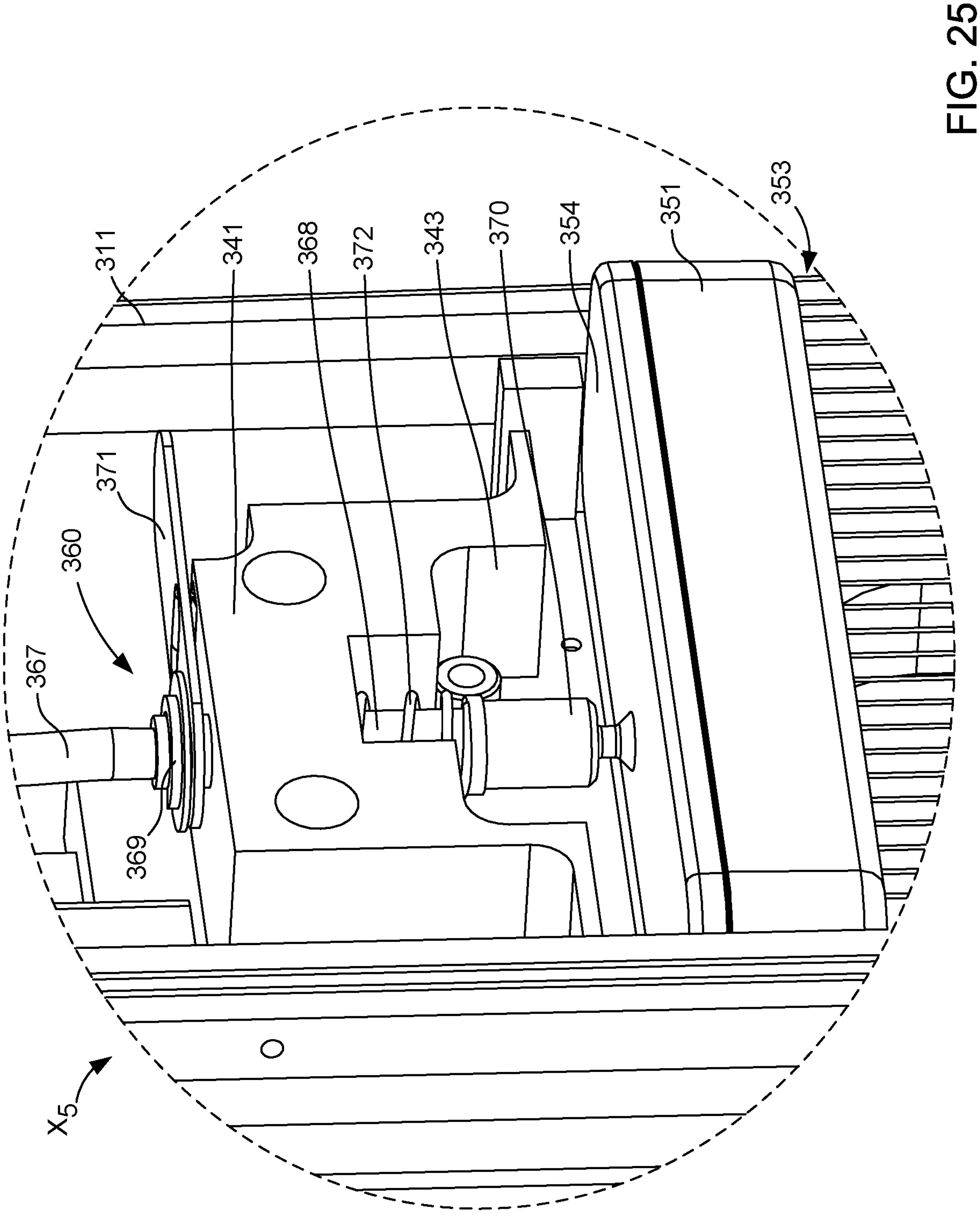
FIG. 25 is an enlarged view of a portion of the capillary electrophoresis system identified as the region $X_5$ in FIG. 23 and illustrating a portion of the vacuum assembly and a portion of the cartridge assembly.

As shown in FIGS. 21 and 25, the first engagement member 368 and the second engagement member 370 are physically and fluidically coupled together and arranged such that at least a portion of the second engagement member 370 is disposed within the recess 343 defined by the retainer 341. The first engagement member 368 includes a retaining clip 369 that is configured to engagement an actuator 371 or the like. For example, the actuator 371 can be a lever that can be operable in moving the first engagement member 368 and the second engagement member 370 between a first position relative to the retainer 341 and a second position relative to the retainer 341. Although not shown in FIGS. 21-25, the vacuum assembly 360 and/or any other component of the system 300 can include an activator that can be selectively placed in contact with the actuator 371 to transition the actuator 371 between a first configuration, which is associated with the engagement members 368 and 370 in the first position, and a second configuration, which is associated with the engagement members 368 and 370 in the second position. In some embodiments, actuator 371 is a passive actuator in that it opens and closes the vacuum based on position of plunger actuation.

As shown in FIG. 21, the vacuum assembly 360 is configured such that when the engagement members 368 and 370 are in the first position, the second engagement member 370 is spaced apart from the cap 354 of the cartridge 350. Thus, the vacuum assembly 360 is fluidically isolated from the cartridge 350. As shown in FIG. 25, the vacuum assembly 360 is configured such that when the engagement members 368 and 370 are in the second position, the second engagement member 370 is placed in contact with the cap 354 of the cartridge 350. Moreover, the vacuum assembly 360 can be arranged such that when in the second position, the second engagement member 370 is placed in fluid communication with the reservoir 352 defined by the body portion 351 via the opening 355 defined by the cap 354. Therefore, when a negative pressure is produced in the vacuum chamber 366, the second engagement member 370 can expose the reservoir 352 to a suction force, as described in further detail herein. As shown in FIGS. 21 and 25, the vacuum assembly 360 includes a bias member 372 that is configured to maintain the engagement members 368 and 370 in the first position relative to the retainer 341 until the actuator 371 is transitioned from the first configuration to the second configuration.

As shown in FIGS. 26-30, the light assembly 380 of the system 300 includes a cover assembly 381, a light source 386, and a drive mechanism 387. The cover assembly 381 includes an outer cover 382, and inner cover 383, a spacer 384, and an ultraviolet light blocker 385 (also referred to herein as "UV blocker"). As shown in FIG. 26, the light PCB 307 can be included in and/or can otherwise be electrically coupled to a portion of the light assembly 307. In this manner, the light PCB 307 can control at least a portion of the light assembly 380. Moreover, the light PCB 307 can be in electrical communication with the main PCB 303 and can send a signal to and/or receive a signal from the main PCB 303 associated with the functioning of the light assembly 380.

The cover assembly 381 is coupled to the light 386 and the drive mechanism 387 and is configured to block and/or otherwise direct light emitted from the light source 386. The spacer 384 included in the cover assembly 381 is configured to space the cover assembly 381 a desired distance from the light source 386 such as to not interfere with the light source 386 and/or any other structure such as, for example, the front plate 311 of the housing 310.

The light source 386 can be any suitable device, member, mechanism, assembly, and/or the like that is configured to release energy (e.g., heat, photons, radiation, etc.). For example, in some embodiments, the light source 386 can be a UV grid lamp. In this manner, the light source 386 can include an element that can be excited (e.g., powered) to emit photons. By way of example, the light source 386 can be a low-pressure mercury lamp that generates light (e.g., photons) at a first wavelength of about 254 nm. In some embodiments, the light source 386 can include a phosphor coating to convert the first wavelength of about 254 nm to a second wavelength of about 295 nm. In this manner, the light source 386 can emit energy that can interact with at least a portion of a sample contained within the capillaries 353 of the cartridge 350.

The light assembly 380 is movably coupled to the second mounting portion 313 of the front plate 311 to allow the drive mechanism 387 to move the light assembly 380 between a first position and a second position relative to the cartridge assembly 340. More particularly, the light assembly 380 can be moved in a direction that is perpendicular (e.g., normal) to the movement of the cartridge retainer 341 when moved between its first position and its second position and that is perpendicular to the movement of the reagent tray holder 330 when moved between its first position and its second position (e.g., the light assembly 380 can move along an X-axis of an orthogonal coordinate system, the reagent tray holder 330 can move along a Y-axis of the orthogonal coordinate system, and the cartridge retainer 341 can move along a Z-axis of the orthogonal coordinate system). Moreover, the light assembly 380 can be arranged relative to the housing 310 as to be disposed on a second side of the cartridge retainer 341. In this manner, the cartridge assembly 340 is disposed between the detection assembly 375 (described above) and the light assembly 380.

Figure 27:
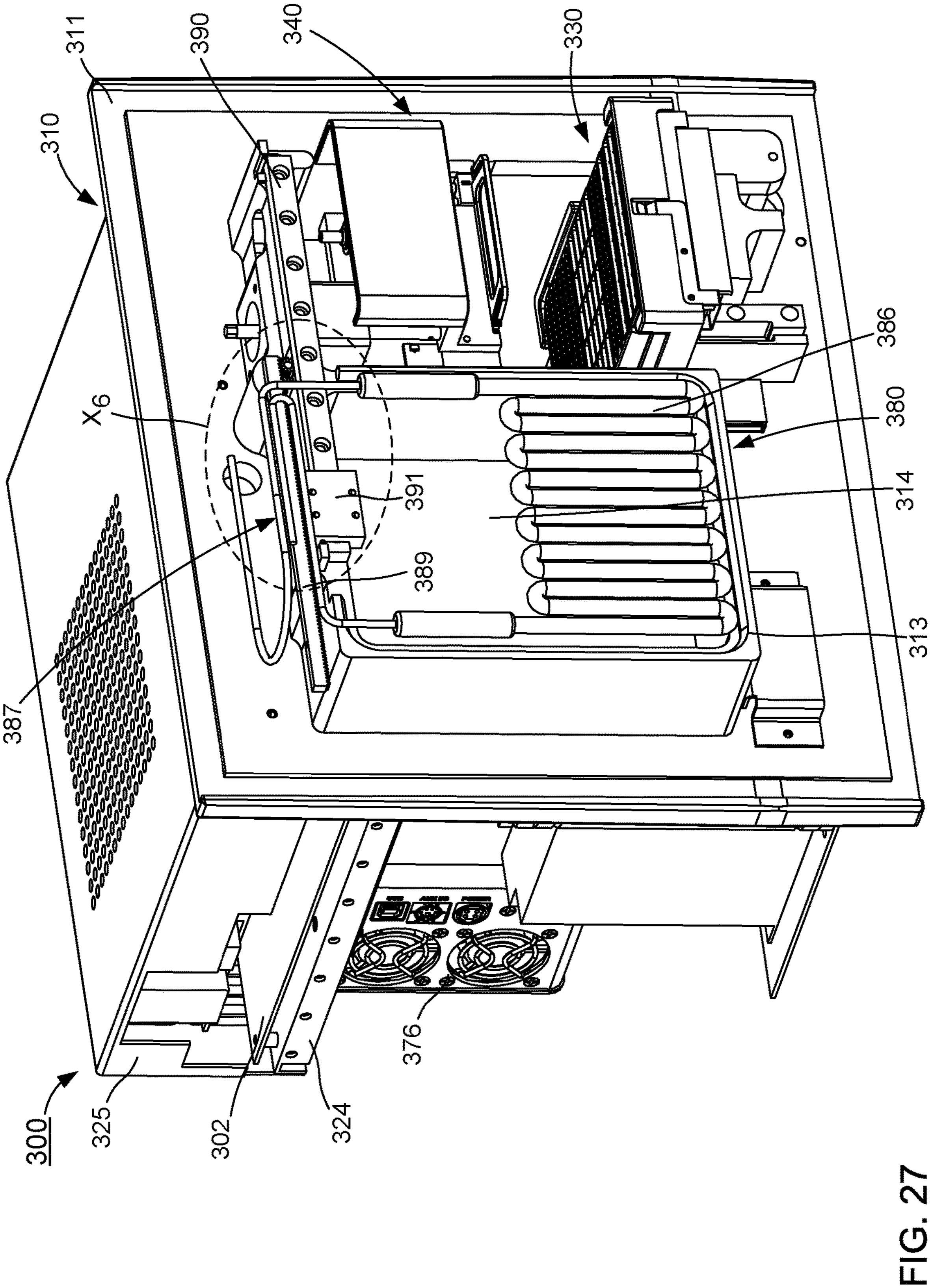
FIG. 27 is a left perspective view of the capillary electrophoresis system of FIG. 3, illustrating a portion of the light assembly of FIG. 26.
Figure 28:
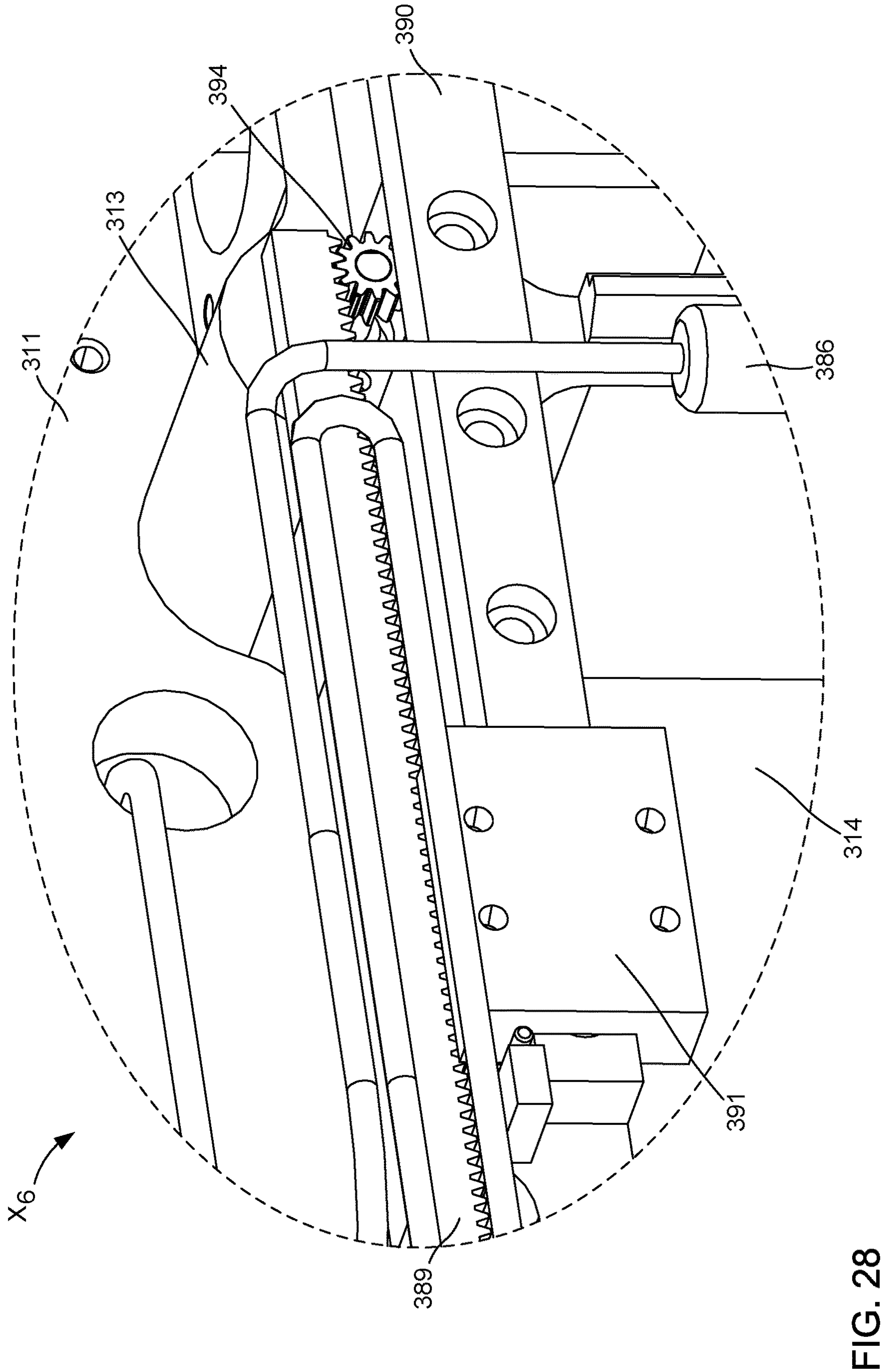
FIG. 28 is an enlarged view of a portion of the capillary electrophoresis system identified as the region $X_6$ in FIG. 27.
Figure 29:
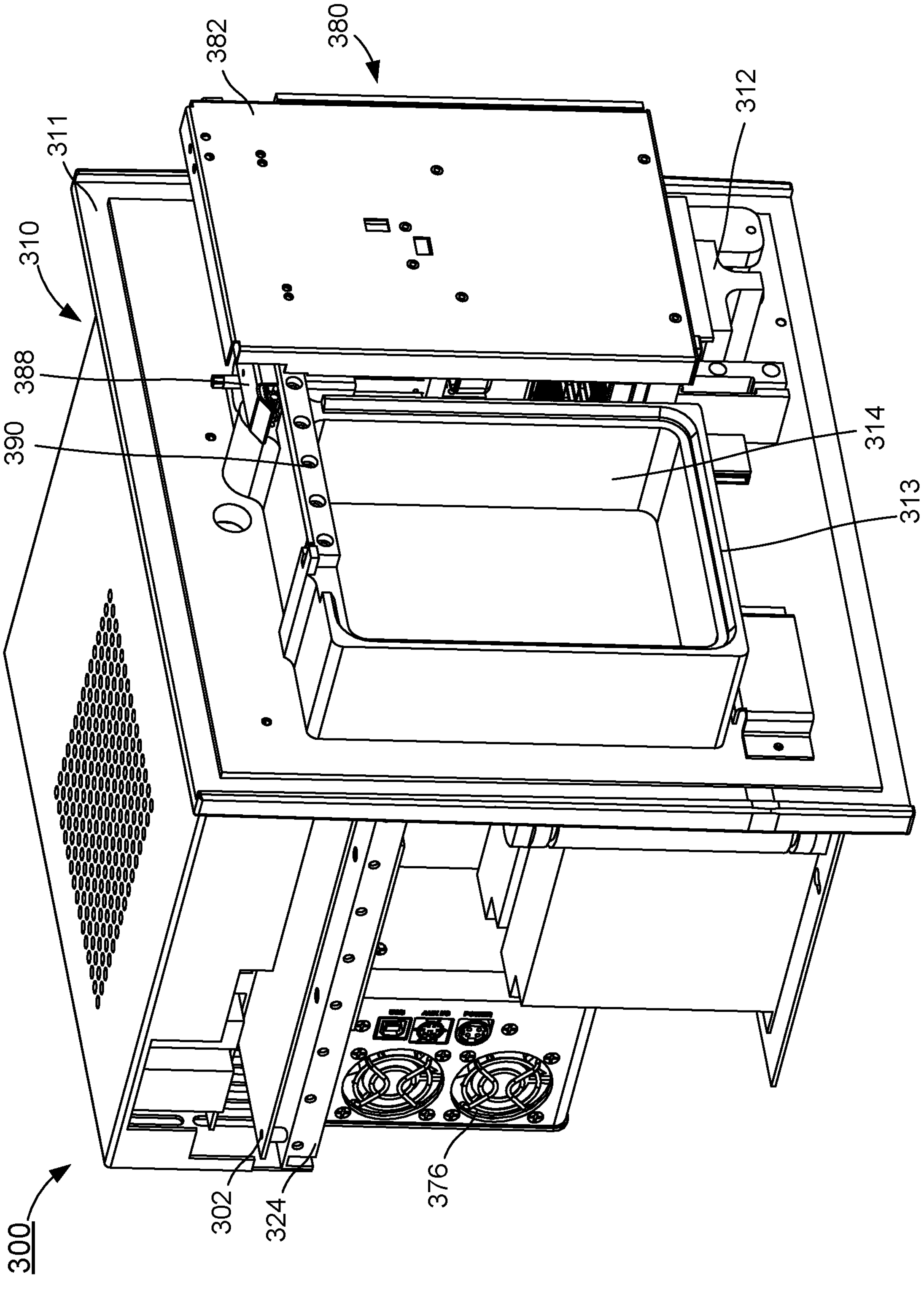
FIG. 29 is a left perspective view of the capillary electrophoresis system of FIG. 3, illustrating the light assembly of FIG. 26 in a second position.
Figure 30:
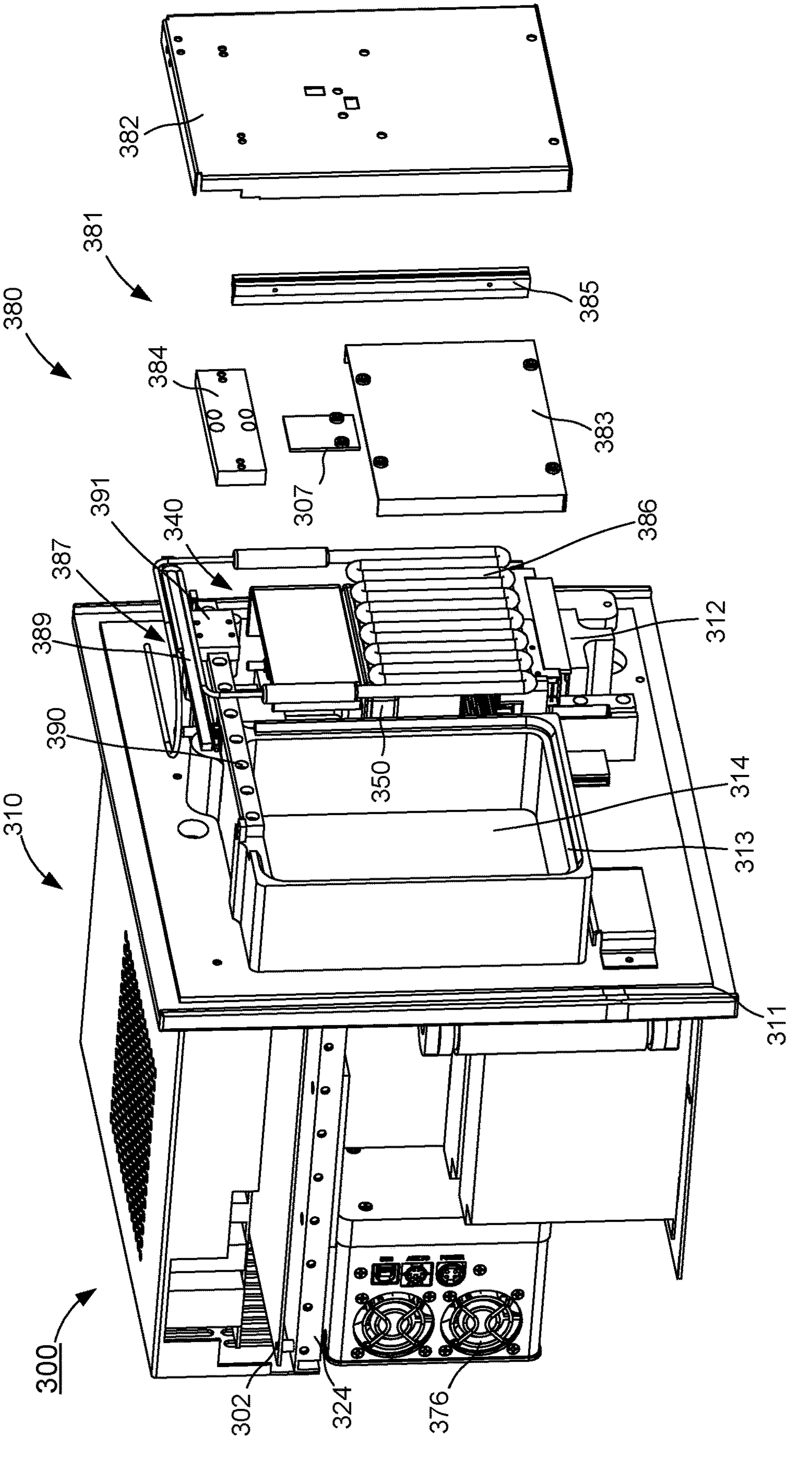
FIG. 30 is a partially exploded view of the capillary electrophoresis system of FIG. 3, illustrating the light assembly of FIG. 26 in the second position.

As shown in FIGS. 26-28, the drive mechanism 387 includes a rack mount 388, a rack 389, a guide track 390, a guide block 391, and a drive gear 394. Although not shown in FIGS. 3-31, the drive gear 393 of the drive mechanism 387 is coupled to an output shaft of a motor (not shown) that is fixedly disposed within the housing 310. In this manner, the motor can receive a signal from, for example, the main PCB 303 that is operable in activating the motor, as described in further detail herein. As shown in FIG. 27, the guide track 390 is coupled to the second mounting portion 313 of the front plate 311 and is configured to extend in a substantially lateral direction. The rack mount 388 is coupled to the rack 389 and the cover assembly 381. In addition, the rack mount 388 is coupled to the guide block 391, which is slidably disposed about a portion of the guide track 390. Thus, the light assembly 380 is slidably coupled to the guide track 390 and can be moved between the first position and the second position. More specifically, the rack 389 includes a set of teeth that are configured to engage and/or mesh with the drive gear 393 coupled to the output shaft of the motor. Thus, the motor can receive a signal from the main PCB 303 and/or the power source 302 that is operable in activating the motor such that the drive gear 393 is rotated. With the rack 389 engaging the drive gear 393, the rotation of the drive gear 393 advances the rack 389 relative to the drive gear 393, thereby moving the light assembly 380 between the first position (see e.g., FIGS. 26-28) and the second position (see e.g., FIGS. 29 and 30) relative to the cartridge assembly 340. In this manner, the light assembly 380 can be moved to the second position and the light source 386 can be energized to emit photons and/or heat that can interact with a sample disposed within the capillaries 353 of the cartridge 350, as described in further detail herein.

As described above, the system 300 can be configured to separate, immobilize, and analyze a sample in at least a semi-automated process. For example, a user can prepare, for example, the reagent tray 337 by disposing any suitable sample, protein, analyte, buffer, lysate, standard, agent, reagent, and/or the like into one or more wells 339. The reagent tray 337 can then be disposed between the walls 332 of the holder 331 such that movement of the reagent tray 337 relative to the holder 331 is substantially limited. With the reagent tray 337 loaded into the holder 331, the user can insert the cartridge 350 into the cartridge retainer 341 such that movement of the cartridge 350 relative to the retainer 341 is substantially limited, as described above. While described above as loading the reagent tray 337 prior to the cartridge 350, in other instances, the cartridge 350 can be loaded into the cartridge retainer 341 prior to the reagent tray 337 being loaded into the holder 331.

With the cartridge 350 and the reagent tray 337 loaded, a user can activate the system 300 to perform at least a semi-automatic immunoassay. For example, the user can toggle an on/off switch, engage a user interface such as a touch screen, mouse, keyboard, or the like, and or otherwise transition the system 300 from an off configuration (e.g., not powered) to an on configuration (e.g., powered). Although described above as turning on the system after the cartridge 350 and the reagent tray 337 are loaded, in other instances, the system 300 can be turned on prior to the cartridge 350 and/or the reagent tray 337 being loaded.

With the reagent tray 337 and the cartridge 350 loaded into the holder 331 and the retainer 341, respectively, and with the system 300 turned on, the system 300 can move the reagent assembly 330 to a first position relative to the cartridge assembly 340, as described in detail above. Moreover, the cartridge assembly 330 can be in its second position while the reagent assembly 330 is moved into its first position such that the capillaries 353 are separated from the reagent tray 337 by a suitable distance. Similarly stated, the cartridge assembly 330 can be disposed in its second position to provide a sufficient clearance between the capillaries 353 and the reagent assembly 330.

With the reagent assembly 330 in the first position, the cartridge retainer 341 can be moved toward its first position relative to the reagent holder 330 to place the capillaries 353 of the cartridge 350 in fluid communication with one or more wells 339 defined by the reagent tray 337. Once the capillaries 353 are placed in fluid communication with a sample (e.g., any of those described herein) disposed in the one or more wells 339, the system 300 can actuate the actuator 371 of the vacuum assembly 360 to move the second engagement member 370 into contact with the cap 354 of the cartridge 350. Thus, the reservoir 352 of the body portion 351 and the capillaries 353 are placed in fluid communication with the vacuum source 361. In this manner, the main PCB can send a signal to the vacuum source 361 that is operable in activating the motor 362 such that a negative pressure is produced within the vacuum chamber 366. The negative pressure, in turn, can be such that a suction force is exerted through the capillaries 353 to selectively draw one or more reagents, samples, buffers, washes, detectors, analytes, ampholytes, agents, and/or the like into the lumen defined by the capillaries 353. As described above, the cartridge retainer 341 and the reagent tray holder 341 can be moved in a related manner to selectively place the capillaries 353 of the cartridge 350 in a desired set of wells 339 defined by the reagent tray 337 to fill the lumen of the capillaries 353 with a sample having a desired set of constituents.

Once a mixture (e.g., a sample) having desired constituents is drawn into the lumen defined by the capillaries 353 of the cartridge 350, the system 300 can apply an electric field to an electrically conductive portion of the cartridge 350. For example, the system 300 can apply and an electric field to the cap 354 of the body portion 351 which, in turn, can apply an electric field to the capillaries 353. In some instances, the electric field can be generated by, for example, the cartridge PCB 306 (FIG. 18). In other instances, the electric field can be generated by the power supply 302 and/or the main PCB 303 in electrical communication with the cap 354 via one or more wires (not shown). Thus, electrical current can flow to the set of capillaries 353 of the cartridge 350 to perform, for example, electrophoresis on the sample disposed therein. More particularly, the flow of electrical current to the capillaries 353 can initiate capillary electrophoresis, wherein analytes in the sample disposed within the capillaries 353 of the cartridge 350 are separated along a size gradient (e.g., along a length of each capillary 353), as described in detail above.

Once the molecules are sufficiently separated, the system 300 can be configured to immobilize the molecules within the capillaries of the cartridge 350. For example, the system 300 can send a signal to the motor of the light assembly 380 that is operable in activating the motor. In this manner, the light assembly 380 can be moved from its first position (e.g., not aligned with the cartridge 350) to its second position (e.g., substantially aligned with the cartridge 350) relative to the cartridge 350. In this manner, the light source 386 can be activated (e.g., switched on by supplying electric current to the light source 386 via, for example, the light PCB 307, the power source 302, and/or the main PCB 303), thereby emitting photons that can interact with at least a portion of the separated sample disposed in the capillaries 353 of the cartridge 350. The interaction of the separated sample with the photons emitted by the light source 386 can be such that the at least a portion of the separated sample binds to the walls of the capillaries 353 to become immobilized, as described in detail above.

With the analytes separated and immobilized, the immobilized analytes and/or standards include in the sample are probed with a detection agent (e.g., any suitable agent, reagent, analyte-specific antibody, horseradish peroxidase (HRP)-conjugated secondary antibody, and/or the like or any combination thereof, as described in detail above). For example, in some instances, the retainer 341 and the holder 331 can move in a related manner to dispose the capillaries 353 in a well containing the detection agent. Thus, the detection agent can be draw into the capillaries 353 by again activating the vacuum source 361, as described above. In some embodiments, the detection agent can be provided via any other suitable process. In this manner, the detection agent is used to create a signal from one or more label moieties (e.g., isotopic labels, immune labels, optical dyes, enzymes, particles or combination of particles such as chemiluminescent-labeled antibodies, fluorescent-labeled antibodies, and/or the like) that can be detected by the optical detector 375 and/or the scanner 378 (FIG. 31) and graphed as signal vs. length of the capillary 353. In some embodiments, the signal can be measured from at least two different time points. In some embodiments, the signal can be monitored continuously or at several selected time points. Alternatively, the signal can be measured at an end-point, in which a signal is measured after a certain amount of time, and the signal is compared against a control signal (sample without analyte), threshold signal, or standard curve. In addition, the signal from a standard can be used to interpret the signal from the analyte. In some embodiments, a signal from the analyte and/or the standard can be at least 2-fold greater than the background. In some embodiments, a signal between 2 to 20-fold greater than the background can be generated. In some embodiments, a signal can be 20-fold greater than the background. Thus, the system 300 can be used to at least semi-automatically draw a sample into a set of capillaries, separate analytes within a sample, immobilize the analytes, detect the separated analytes, and report the detection of the analytes.

During and after the assay process, any of the reagents, samples, buffers, washes, detectors, analytes, ampholytes, agents, etc. that get drawn through the capillaries are collected in reservoir 352. Upon completion of the assay process, the entire cartridge 350 can be decoupled from the vacuum source and discarded. In this manner, a separate waste collection bin (either internal to the device or external) is not required. In other words, the individual cartridge 350 used in connection with each assay is a single use, disposable cartridge that is not necessarily fluidically coupled to a separate waste collection source.

Figure 32:
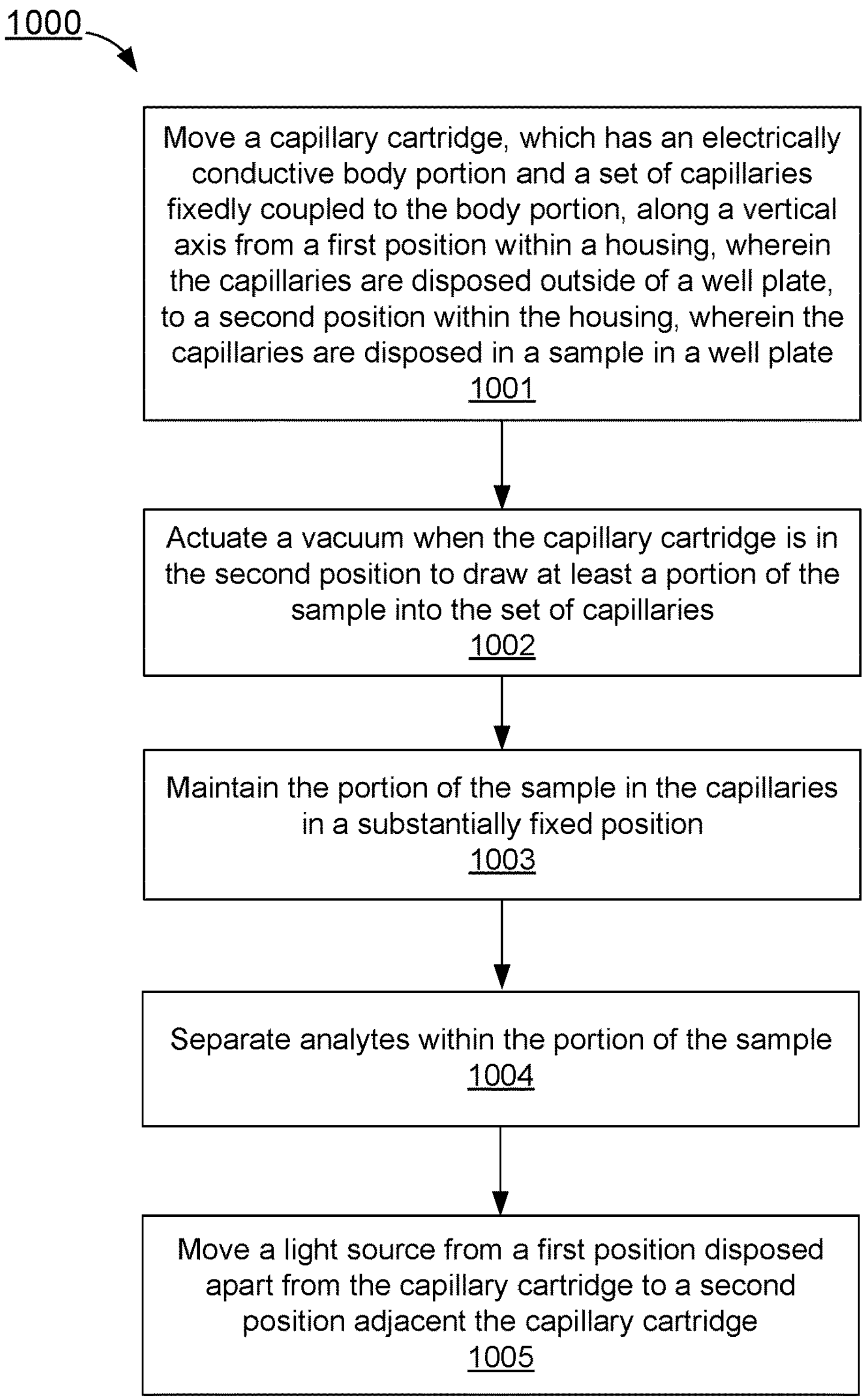
FIG. 32 is a flowchart illustrating a method of using a capillary electrophoresis system according to an embodiment.

FIG. 32 is a flowchart illustrating a method 1000 of using a capillary electrophoresis system according to an embodiment. The method 1000 can be used with any of the systems 100, 200, and/or 300 described herein. The method 1000 includes moving a capillary cartridge, which has an electrically conductive body portion and a set of capillaries fixedly coupled to the body portion, along a vertical axis from a first position within a housing, wherein the capillaries are disposed outside of a well plate, to a second position within the housing, wherein the capillaries are disposed in a sample in the well plate, at 1001. For example, the capillary cartridge can be coupled to and/or retained by a cartridge retainer that is slidably coupled to a portion of the housing. The well plate can be any suitable tray or the like. For example, in some embodiments, the well plate can be substantially similar to or the same as the reagent tray 330 described above with reference to FIGS. 3-31. In such embodiments, the reagent tray (e.g., the well plate) can be disposed in a holder or the like that can be moved relative to the cartridge retainer to expose the capillaries to more than one set of wells.

When the capillary cartridge is in the second position a vacuum is actuated to draw at least a portion of the sample into the set of capillaries, at 1002. For example, in some embodiments, the capillary cartridge can include a port or opening that can be selectively place in fluid communication with a vacuum source. In some embodiments, the vacuum source can be, for example, substantially similar to or the same as the vacuum source 361 described above with reference to FIG. 24. In this manner, the vacuum source can produce a negative pressure within a lumen defined by each capillary that can exert a suction force that draws the portion of the sample into the capillaries.

The portion of the sample in the capillaries is maintained in a substantially fixed position, at 1003. For example, the vacuum source can supply a substantially constant negative pressure. The method 1000 includes separating analytes within the portion of the sample, at 1004. For example, in some embodiments, an electric field can be applied to the conductive body portion such that a flow of electric current is transferred to the capillaries. In this manner, the analytes can separate within the portion of the sample be capillary electrophoresis (e.g., an electrophoresis technique). With the analytes separated within the portion of the sample, the light source can be activated to emit photons that can interact with the portion of the sample disposed in the capillaries to bind, at least temporarily, the analytes to the walls of the capillaries. The method 1000 includes moving the light source from a first position disposed apart from the capillary cartridge to a second position adjacent the capillary cartridge, at 1005. The light source can be any suitable source of light such as the light source 386 described above with reference to FIGS. 26-30. For example, the light source can be a UV grid light or the like. With the analytes substantially immobilized, the analytes can be detected using any suitable detecting agent and an optical detector, as described above with reference to the system 300.

In some embodiments, reagents, reagent trays, capillary cartridges, and/or the like can be packaged separately or can be packaged collectively as, for example, kits for analyte detection using any of the systems or methods described herein. In some embodiments, a kit can include materials for making an electrophoresis and/or a capillary electrophoresis standard(s) such as those described herein. Additionally, one or more mobility moieties, one or more reactive moieties, one or more label moieties can be packaged independently or collectively. In some embodiments, a kit can include one or more electrophoresis standards including a peptide, one or more fluorescent dyes, and one or more photoreactive groups. In addition, buffers, polymeric or polymerizable materials, blocking solutions, and washing solutions can be packaged together with a reagent, reagent tray, capillary cartridge, etc. or can be packaged independently from the reagent, the reagent tray, the capillary cartridge, etc. Components can be provided separately from each other or mixed together in dry or liquid form.

Some embodiments described herein relate to a computer storage product with a computer-readable medium (also can be referred to as a processor-readable medium) having instructions or computer code thereon for performing various computer-implemented operations. The media and computer code (also can be referred to as code) may be those designed and constructed for the specific purpose or purposes. Examples of computer-readable media include, but are not limited to: magnetic storage media such as hard disks, floppy disks, and magnetic tape; optical storage media such as Compact Disc/Digital Video Discs (CD/DVDs), Compact Disc-Read Only Memories (CD-ROMs), and holographic devices; magneto-optical storage media such as optical disks; carrier wave signal processing modules; and hardware devices that are specially configured to store and execute program code, such as Application-Specific Integrated Circuits (ASICs), Programmable Logic Devices (PLDs), and Read-Only Memory (ROM) and Random-Access Memory (RAM) devices.

Examples of computer code include, but are not limited to, micro-code or micro-instructions, machine instructions, such as produced by a compiler, code used to produce a web service, and files containing higher-level instructions that are executed by a computer using an interpreter. For example, embodiments may be implemented using Java, C++, or other programming languages (e.g., object-oriented programming languages) and development tools. Additional examples of computer code include, but are not limited to, control signals, encrypted code, and compressed code.

While various embodiments have been described above, it should be understood that they have been presented by way of example only, and not limitation. Where schematics and/or embodiments described above indicate certain components arranged in certain orientations or positions, the arrangement of components may be modified. For example, while the light assembly 380 of the system 300 is shown in FIGS. 3-31 as moving in a lateral direction relative to the cartridge assembly 340, in other embodiments, a light assembly can be moved along a similar axis as a cartridge assembly between a first position, in which the light assembly is spaced apart from the cartridge assembly, to a second position, in which the light assembly is adjacent the cartridge assembly. While the embodiments have been particularly shown and described, it will be understood that various changes in form and details may be made. Although various embodiments have been described as having particular features and/or combinations of components, other embodiments are possible having a combination of any features and/or components from any of embodiments as discussed above.

Where methods and/or events described above indicate certain events and/or procedures occurring in certain order, the ordering of certain events and/or procedures may be modified. For example, although described separating the analytes within the portion of the sample (e.g., step 1005 in FIG. 32) is shown and described as occurring after the step 1004, in other embodiments, the analytes can be separated within the portion of the sample prior to the light source being moved from a first position to a second position. Additionally, certain of the events may be performed concurrently in a parallel process when possible, as well as performed sequentially as described above.

What is claimed is:

1. An apparatus, comprising:

a body defining a reservoir; wherein the reservoir includes a first portion and a second portion separated from the first portion by a weir;

an absorbent material positioned within the second portion;

a capillary fixedly coupled to the body and in fluid communication with the reservoir; wherein a first end of the capillary is positioned in the first portion of the reservoir;

a cap coupled to the body; wherein the cap includes an opening in fluid communication with the reservoir and the capillary; and a contact liquid level sensor extending into the reservoir.

2. The apparatus of claim 1, wherein the contact liquid level sensor comprises a protrusion extending from the cap.

3. The apparatus of claim 2, wherein the protrusion is electrically conductive and configured to produce a signal when a fluid level in the reservoir contacts the protrusion.

4. The apparatus of claim 1, wherein the reservoir includes a bottom surface that is orthogonal to the capillary.

5. The apparatus of claim 1, wherein the capillary is one of a plurality of capillaries fixedly coupled to the body and in fluid communication with the reservoir.

6. The apparatus of claim 5, wherein the plurality of capillaries includes twenty five capillaries with a total resistivity within a range of 1 to 2 M-ohm.

7. The apparatus of claim 1, wherein the capillary has a length within a range of 2 centimeters to 20 centimeters.

8. The apparatus of claim 7, wherein the capillary has a lumen with a diameter within a range of 10 micrometers to 1000 micrometers.

9. The apparatus of claim 1, wherein the capillary has a rounded cross-sectional shape.

10. The apparatus of claim 1, wherein the capillary extends from the body in a curvilinear path.

* * * * *